(12) United States Patent
Siedler et al.

(10) Patent No.: US 11,875,298 B2
(45) Date of Patent: Jan. 16, 2024

(54) SENSOR FOR NADP (H) AND DEVELOPMENT OF ALCOHOL DEHYDROGENASES

(71) Applicant: FORSCHUNGSZENTRUM JULICH GMBH, Julich (DE)

(72) Inventors: Solvej Siedler, Aachen (DE); Georg Schendzielorz, Dusseldorf (DE); Stephan Binder, Eschweiler (DE); Lothar Eggeling, Julich (DE); Stephanie Bringer-Meyer, Julich (DE); Michael Bott, Julich (DE)

(73) Assignee: Forschungszentrum Julich GMBH, Julich (DE)

( * ) Notice: Subject to any disclaimer, the term of this patent is extended or adjusted under 35 U.S.C. 154(b) by 1041 days.

(21) Appl. No.: 16/518,544

(22) Filed: Jul. 22, 2019

(65) Prior Publication Data

US 2020/0027049 A1 Jan. 23, 2020
US 2023/0297924 A9 Sep. 21, 2023

Related U.S. Application Data

(62) Division of application No. 14/424,559, filed as application No. PCT/EP2013/002481 on Aug. 16, 2013, now Pat. No. 10,385,349.

(30) Foreign Application Priority Data

Aug. 28, 2012 (DE) ..................... 10 2012 017 026.2

(51) Int. Cl.
C12Q 1/6897 (2018.01)
G06Q 10/0639 (2023.01)
(Continued)

(52) U.S. Cl.
CPC ....... *G06Q 10/06395* (2013.01); *A61K 31/07* (2013.01); *C12N 15/70* (2013.01);
(Continued)

(58) Field of Classification Search
CPC ...... C12N 15/09; C12N 15/70; C12Q 1/6897; C12Q 1/68; C12Y 101/01; C12Y 101/01001; C12Y 101/01002
See application file for complete search history.

(56) References Cited

U.S. PATENT DOCUMENTS

2014/0255489 A1 9/2014 Shi
2015/0065947 A1 3/2015 Wallace et al.
(Continued)

OTHER PUBLICATIONS

Gu Xian Yi Shin "Composite material for Bone Repair Based on Accellular Tissue Matrix and Its Preparation" Jun. 27, 2019. Dermis, Chapter 1 pp. 13-17.

*Primary Examiner* — Allison M Fox
*Assistant Examiner* — Qing Xu
(74) *Attorney, Agent, or Firm* — Blank Rome LLP

(57) ABSTRACT

An NADP(H) nanosensor has i) a nucleic acid sequence to which a regulator is capable of binding, wherein the oxidation state of the regulator depends on the NADP(H) availability; ii) a promoter sequence following the nucleic acid sequence i), to which an RNA polymerase is capable of binding, wherein the affinity of the RNA polymerase for the promoter sequence is influenced by the oxidation state of the regulator; iii) a nucleic acid sequence which is under the control of the promoter sequence ii) and which codes for an autofluorescent protein. The present invention also relates to a cell, a method for isolating genes which code for NADP (H)-dependent enzymes, and the use of an NADP(H) nanosensor.

8 Claims, 3 Drawing Sheets

Specification includes a Sequence Listing.

(51) Int. Cl.
- *G06N 5/045* (2023.01)
- *A61K 31/07* (2006.01)
- *C12N 15/70* (2006.01)
- *G06N 3/006* (2023.01)
- *G06Q 10/04* (2023.01)
- *C12Q 1/26* (2006.01)
- *C12Q 1/68* (2018.01)

(52) U.S. Cl.
CPC .......... *C12Q 1/6897* (2013.01); *C12Y 101/00* (2013.01); *G06N 3/006* (2013.01); *G06N 5/045* (2013.01); *G06Q 10/04* (2013.01); *C12Q 1/26* (2013.01); *C12Q 1/68* (2013.01)

(56) References Cited

U.S. PATENT DOCUMENTS

| | | | |
|---|---|---|---|
| 2015/0299715 A1* | 10/2015 | Siedler | C12Q 1/6897 435/252.32 |
| 2015/0343117 A1 | 12/2015 | Ling et al. | |

\* cited by examiner

SENSOR FOR NADP (H) AND DEVELOPMENT OF ALCOHOL DEHYDROGENASES

RELATED APPLICATION

This application is Divisional of U.S. application Ser. No. 14/424,559 filed Feb. 27, 2015, now U.S. Pat. No. 10,385,349, which is a National Stage application of PCT/EP2013/002481 filed Aug. 16, 2013, which claims priority to German Patent Application No. 10 2012 017 026.2 filed Aug. 28, 2012, the entire disclosures of which are hereby incorporated by reference.

BACKGROUND OF THE INVENTION

The present invention relates to an NADP(H) nanosensor, a cell, a method for isolating genes which code for NADP (H)-dependent enzymes, and the use of an NADP(H) nanosensor.

The use of NADP(H)-dependent enzymes in the chemical industry as a catalyst is disclosed in a large number of examples. Thus, alcohol dehydrogenases, also called oxidoreductases or ketoreductases, are employed for reducing carbonyl groups. In particular, the enantiospecificity and regiospecificity is used for reducing prochiral ketones. Examples of such ketoreductases which serve for the synthesis of useful chemical compounds are the asymmetric reduction of 4-chloroacetoacetate esters (U.S. Pat. Nos. 5,559,030, 5,700,670 and 5,891,685), the reduction of dicarboxylic acids (U.S. Pat. No. 6,399,339), the reduction of tert-butyl-(S)-chloro-5-hydroxy-3-oxohexanoate (U.S. Pat. No. 6,645,746 and WO-A-01/40450), the reduction of pyrrolotriazine-based compounds (US-A-2006/0286646), the reduction of substituted acetophenones (U.S. Pat. No. 6,800,477, US-A-2012/0178142) or the reduction of hydroxythiolanes (WO-A-2005/054491). alpha-haloketones are likewise reduced enzymatically to alpha-haloalcohols. This can also be carried out by isolated enzymes or with whole cells (WO-A-2008/038050). By means of specific alcohol dehydrogenases from *Lactobacillus brevis* or *Thermoanaerobium brokii*, the reduction of the 8-chloro-6-oxooctanoic acid alkyl ester to the (R)- or (S)-8-chloro-6-hydroxyoctanoic acid alkyl ester, which is used as the precursor of (R)-α-lipoic acid and (S)-α-lipoic acid respectively, is effected (U.S. Pat. No. 7,157,253). Processes for the preparation of optically active alkanols wherein the preparation of, for example, (1S)-3-methylamino-1-(2-thienyl)-propan-1-ol and (1S)-3-chloro-1-(2-thienyl)-propan-1-ol is carried out by enzymatic reduction of the corresponding ketones are also described (WO-A-2006/094945). A process for preparing 3-hydroxybutyl 3-hydroxybutyrates enantiospecifically by means of ketoreductase or alcohol dehydrogenase is likewise known (US-A-2012/0064611). U.S. Pat. No. 6,645,746 discloses an amino acid sequence from *Candida magnoliae* which can be used for reducing tert-butyl-(5S)-6-chloro-5-hydroxy-3-oxohexanoate to tert-butyl-(3R,5S)-6-chloro-3,5-dihydroxyhexa-noate with the aid of NADP(H). In the description of this document the enzyme preferably co-expressed with glucose dehydrogenase from *Bacillus megaterium* is employed, the regeneration of the cofactor NADP(H) being carried out with the aid of glucose dehydrogenase and with glucose as a cosubstrate. WO-A-2004/111083 describes a process for the enantioselective enzymatic reduction of ketones, in particular 2- and 3-oxo acid esters, wherein the reaction is catalysed by an oxidoreductase from *Pichia capsulata*. WO-A-2005/108593 describes a process for the preparation of 1-butanol in which 2-butanone is reduced with a carbonyl reductase, for example from *Candida parapsilosis*, and a coenzyme in a two-phase system. EP-A-2 061 880 discloses a process for the NADP(H)-dependent enzymatic preparation of alkenone derivatives from α,β-unsaturated alkynone derivatives, wherein the corresponding reductase is used in purified form or also in the form of the microorganism itself. EP-A-2 087 127 describes a process for the preparation of secol derivatives by enantioselective enzymatic reduction of secodione derivatives using an oxidoreductase/dehydrogenase in the presence of NADP(H).

In addition to the NADP(H)-dependent reduction of ketones and aldehydes, NADP(H)-dependent enzymes, so-called enoate reductases, are also used for enantiospecific reduction of enoates. Thus, Kataoka and colleagues have reported that by using an enoate reductase from *Candida macedoniensis* together with an NADP(H)-generating glucose dehydrogenase from *E. coli* ketoisophorone is reduced preparatively to (6R)-levodione (Kataoka, Kotaka, Thiwthong, Wada, Nakamori, and Shimizu, *J. Biotechnol.*, 2004, 114, 1-9).

The use of NADP(H)-dependent enzymes in coupled systems where, for example, the reduction is followed by a cyclisation to the epoxide is furthermore described. The use of (R)- or (S)-selective alcohol dehydrogenases in order to form the corresponding enantiomer and subsequently to achieve the base-induced cyclisation to the particular epoxide is thus described (CA 2 612 407).

Enzymatic provision of NADP(H) is also necessary if monooxygenases are employed, as in the case of the very thoroughly investigated monooxygenase P450 BM3 (CYP102A1) from *Bacillus megaterium* (*Appl. Microbiol. Biotechnol.* (2012) 95:357-367). This fatty acid hydroxylase oxidises a wide range of substrates, such as alkanes, alkenes and aromatic hydrocarbons. The monooxygenase catalyses the hydroxylation, but requires the stoichiometric supply of NADP(H).

NADP(H)-dependent enzymes are also employed for reductive amination, such as, for example, of 2-keto acids to the corresponding D-amino acid (WO-A-2006/113085), or of 6-aminocaproic acid from 2-ketopimelate (WO-A-2012/031911).

An overview of the most diverse uses of NADP(H)-dependent enzymes can be found, for example, in Hollmann, Arendsa and Holtmann (*Green Chemistry*, 2011, 13, 2285-2313), or also the textbook "*Industrial Biotransformations*" by Liese, Seelbach, and Wandrey (Wiley-VCH Verlag, 2006, ISBN: 3-527-31001-0).

Regardless of the concrete reaction for which NADP(H)-dependent enzymes are to be employed, it is initially a prerequisite to provide suitable enzymes which ensure high conversions and a high stereospecificity. A prerequisite of this in turn is screening for such enzymes, which can be carried out in various ways.

Thus, companies offer enzyme collections, which must then be tested to ascertain whether they convert the desired educt into the desired product, such as, for example, Novozymes A/S located in Bagsværd, Denmark. Desired enzymes can also be used by utilisation of the natural diversitivity. For example, by obtaining enzymes from organisms or metagenomic libraries, which in turn must be tested specifically. Diversitivity can also be established by man by mutagenising existing enzymes and then testing the enzymes obtained for modified substrate specificity. Examples for generating various enzymes by molecular techniques are disclosed in WO-A-2012/069434, where NADP(H)-dependent enzymes for the preparation of n-heterocyclic optically active alcohols are obtained. Similar processes for the preparation of 12α-hydroxysteroid dehydrogenase mutants are also described (EP-A-2 441 771). The preparation of large gene libraries which undergo an analysis with a high throughput comprises cloning of the gene library into replicable expression vectors, transforming of the suitable cells with the resulting vector library and expressing the combinantly obtained genes under conditions under which the detection of the desired activity and the isolation of the vector which codes for the gene of which the product has been detected are facilitated.

The direct test for desired conversion of the educt into the product has hitherto preferably been carried out in microtiter plates with 96, 384 or even 1,536 wells. These plates render possible parallel testing of 96, 384 or 1,536 enzymes. The product of the desired enzyme reaction can be determined directly by chromatography techniques. This method requires the removal of a sample from the 96, 384 or 1,536 wells and chromatographic separation for detection of the reaction products, which can be, for example, alcohols or carbonyl compounds. Needless to say, such a procedure is complex and time-consuming. Indirect tests are therefore often used. The fact that NADP(H) absorbs at 340 nm but NADP does not is thus utilised. The amount of NADP(H) consumed can in principle be determined via this. Alternatively, in the carbonyl reductase-catalysed oxidation of an alcohol the conversion of NADP into NADP(H) can also be measured in this way. In this and comparable reactions, the reduction of the cofactor NADP is determined by the increase in absorption at 340 nm.

The intrinsic fluorescence of the reduced cofactor can equally also be used for the quantification. This is effected in microtiter reader apparatuses.

In another method for determining the NADP(H) consumption for detection of the enzymatic reductive transamination and also the reduction of ketones, the change in pH accompanying the NADP(H) consumption is determined by a colour indicator (U.S. Pat. No. 7,642,073). By a suitable choice of the colour indicator the wavelength of the change in colour can be determined, which in turn is determined in microtiter reader apparatuses.

Specific microtiter plate systems in which a screening in the microtiter plate format with up to 1,536 wells is carried out via membranes with specific analyte binding properties and liquid streams are also described (EP-A-1 628 768).

Attempts have also been made to make analytes more easily detectable by coupling with a detectable group, for example of a fluorophore. For this, the analyte is covalently bonded to a fluorescent group before the reaction is carried out. When the reaction is carried out and the analyte is correspondingly reacted, the fluorescence of the fluorescent group should change, for example by splitting off of the group or by a change in the structure of the analyte. The change in fluorescence is then a measure of the conversion of the analyte. A disadvantage of this, however, is that the fluorescent group often influences the reactivity of the analyte. WO-A-2007/131696 describes that by providing a fluorescent dyestuff and a macrocyclic structure in the sample to be investigated and measuring a fluorescence property of the fluorescent dyestuff at two points in time at least, the analyte concentration can be determined. The macrocyclic structure thereby binds the dyestuff and within the concentration range to be investigated for the analyte this displaces the fluorescent dyestuff from the macrocyclic structure.

In the in vitro screening set-ups known from the prior art for isolating new NADP(H)-consuming enzymes or NADP(H)-consuming enzymes from gene libraries having a modified substrate specificity, a general disadvantage is that microtiter plate systems which do not render possible high throughput screening such as is possible, for example, with fluorescence-activated cell sorting (FACS) are used.

Furthermore, in in vitro screening set-ups for isolating new NADP(H)-dependent enzymes, cell lysates are often employed as a potential source of new enzymes, since isolation in the pure form is operationally difficult. The problem of such lysates or preparations in routine screening for new NADP(H)-dependent enzymes is, however, that the reaction batch typically contains insoluble material or other enzymes which interact with the NADP(H). This leads to high blank values or also a modified non-specific absorption at 340 nm, which reduces the accuracy and the value of the absorption measurement. The same applies to fluorescence measurement of the cofactor, which is likewise made difficult by insoluble material.

SUMMARY OF THE INVENTION

The present invention was based on the object of overcoming the disadvantages emerging from the prior art in connection with isolating new NADP(H)-dependent enzymes.

In particular, the present invention was based on the object of providing a tool which can be used in order to be able to isolate in a high throughput screening, for example by means of FACS, from a cell suspension in the simplest possible manner those cells which possibly express new NADP(H)-dependent enzymes. In particular, the isolation of these cells should comprise no cell breakdown, and in particular also no analytical determination of the concentration of particular educts, products or cofactors.

The present invention was moreover based on the object of providing a cell which, after a gene for a potential NADP(H)-dependent enzyme, for example in the form of a plasmid, has been introduced into the cell, can be analysed particularly easily, and in particular without the need for a cell breakdown, as to whether the gene expressed by this cell in fact codes for an NADP(H)-dependent enzyme. A cell identified in this manner should moreover should be able to be separated off as far as possible in a targeted manner in a high throughput screening, for example by means of FACS, from a large number of cells, for example from a cell suspension.

A contribution towards achieving the abovementioned objects is made by an NADP(H) nanosensor comprising
  i) a nucleic acid sequence to which a regulator is capable of binding, wherein the oxidation state of the regulator depends on the NADP(H) availability;
  ii) a promoter sequence following the nucleic acid sequence i), to which an RNA polymerase is capable of binding, wherein the affinity of the RNA polymerase for the promoter sequence is influenced by the oxidation state of the regulator;
  iii) a nucleic acid sequence which is under the control of the promoter sequence ii) and which codes for an autofluorescent protein.

It has been found, surprisingly, that using the NADP(H) nanosensor according to the invention the intracellular NADP or NADP(H) concentration, and therefore indirectly the activity of NADP(H)-dependent enzymes in a cell, can be determined in vivo particularly easily. If a cell containing the NADP(H) nanosensor according to the invention is characterised by a high activity of NADP(H)-dependent enzymes, the concentration of NADP is correspondingly high (and the NADP(H) concentration correspondingly low). Depending on this reduction state of the cell, the regulator is capable of influencing the affinity of the RNA polymerase for the promoter controlling the expression of the autofluorescent protein, or the stability of the mRNA coding for the autofluorescent protein. The expression of the autofluorescent protein is thus controlled according to the reduction state of the cell, and in turn can be monitored in a simple manner by irradiation with electromagnetic radiation, which excites the autofluorescent protein to emission of light. The emission of light by the cells is thus an indicator for the reduction state of the cell and consequently for the extent of the expression of NADP(H)-dependent enzymes.

According to a preferred embodiment of the NADP(H) nanosensor according to the invention, the regulator is the Sox regulator (SoxR) and the promoter sequence is the soxS promoter sequence. The gene for SoxR from *E. coli* K12 is deposited under accession numbers b4063, ECK4055 in the National Center for Biotechnology Information (NCBI) database of the National Library of Medicine (Bethesda, MD, USA). SoxR contains two [2Fe-2S] clusters, which are essential for the transcription activity. Each SoxR polypeptide contains a [2Fe-2S] cluster which detects the reduction state of the cell. Both Fe-SoxR and apo-SoxR bind to the promoter region, but only Fe-SoxR contributes towards promoter activation in the oxidised form. The redox state of the iron-sulphur cluster regulates the SoxR activity. The target gene of SoxR is the adjacent soxS, the sequence of which is deposited under numbers b4062, ECK4054 in the National Center for Biotechnology Information (NCBI) database of the National Library of Medicine (Bethesda, MD, USA). The reduction state of the cell can be promoted, if appropriate, by NADP(H)-dependent reductases, such as Rsx or RseC.

In this connection it is furthermore preferable for components i) and ii) to be formed by the intergenic region from *E. coli*, which is located between soxR and soxS and which comprises the SoxR binding sequence, the soxS promoter sequence following the SoxR binding sequence and a sequence following the soxS promoter sequence, which corresponds at the level of the mRNA to a ribosome binding site, or by a nucleic acid sequence homologous to this. Components i) and ii) in this context are preferably formed by a nucleic acid sequence selected from the group consisting of:
  a) a nucleic acid sequence according to SEQ. ID. No. 01,
  b) a nucleic acid sequence which has an identity of at least 70%, preferably at least 80%, still more preferably at least 85%, still more preferably at least 90%, still more preferably at least 91%, still more preferably at least 92%, still more preferably at least 93%, still more preferably at least 94%, still more preferably at least 95%, still more preferably at least 96%, still more preferably at least 97%, still more preferably at least 98% and most preferably at least 99% to the nucleic acid sequence of a), the nucleic acid sequence being able to bind SoxR such that the affinity of the RNA polymerase for the soxS promoter depends on the oxidation state of SoxR, and
  c) a nucleic acid sequence which is capable of hybridising under stringent conditions with a complementary nucleic acid sequence according to a) or b), the nucleic acid sequence being able to bind SoxR such that the affinity of the RNA polymerase for the soxS promoter depends on the oxidation state of SoxR.

According to a first variant of this particularly preferred embodiment of the NADP(H) nanosensor according to the invention, this comprises
  (α1) the *E. coli* gene for SoxR (soxR) or a nucleic acid sequence homologous to this;
  (α2) the intergenic region from *E. coli*, following (α1), which is located between soxR and soxS and which comprises the SoxR binding sequence, the soxS promoter sequence following the SoxR binding sequence and a sequence following the soxS promoter sequence, which at the level of the mRNA corresponds to a ribosome binding site, or a nucleic acid sequence homologous to this, as defined above, as components i) and ii);
  (α3) if appropriate a part sequence, following (α2), of the soxS gene from *E. coli* or a nucleic acid sequence homologous to this;
  (α4) a nucleic acid sequence, which codes for an autofluorescent protein, following (α2) or (α3), preferably (α3) and which is under the control of the soxS promoter sequence, as component iii).

The wording "a sequence b) following a sequence a)" as used above and also in the following is to be understood according to the invention as meaning that the sequence b) does not necessarily have to be bonded directly to the sequence a), but that an intermediate sequence can also be located between sequence a) and sequence b).

According to this particular embodiment, the NADP(H) nanosensor comprises as component (α1) the *E. coli* gene for soxR (soxR) or a nucleic acid sequence homologous to this, component (α1) preferably being selected from the group consisting of:
  a) a nucleic acid sequence according to SEQ. ID. No. 02,
  b) a nucleic acid sequence coding for a polypeptide with an amino acid sequence according to SEQ. ID. No. 03,
  c) a nucleic acid sequence which has an identity of at least 70%, preferably at least 80%, still more preferably at least 85%, still more preferably at least 90%, still more preferably at least 91%, still more preferably at least 92%, still more preferably at least 93%, still more preferably at least 94%, still more preferably at least 95%, still more preferably at least 96%, still more preferably at least 97%, still more preferably at least 98% and most preferably at least 99% to the nucleic acid sequence of a) or b), the nucleic acid sequence coding for a polypeptide which is capable of binding to the SoxR binding sequence in the intergenic region from *E. coli* which is located between soxR and soxS and the oxidation state thereof being capable of influencing the affinity of the RNA polymerase for the promoter sequence likewise located in the intergenic region from *E. coli*,
  d) a nucleic acid sequence coding for a polypeptide which has a homology of at least 70%, preferably at least 80%, still more preferably at least 85%, still more preferably at least 90%, still more preferably at least 91%, still more preferably at least 92%, still more preferably at least 93%, still more preferably at least 94%, still more preferably at least 95%, still more preferably at least 96%, still more preferably at least 97%, still more preferably at least 98% and most preferably at least 99% to SEQ. ID. No. 03, the nucleic acid sequence coding for a polypeptide which is capable of binding to the SoxR binding sequence in the intergenic region from *E. coli* which is located between soxR and soxS and the oxidation state thereof being capable of influencing the affinity of the RNA polymerase for the promoter sequence likewise located in the intergenic region from *E. coli*, and e) a nucleic acid sequence which is capable of hybridising under stringent conditions with a complementary nucleic acid sequence according to one of groups a) to d), the nucleic acid sequence coding for a polypeptide which is capable of binding to the SoxR binding sequence in the intergenic region from *E. coli* which is located between soxR and soxS and the oxidation state thereof being capable of influencing the affinity of the RNA polymerase for the promoter sequence likewise located in the intergenic region from *E. coli*.

The expression "homology" (or "identity") as used herein can be defined by the equation H (%)=[1−V/X]×100, wherein H denotes homology, X is the total number of nucleobases/amino acids of the comparison sequence and V is the number of different nucleobases/amino acids of the sequence to be considered, with respect to the comparison sequence. In all cases, the term nucleic acid sequences which code for polypeptides includes all sequences which appear to be possible according to the proviso of degeneration of the genetic code.

The identity of nucleic acid sequences can be identified using a sequence comparison program (BLAST, Altschul et al. *J. Mol. Biol.* 1990, 215, 403-410). The percentage homology between two amino acid sequences can likewise be readily determined by the person skilled in the art using methods know from the prior art. A suitable program which can be employed according to the invention is BLASTp (Altschul et al. 1997; "Gapped BLAST and PSI-BLAST: a new generation of protein database search programs"; *Nucleic Acids Res.* 25(17): 3389-3402).

The person skilled in the art can find instructions for hybridisation inter alia in the handbook "*The DIG System User's Guide for Filter Hybridization*" of Boehringer Mannheim GmbH (Mannheim, Germany, 1993) and in Liebl et al. (*International Journal of Systematic Bacteriology* 41: 255-260 (1991)). The hybridisation takes place under stringent conditions, that is to say only hybrids in which the probe, for example the nucleotide sequence complementary to soxR or soxS or the intergenic region of soxRS from *E. coli*, and the target sequence, i.e. the polynucleotides treated with the probe, are at least 70% identical. It is known that the stringency of the hybridisation including the washing steps is influenced or determined by varying the buffer composition, the temperature and the salt concentration. The hybridisation reaction is in general carried out at a relatively low stringency compared with the washing steps (Hybaid Hybridisation Guide, Hybaid Limited, Teddington, U K, 1996). For the hybridisation reaction, for example, a buffer corresponding to 5×SSC buffer can be employed at a temperature of approx. 50° C.-68° C. In this context probes can also hybridise with polynucleotides which have less than 70% identity to the sequence of the probe. Such hybrids are less stable and are removed by washing under stringent conditions. This can be achieved, for example, by lowering the salt concentration to 2×SSC and if appropriate subsequently 0.5×SSC (The DIG System User's Guide for Filter Hybridization, Boehringer Mannheim, Mannheim, Germany, 1995), a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. being established. Preferably, the washing steps are carried out at temperatures of approx. 62° C.-68° C., preferably of 64° C.-68° C. or approx. 66° C.-68° C., particularly preferably of approx. 66° C.-68° C. It is possible, where appropriate, to lower the salt concentration to a concentration corresponding to 0.2×SSC or 0.1×SSC. By increasing the hybridisation temperature stepwise in steps of approx. 1-2° C. from 50° C. to 68° C., polynucleotide fragments which code for soxR or soxS or the intergenic region of soxRS which have, for example, at least 70% or at least 80% or at least 90% to 95% or at least 96% to 98% or at least 99% identity to the sequence of the probe employed can be isolated. Further instructions for the hybridisation are obtainable on the market in the form of so-called kits (e.g. DIG Easy Hyb from Roche Diagnostics GmbH, Mannheim, Germany, catalogue no. 1603558).

The NADP(H) nanosensor according to this particular embodiment comprises as component (α4) a nucleic acid sequence which codes for an autofluorescent protein and which follows (α2) or α3), preferably the target gene soxS (α3), in particular the first 5 to 200 nucleotides of the target gene soxS, and is under the control the soxS promoter sequence, as component iii).

According to the invention, the gene sequence according to component iii) coding for the autofluorescent protein is under the control of the promoter sequence ii) (according to the first variant described above for the particular embodiment of the NADP(H) nanosensor according to the invention, the gene sequence (α4) coding for the autofluorescent protein is under the control of the soxS promoter sequence). The term "under the control of the promoter sequence" in this context is preferably to be understood as meaning that the gene sequence coding for the autofluorescent protein is functionally linked to the promoter. The promoter and the gene sequence coding for the autofluorescent protein are functionally linked if these two sequences and optionally further regulative elements, such as, for example, a terminator or a ribosome binding site, are arranged sequentially such that each of the regulative elements can fulfil its function in the transgenic expression of the nucleic acid sequence. For this, a direct linking in the chemical sense is not absolutely necessary. Genetic control sequences, such as, for example, enhancer sequences, can also exert their function on the target sequence from further removed positions or even from other DNA molecules. Arrangements in which the gene sequence coding for the autofluorescent protein is positioned after the promoter sequence (i.e. at the 3' end), so that the two sequences are bonded covalently to one another, are preferred. Preferably, in this context the distance between the gene sequence coding for the autofluorescent protein and the promoter sequence is less than 200 base pairs, particularly preferably less than 100 base pairs, very particularly preferably less than 50 base pairs. It is also possible for the gene sequence coding for the autofluorescent protein and the promoter to be linked functionally to one another such that there is still a part sequence of the homologous gene (that is to say that gene of which the expression in the wild-type cell is regulated by the promoter) between these two gene sequences (according to the particular embodiment of the NADP(H) nanosensor described above, parts of the soxS gene according to component (α3) can accordingly be between the soxS promoter sequence and the nucleic acid sequence (α4) coding for the autofluorescent protein). In the expression of such a DNA construct, a fusion protein is obtained from the autofluorescent protein and the amino acid sequence which is coded by the corresponding part sequence of the homologous gene (=translational fusion). The lengths of such part sequences of the homologous gene are not critical as long as the functional capacity of the autofluorescent protein, that is to say its property of being fluorescent when excited with light of a particular wavelength, is not noticeably impaired. In the case of the particular embodiment of the NADP(H) nanosensor according to the invention described above, the soxS part sequence (α3) preferably comprises at least the first 5 nucleotides, still more preferably at least the first 10 nucleotides and still more preferably at least the first 20 nucleotides, but preferably at most the first 200 nucleotides, still more preferably at most the first 150 nucleotides and still more preferably at most the first 100 nucleotides of the soxS gene.

The nucleic acid sequence (iii) (or (α4) and (β4)) coding for an autofluorescent protein preferably comprises genes coding for fluorescent proteins which code for fluorescent proteins of the genus *Aequora*, such as green fluorescent protein (GFP), and variants thereof which are fluorescent in a different wavelength range (e.g. yellow fluorescent protein (YFP), blue fluorescent protein (BFP), cyan fluorescent protein (CFP)) or of which the fluorescence is enhanced (e.g. enhanced green fluorescent protein (EGFP), enhanced yellow fluorescent protein (EYFP), enhanced blue fluorescent protein (EBFP) or enhanced cyan fluorescent protein (ECFP). Gene sequences which code for other autofluorescent proteins, e.g. DsRed, HcRed, AsRed, AmCyan, ZsGreen, AcGFP, ZsYellow, such as are known from BD Biosciences, Franklin Lakes, USA, can furthermore also be used according to the invention. A photoreceptor protein which contains a so-called LOV domain can likewise be used. The particularly preferred autofluorescent protein in this context is EYFP.

According to a second variant of the particularly preferred embodiment of the NADP(H) nanosensor according to the invention, this comprises
- (β1) the *E. coli* gene for SoxR (soxR) or a nucleic acid sequence homologous to this;
- (β2) the intergenic region from *E. coli*, following (β1), which is located between soxR and soxS and which comprises the SoxR binding sequence, the soxS promoter sequence following the SoxR binding sequence and a sequence following the soxS promoter sequence which at the level of the mRNA corresponds to a ribosome binding site, or a nucleic acid sequence homologous to this, as defined above, as components i) and ii);
- (β3) the sequence of the soxS gene from *E. coli* following (β2) and under the control of the soxS promoter sequence, a part sequence of this gene or a nucleic acid sequence homologous to this;
- (β3') a further sequence following (β3) which at the mRNA level corresponds to a ribosome binding site;
- (β4) a nucleic acid sequence, which codes for an autofluorescent protein, following (β3') and which is under the control of the soxS promoter sequence, as component iii).

Components (β1), (β2), (β3) and (β4) which are preferred are those components which have already been mentioned above as preferred components (α1), (α2), (α3) and (α4) in connection with the first variant of the particularly preferred embodiment of the NADP(H) nanosensor according to the invention, During the expression of such a DNA construct, SoxS or a fragment of this protein and, separately from this, the autofluorescent protein are formed (=transcriptional fusion).

A contribution towards achieving the abovementioned objects is also made by a cell comprising an NADP(H) nanosensor according to the invention. In this context the NADP(H) nanosensor according to the invention can be present in the cell in the episomal or chromosomal form.

Examples of suitable cells which may be mentioned in particular are *Escherichia coli, Pseudomonas fluorescens, Corynebacterium glutamicum, Bacillus subtilis* or another *Eubacterium*, or also *Saccharomyces cerevisiae* or another yeast.

The cells according to the invention are suitable for establishing whether particular gene sequences code for an NADP(H)-dependent enzyme. For this, the gene coding for a potential NADP(H)-dependent enzyme is introduced into the cell and expressed. As described above, the emission of light by the cells is an indicator for the reduction state of the cell and consequently for the extent of the expression of NADP(H)-dependent enzymes.

In this context, according to the invention an "NADP(H)-dependent enzyme" is understood as meaning any enzyme which is involved in at least a part step of the conversion of a substrate into a reaction product which is chemically different from this substrate, NADP(H) being involved as a cofactor in at least one part step of this conversion.

According to a preferred embodiment of the cell according to the invention, this accordingly furthermore comprises, in addition to the NADP(H) nanosensor according to the invention, a plasmid with an optionally mutated gene which codes for an NADP(H)-dependent enzyme. The NADP(H)-dependent enzyme in this context is preferably selected from the group consisting of alcohol dehydrogenases, aldehyde dehydrogenases, lactate dehydrogenases, enoate reductases, epoxide reductases, diaminopimelate dehydrogenases, amino acid dehydrogenases, aldehyde oxidoreductases, alkane reductases, amine reductases, epoxide dehydrogenases, carboxylic acid dehydrogenases, hydroxy acid ketoreductases and hydroxy acid dehalogenases.

A contribution towards achieving the abovementioned objects is also made by a recombinant cell comprising a nucleic acid sequence coding for an autofluorescent protein, wherein the extent of the expression of the autofluorescent protein in the cell depends on the intracellular NADP(H) availability. In this connection particularly preferred cells are the cells described above, in particular cells comprising the NADP(H) sensor according to the invention.

A contribution towards achieving the abovementioned objects is also made by a method for isolating genes which code for NADP(H)-dependent enzymes, comprising the method steps:
- (I) providing an NADP(H) nanosensor according to the invention;
- (II) introducing the NADP(H) nanosensor into a cell;
- (III) introducing a gene which may code for an NADP(H)-dependent enzyme into individual cells of a cell suspension of the cells obtained in method step (II);
- (IV) incubating the cells with a substrate for the NADP(H)-dependent enzyme;
- (V) identifying individual cells in the cell suspension with an increased activity of NADP(H)-dependent enzymes by detection of the intracellular fluorescence activity;
- (VI) separating off the identified cells from the cell suspension;
- (VII) isolating the genes coding for an NADP(H)-dependent enzyme in the identified cells.

New NADP(H)-dependent enzymes and mutated NADP(H)-dependent enzymes with increased or modified substrate recognition can be isolated with the aid of this method.

Sensors and cells which are preferred as the NADP(H) sensor and as the cell are those which have already been described above as preferred sensors or cells in connection with the sensor according to the invention or the cell according to the invention.

In method steps (I) and (II) a cell according to the invention is first prepared by introducing the NADP(H) nanosensor according to the invention into a cell, it being possible for this introduction to be carried out in the episomal or chromosomal form.

In method step (III) of the method according to the invention a gene which may code for an NADP(H)-dependent enzyme is then introduced into individual cells of a cell suspension of the cells obtained in method step (II), it being possible for the gene to be, in particular, a mutated, plasmid-coded gene of an NADP(H)-dependent enzyme. To introduce the site-nonspecific mutations into the plasmid-coded genes of the NADP(H)-dependent enzymes to increase the diversity, an in vitro mutagenesis is preferably carried out with the aid of an error-prone polymerase chain reaction (PCR) and an amplification technique. In this context the gene to be mutated is subjected to a PCR using a polymerase which, depending on the conditions of the reaction, incorporates individual bases incorrectly into the synthesized genes (Tindall, K. R. and T. A. Kunkel: "Fidelity of DNA synthesis by the *Thermus aquaticus* DNA polymerase"; Biochemistry, 1988, 27 (16), pages 6008-13). A frequent variant of this method comprises the use of manganese(II) ions or of nucleotide analogues in the PCR batch (Cadwell R. C et al. (1992); PCR Methods Appl. (2), pages 28-33/ Leung D. W. et al. (1989) Techniques (1), pages 11-15). These techniques for introduction of mutations are called "error-prone PCR (epPCR)" (Labrou N E: "Random mutagenesis methods for in vitro directed enzyme evolution"; Curr. Protein. Pept. Sci. 2010 (11), pages:91-100). The mutations can be, for example, point mutations, and e.g. substitutions, deletions or insertions can be generated by the polymerase. The mutation rate is between 1-40 mutations per 1 kb, preferably 1-5 mutations per 1 kb. However, mutations can also be produced with the aid of saturation mutagenesis using the Stratagene QuikChange Kit (La Jolla, California, USA), or also using a method called SeSam (EP 1 670 914 B 1), with which any existing nucleotide is transferred under saturation into any possible nucleotide.

Possible NADP(H)-dependent enzymes of which the activity can be analysed with the nanosensor-carrying host in a high throughput are, for example, 1,2-dehydroreticulin reductases (1.5.1.27), 2-enoyl-CoA reductase (1.3.1.10), 2-enoyl-CoA reductases (1.3.1.39), alkenal/one oxidoreductases (1.3.1.74) cytochrome P450 reductase (1.6.2.4), NADP(H) dehydrogenases (1.6.99.1), NADP(H) dehydrogenases (flavin) (1.6.8.2), NADP(H) dehydrogenases (quinone) (1.6.5.10), NADP(H)-dependent 1,5-anhydro-D-fructose reductases (1.1.1.263), NADP(H)-dependent cytochrome P450 reductases (1.6.2.4), diaphorases (1.6.99.1), DT-diaphorases (1.6.5.5), ferredoxin reductases (1.18.1.2), NADP(H) oxidases (1.6.3.1, 1.6.5.10, 1.6.3.1, 1.6.3.1, 1.6.3.1), P450 oxidoreductase (1.6.2.4), P450 reductase (1.6.2.4), peroxidase (1.11.1.2), quinone acceptor oxidoreductase (1.6.5.5), quinone oxidoreductase (1.6.5.10), NADP(H)-specific FMN reductase (1.5.1.38), thioredoxin reductase (1.8.1.9), transhydrogenase (1.6.1.2), NADP(H)-aldehyde reductase (1.1.1.2), aldopentose reductase (1.1.1.21), NADP(H)-aldose reductase (1.1.1.21), NADP (H)-carbonyl reductase (1.1.1.184), NADP(H)-CYP reductase (1.6.2.4), NADP(H)-cytochrome c oxidoreductase (1.6.2.4), NADP(H)-cytochrome c reductase (1.1.1.2), NADP(H)-cytochrome f reductase (1.6.2.5), NADP(H)-cytochrome P450 reductase (1.6.2.4) and NADP(H)-cytochrome P450 reductase (1.14.13.68).

The plasmids which contain mutations in genes of the NADP(H)-dependent enzymes are then introduced into the microorganism, such as, for example, *E. coli* or *C. glutamicum*, by transformation. In this context the term "transformation" includes all methods for transfer of polynucleotides, in particular DNA, into a desired bacterium. These include inter alia the use of isolated DNA in transformation, electro transformation or electroporation, transfer by cell contact, as in conjugation, or transfer of DNA by means of particle bombardment.

After in process step (III) a gene which optionally codes for an NADP(H)-dependent enzyme has been introduced into individual cells of a cell suspension from the cells obtained in method (II) (and expressed), the cells are then incubated in method step (IV) with a substrate for an NADP(H)-dependent enzyme, and in method step (V) individual cells in the cell suspension with an increased activity of NADP(H)-dependent enzymes are then identified by detection of the intracellular fluorescence activity. For this, the cell suspension is exposed to electromagnetic radiation in that frequency which excites the autofluorescent protein of the NADP(H) nanosensor to emission of light.

In method step (VI) the identified cells are then separated off from the cell suspension, this separating off preferably being carried out by means of flow cytometry (FACS=fluorescence activated cell sorting), very particularly preferably by means of high throughput flow cytometry (HT-FACS=high throughput fluorescence activated cell sorting). Details on the analysis of cell suspensions by means of flow cytometry can be found, for example, in Sack U, Tarnok A, Rothe G (eds.): Zellulare Diagnostik. Grundlagen, Methoden and klinische Anwendungen der Durchflusszytometrie, Basel, Karger, 2007, pages 27-70.

In method step (VII) the genes coding for an NADP(H)-dependent enzyme in the identified cells are then isolated and if appropriate analysed, for example by isolating the enzyme-carrying plasmids from the cells which have been separated off and identifying and verifying, by sequencing, their mutation which lead to modified fluorescence.

A contribution towards achieving the abovementioned objects is also made by the use of the NADP(H) nanosensor according to the invention for identifying, in vivo, genes which code for an NADP(H)-dependent enzyme.

BRIEF DESCRIPTION OF THE DRAWINGS

The invention is now explained in more detail with the aid of figures and non-limiting examples.

DETAILED DESCRIPTION

Figure 1:
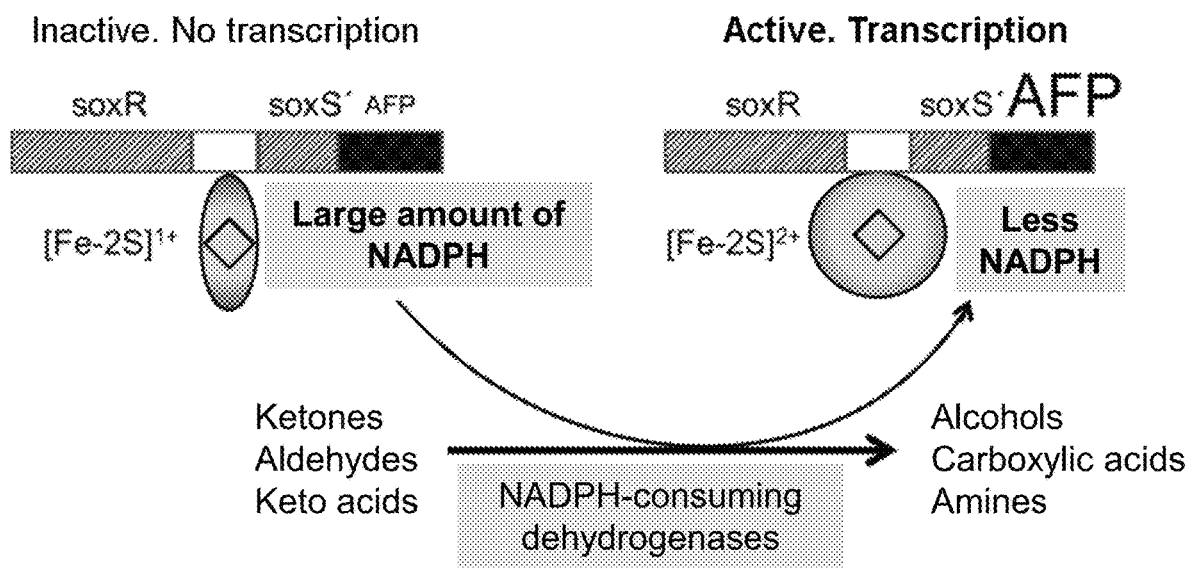
FIG. 1 shows the mode of functioning of the NADP(H) nanosensor according to the invention by the example of the particularly preferred embodiment described above.

According to FIG. 1, the NADP(H) nanosensor can comprise the *E. coli* gene for SoxR (soxR), the intergenic region from *E. coli* following this, which is located between soxR and soxS and which comprises the soxR binding sequence and the soxS promoter sequence following the SoxR binding sequence, a part sequence of the soxS gene from *E. coli* (soxS') following this and a nucleic acid sequence following this, under the control of the soxS promoter sequence, which codes for a autofluorescent protein (AFP). At a high cytosol NADP(H) concentration (top left in FIG. 1), the [2Fe-2S] clusters (rhomb) are present in a form reduced by SoxR bound to the promoter. At a low NADP(H) availability (top right in FIG. 1), the [2Fe-2S] clusters are oxidised, and the resulting distortion of the soxS promoter region renders transcription initiation of the target gene possible for the RNA polymerase. According to the invention the native target gene soxS is fused with an autofluorescent protein (AFP). NADP(H)-dependent enzymes cause increased expression of soxS'-AFP by consumption of NADP(H) and therefore increased fluorescence of cells as a result of increased NADP(H) consumption.

Figure 3:
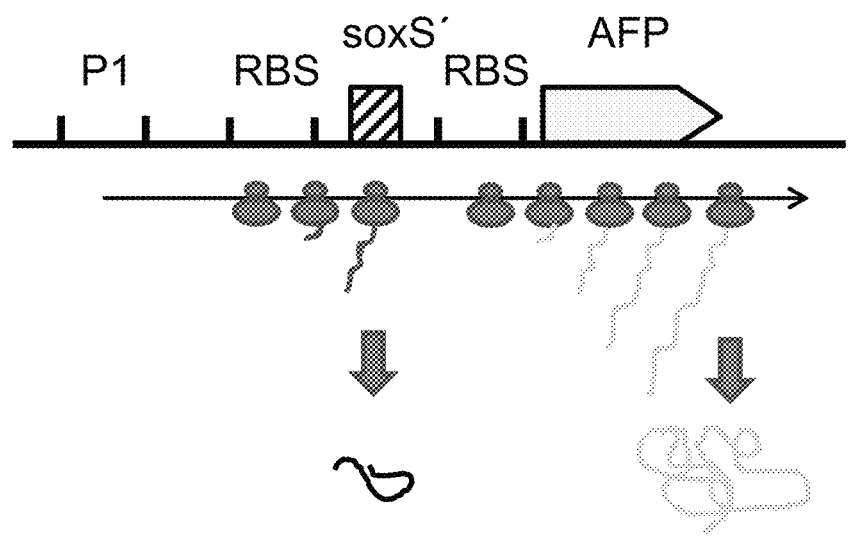
FIG. 3 shows a diagram of the formation of the autofluorescent protein as transcriptional (top) and translational (bottom) fusion.
Figure 3:
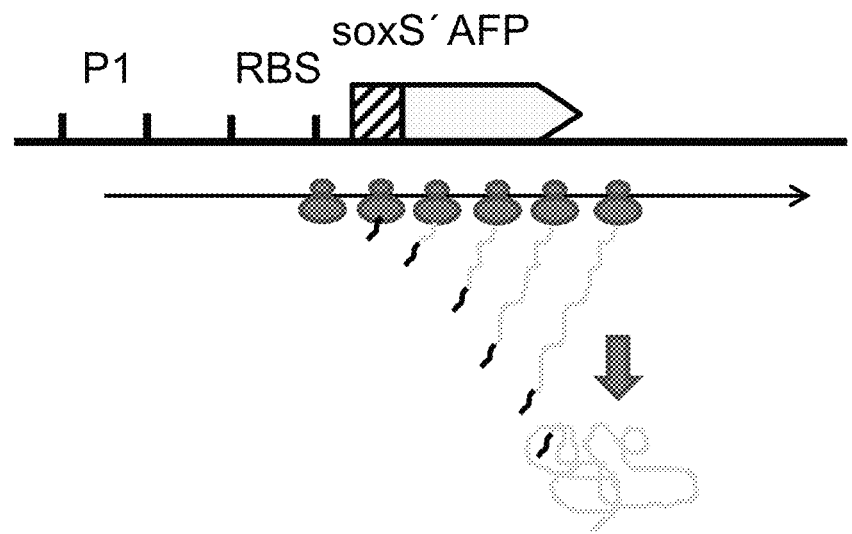

FIG. 3 shows at the top the transcriptional and at the bottom the translational fusion. In both cases a transcript is formed by the promoter P1, which is, for example, the soxS promoter controlled by SoxR. Whereas during transcriptional fusion two separate peptides are formed due to a second ribosome binding site (RBS), during translational fusion a single peptide is formed, the fusion protein, in which the autofluorescent protein contains additional amino acid sequences.

EXAMPLES

Example 1

Construction of the NADPH Nanosensor (Transcriptional Fusion)

With the primer pairs SoxS_for_SphI (SEQ. ID. No. 04) and SoxR_rev_SalI (SEQ. ID. No. 05) and chromosomal DNA from *E. coli* DH5a as the template, the gene soxR was amplified together with the intergenic region of soxR-soxS and the first 63 nucleotides of soxS.

```
SoxS_for_SphI:
ATCTGCATGCTTACGGCTGGTCAATATGCTCGTC

SoxR_rev_SalI:
GCTAGTCGACCAAACTAAAGCGCCCTTGTG
```

With the primer pairs EYFP_for_SphI (SEQ. ID. No. 06) and EYFP_rev_ClaI (SEQ. ID. No. 07) and the vector pSenLys as the template, the gene eyfp was amplified together with a ribosome binding site. The vector pSenLys is described in the patent application WO-A-2011/138006.

```
EYFP_for_SphI:
AGAGGCATGCAAGGAGAATTACATGGTGAGCAAGGGCGAGG

EYFP_rev_ClaI:
GCGCATCGATTTATTACTTGTACAGCTCGTCCATG
```

The vector pBtacLbadh codes for the NADPH-dependent alcohol dehydrogenase from *Lactobacillus brevis* (Lbadh). It is described in Ernst et al. (Ernst M, Kaup B, Müller M, Bringer-Meyer S, Sahm H, Appl. Microbiol. Biotechnol. 2005, 66(6), pages 629-34). The vector pBtacLbadh was treated with the restriction enzymes SalI and ClaI, and the vector fragment ~5.0 kb in size was isolated from the agarose gel and treated with alkaline phosphatase and purified with the QIAquick Gel Extraction Kit (cat. no. 28704) from Quiagen (Hilden, Germany). The two PCR products and the vector were then ligated by means of T4 DNA ligase from New England BioLabs (New England Biolabs, 240 County Road, Ipswich, MA 01938-2723). The ligation batch was transformed directly into the *E. coli* strain DH5a. Selection of plasmid-carrying cells was carried out by plating out the transformation batch on LB agar (Sambrook et al.: "Molecular cloning: a laboratory manual", 2nd edition, Cold Spring Harbor Laboratory Press, Cold Spring Harbor, NY), which had been supplemented with 50 mg/l of ampicillin. Plasmid DNA was isolated from a transformant and checked by treatment with the restriction enzyme BamHI with subsequent agarose gel electrophoresis. The plasmid was called pSenSox and is deposited as the sequence SEQ. ID. No. 08.

pSennegK was created as a derivative with modified alcohol dehydrogenase, Lbadh. For this, with the primers ADH_negK_for (SEQ. ID. No. 09) and ADH_negK_rev (SEQ. ID. No. 10) and again pBtacLbadh as the template, an inactive Lbadh was amplified with an alcohol dehydrogenase deleted by 221 bp. The resulting fragment was ligated with the ~5.7 kb size vector fragment containing the gene eyfp together with a ribosome binding site. The sequence of the resulting vector is deposited as SEQ. ID. No. 11.

```
ADH_negK_for:
ACAAGAATTCGCTAAGAGTGTCGGCACTCC

ADH_negK_rev:
GGCCAAGCTTCCGAAGAAGACACCATCAAG
``` pSen-L194S was created as a further derivative with modified alcohol dehydrogenase, Lbadh. For this, with the primers L194S_for (SEQ. ID. No. 12) and L194S_rev (SEQ. ID. No. 13), pSenSox was amplified as a template for targeted insertion of the mutation. The plasmid generated was verified by means of sequencing. The sequence of the resulting vector is deposited as SEQ. ID. No. 14.

```
L194S_for:
CTGGCTACATCAAGACACCATCTGTTGATG

L194S_rev:
CGGCCCCTGGTAGGTCATCAACAGATGGTG
``` pSen-L194A was created as a further derivative with modified alcohol dehydrogenase, Lbadh. For this, with the primers L194A_for (SEQ. ID. No. 15) and L194A_rev (SEQ. ID. No. 16), pSenSox was amplified as a template for targeted insertion of the mutation. The plasmid generated was verified by means of sequencing. The sequence of the resulting vector is deposited as SEQ. ID. No. 17.

```
L194A_for:
CTGGCTACATCAAGACACCAGCGGTTGATG

L194A_rev:
CGGCCCCTGGTAGGTCATCAACCGCTGGTG
```

Example 2

Use of the NADP(H) Nanosensor for Monitoring Alcohol Dehydrogenase-Dependent Product Formation

*E. coli* BL21(DE3) (Life Technologies GmbH, Frankfurter Straße 129B, 64293 Darmstadt) was transformed with the plasmid pSenSox. 5 ml of 2×YT medium (16 g/l of tryptone, 10 g/l of yeast extract, 5 g/l of NaCl) was inoculated with an individual colony and the culture was incubated overnight at 37° C. and 130 rpm. Using this preculture the main culture was inoculated to an OD of 0.05 in 50 ml of 2×TY and was incubated at 37° C. and 130 rpm. At the OD of 0.3 1 mM IPTG was added and the culture was incubated for a further 3 hours to an OD of 5-6.

Figure 2:
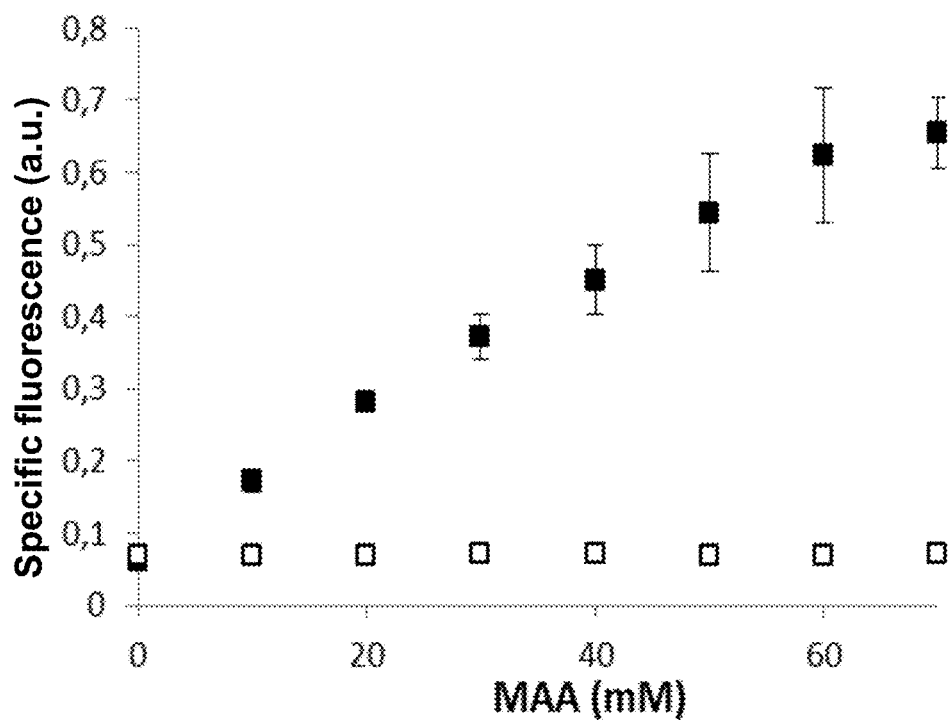
FIG. 2 shows the specific fluorescence of the *E. coli* BL21(DE3) cells, prepared in Example 3, with the NADP (H) nanosensor according to the invention (pSensox) and expressed alcohol dehydrogenase (Lbadh) (solid squares). The fluorescence of the nanosensor pSennegK with inactive alcohol dehydrogenase is shown as a control (open squares).

0.9 ml portions of the cell suspension were then introduced into a reaction vessel of the Flowerplate microtiter plate (48-well) of the BioLector cultivation system (m2plabs GmbH, Aachen, Germany). Methyl acetoacetate (MAA) was added to the cell suspension in increasing concentration in a constant volume of 0.1 ml. The Flowerplate microtiter plate was then incubated at 30° C., 1,200 rpm, shaking radius 3 mm. In the BioLector cultivation system the growth was recorded online as scattered light at 620 nm, and the fluorescence of the culture was recorded continuously at an excitation wavelength of 485 nm and an emission wavelength of 520 nm. The specific fluorescence after 10 hours was plotted against the amount of MAA added and is shown in FIG. 2 (0-70 mM methyl acetoacetate was added to individual batches and after 10 hours the specific fluorescence was determined, this being shown as squares filled with black; *E. coli* BL21(DE3) pSennegK with inactive Lbadh served as a negative control (empty squares). FIG. 2 shows an increase in the fluorescence with increasing MAA concentration. This increase is due to pSenSox, since a control reaction with the plasmid pSennegK with inactive alcohol dehydrogenase, which, however, is otherwise identical to pSenSox, causes no increase in fluorescence.

Example 3

Use of the NADP(H) Nanosensor for Determining Different Alcohol Dehydrogenase Activities The strain *E. coli* BL21(DE3) (Life Technologies GmbH, Frankfurter Straße 129B, 64293 Darmstadt) was transformed in each case with pSennegK, pSen-L194S and pSen-L194A. In addition, the strain *E. coli* BL21(DE3) pSenSox described in Example 2 was transformed with pET28a as the second plasmid. The vector mentioned last was obtained from Novagen (Life Technologies GmbH, Frankfurter Straße 129B, 64293 Darmstadt). 5 ml of 2×YT medium (16 g/l of tryptone, 10 g/l of yeast extract, 5 g/l of NaCl) was inoculated with an individual colony of the particular strain and the culture was incubated overnight at 37° C. and 130 rpm. Using this preculture the main culture was inoculated to an OD of 0.05 in 50 ml of 2×TY and was incubated at 37° C. and 130 rpm. At the OD of 0.3 no IPTG was added or 1 mM IPTG was added to the strain *E. coli* BL21(DE3) pSenSox and the culture was incubated for a further 3 hours to an OD of 5-6.

As described in Example 2, 0.9 ml portions of the cells were then each introduced into a reaction vessel of the Flowerplate microtiter plate (48-well) of the BioLector cultivation system (m2plabs GmbH, Aachen, Germany). Methyl acetoacetate (MAA) was in each case added, in 0.1 ml, to the cell suspension to a final concentration of 40 mM. The Flowerplate microtiter plate was then incubated at 30° C., 1,200 rpm, shaking radius 3 mm, and the specific fluorescence was determined. The specific fluorescence obtained after 19 hours is shown in Table 1.

In addition, the alcohol dehydrogenase activity of the recombinant *E. coli* cells was determined in the individual batches. For this, the cells were harvested at 10,000×g, 4° C., 5 min and taken up in 100 mM potassium phosphate buffer, pH 6.5, 1 mM dithiothreitol, 1 mM $MgCl_2$. The cells were broken down by means of the Silamat S5 (Ivoclar Vivadent GmbH, Germany) with the aid of glass beads of 0.1 mm diameter. The crude extract which was obtained after centrifugation at 16,000×g, 4° C., 20 min was employed in the enzyme test for quantification of the alcohol dehydrogenase activity. The test contained 5 mM methyl acetoacetate, 0.25 mM NADPH and 1 mM $MgCl_2$ in 100 mM potassium phosphate buffer, pH 6.5, and 0.01-0.1 ml of crude extract. The reduction of NADP(H) was monitored at 340 nm and 30° C. An enzyme unit (U) is stated as that amount of crude extract which reduces 0.001 mmol of NADP(H) per minute. It is likewise given in Table 1.

Example 4

Isolation of Mutated Alcohol Dehydrogenase with Modified Substrate Recognition

The alcohol dehydrogenase Lbadh from *Lactococcus lactis* has a high activity with methyl acetoacetate, but only a low activity of about 10% with 4-methyl-2-pentanone as the substrate. In order to evolve an Lbadh with a higher activity, random mutations were inserted into pSenSox by error-prone PCR (epPCR). To insert the mutations, 10 ng of pSenSox were employed as the template per reaction, as well as 0.1-0.8 mM $Mn^{2+}$, at the lower concentrations of below <0.2 mM $Mn^{2+}$ a total concentration of at least 0.2 mM being established with $Mg^{2+}$. 0.5 µl of Taq polymerase from Fermentas (catalogue no. EP0401) was added per reaction. The polynucleotides SEQ. ID. No. 18:
ACAAGAATTCGCTAAGAGTGTCGGCACTCC SEQ. ID. No. 19:
GGCCAAGCTTCCGAAGAAGACACCATCAAG were used as primers. The reactions were incubated for 30 minutes. The reaction products were then treated with BamHI and SalI and ligated with the vector pSenSox likewise treated beforehand.

*E. coli* DH5αmcr was transformed with the ligation products (Grant, 1990, Proceedings of the National Academy of Sciences, USA, 87, pages 4645-4649). After incubation for 30 h, transformants were washed off from the plates with 10 ml of 2×YT and diluted tenfold in fresh 2×YT medium. After incubation for 4 hours at 37° C., 20 mM 4-methyl-2-pentanone was added as the substrate, and after a further incubation for three hours the batches were sent for FACS analysis and sorting.

For FACS analysis and sorting of the cells with high fluorescence, the cell suspension in 2×YT medium was adjusted to an optical density of less than 0.1 and passed immediately to the FACS ARIA II high-speed cell sorter (Becton Dickinson GmbH, Tullastr. 8-12, 69126 Heidelberg). The analysis was carried out with the excitation wavelengths of 488 and 633 nm and the detection at the emission wavelengths of 530±15 nm and 660±10 nm under a sample pressure of 70 psi. The data were analysed with the software version BD DIVA 6.1.3 belonging to the apparatus. BD FACSflow was used as the sheath fluid. The electronic gating was set with the aid of the forward and backward scatter in order to exclude non-bacterial particles. In order to sort EYFP-positive cells, the next level of the electronic gating was selected, in order to exclude non-fluorescent cells. In this manner, 123 fluorescent cells were sorted out on Petri dishes which contained 2×YT medium.

Reaction vessels of the Flowerplate microtiter plate (48-well) of the BioLector cultivation system (m2plabs GmbH, Aachen, Germany) were inoculated, as described in Example 2, with the colonies obtained after incubation for 30 hours at 37° C. However, 20 mM 4-methyl-2-pentanone and not methyl acetoacetate was used as the substrate. After 120 minutes the specific fluorescence was quantified, and a clone was selected, the alcohol dehydrogenase activity of which was determined in the enzyme test as described in Example 3. 20 mM 4-methyl-2-pentanone was used as the substrate here.

The mutant with the plasmid pSen-A93M obtained in this way has a specific activity increased by 26% compared with the starting strain (Table 2), and a conversion rate with 4-methyl-2-pentanone as the substrate increased by 37%. The sequence of the plasmid pSen-A93M is deposited as SEQ. ID. No. 20.

TABLE 1

Correlation of the alcohol dehydrogenase activity of whole cells with the specific fluorescence.

| Strain | IPTG | Alcohol dehydrogenase activity (U mg$^{-1}$) | Specific fluorescence |
|---|---|---|---|
| BL21(DE3) pSennegK | – | 0.03 ± 0.01 | 0.06 |
| BL21(DE3) pSenSox, pET28a | – | 0.5 ± 0.1 | 0.09 |
| BL21(DE3) pSenL194S | – | 0.7 ± 0.3 | 0.11 |
| BL21(DE3) pSenL194A | – | 2.7 ± 0.6 | 0.17 |
| BL21(DE3) pSenSox | – | 6.2 ± 0.6 | 0.38 |
| BL21(DE3) pSenSox | + | 15.2 ± 2.0 | 0.45 |

TABLE 2

Increase in the activity and conversion rate of the alcohol dehydrogenase isolated by means of the NADP(H) nanosensor and FACS with 4-methyl-2-pentanone as the substrate.

| Strain | Alcohol dehydrogenase activity (U mg$^{-1}$) | $v_{max}$ (U mg$^{-1}$) | $K_M$ (mM) |
|---|---|---|---|
| DH5α pSensox | 1.9 ± 0.2 | 1.9 ± 0.02 | 0.10 ± 0.01 |
| DH5α pSenA93M | 2.4 ± 0.1 | 2.6 ± 0.03 | 0.88 ± 0.03 |

Example 5

Construction of the NADPH Nanosensor (Translational Fusion)

With the primer pairs SoxS_for_SphI_tl (SEQ. ID. No. 21) and SoxR_rev_SalI_tl (SEQ. ID. No. 22) and chromosomal DNA from *E. coli* DH5a as the template, the gene soxR was amplified together with the intergenic region of soxR-soxS and the first 63 nucleotides of soxS.

SoxS_for_SphI_tl:
ATCTGCATGCCGGCTGGTCAATATGCTCGTC

SoxR_rev_SalI_tl:
GCTAGTCGACCAAACTAAAGCGCCCTTGTG

With the primer pairs EYFP_for_SphI_tl (SEQ. ID. No. 23) and EYFP_rev_ClaI_tl (SEQ. ID. No. 24) and the vector pSenLys as the template, the gene eyfp was amplified. The vector pSenLys is described in the patent application WO-A-2011/138006.

EYFP_for_SphI_tl:
AGAGGCATGCGTGAGCAAGGGCGAGG

EYFP_rev_ClaI_tl:
GCGCATCGATTTATTACTTGTACAGCTCGTCCATG

The vector pBtacLbadh codes for the NADPH-dependent alcohol dehydrogenase from *Lactobacillus brevis* (Lbadh). It is described in Ernst et al. (Ernst M, Kaup B, Müller M, Bringer-Meyer S, Sahm H, Appl. Microbiol. Biotechnol. 2005, 66(6), pages 629-34). The vector pBtacLbadh was treated with the restriction enzymes SalI and ClaI, and the vector fragment 5.0 kb in size was isolated from the agarose gel and treated with alkaline phosphatase and purified with the QIAquick Gel Extraction Kit (cat. no. 28704) from Quiagen (Hilden, Germany). The two PCR products and the vector were then ligated by means of T4 DNA ligase from New England BioLabs (New England Biolabs, 240 County Road, Ipswich, MA 01938-2723). The ligation batch was transformed directly into the *E. coli* strain DH5a. Selection of plasmid-carrying cells was carried out by plating out the transformation batch on LB agar (Sambrook et al.: "Molecular cloning: a laboratory manual", 2nd edition, Cold Spring Harbor Laboratory Press, Cold Spring Harbor, NY), which had been supplemented with 50 mg/l of ampicillin. Plasmid DNA was isolated from a transformant and checked by treatment with the restriction enzyme BamHI with subsequent agarose gel electrophoresis. The plasmid was called pSenSox_tl and is deposited as the sequence SEQ. ID. No. 25.

SEQUENCES

```
                                                      SEQ. ID. No. 01
     aaatctgcct cttttcagtg ttcagttcgt taattcatct gttggggagt ataattcctc     60
aagttaactt gaggtaaagc gattt                                           85

SEQ. ID. No. 02
     atggaaaaga aattaccccg cattaaagcg ctgctaaccc ccggcgaagt ggcgaaacgc     60
agcggtgtgg cggtatcggc gctgcatttc tatgaaagta aaggttgat taccagtatc    120 cgtaacagcg gcaatcagcg gcgatataaa cgtgatgtgt tgcgatatgt tgcaattatc    180
aaaattgctc agcgtattgg cattccgctg gcgaccattg gtgaagcgtt tggcgtgttg    240
cccgaagggc atacgttaag tgcgaaagag tggaaacagc tttcgtccca atggcgagaa    300
```

-continued

```
gagttggatc ggcgcattca taccttagtg gcgctgcgtg acgaactgga cggatgtatt       360
ggttgtggct gcctttcgcg cagtgattgc ccgttgcgta acccgggcga ccgcttagga       420
gaagaaggta ccggcgcacg cttgctggaa gatgaacaaa actaa                       465
```

SEQ. ID. No. 03

```
MEKKLPRIKA LLTPGEVAKR SGVAVSALHF YESKGLITSI RNSGNQRRYK RDVLRYVAII        60

KIAQRIGIPL ATIGEAFGVL PEGHTLSAKE WKQLSSQWRE ELDRRIHTLV ALRDELDGCI       120

GCGCLSRSDC PLRNPGDRLG EEGTGARLLE DEQN                                   154
```

SEQ. ID. No. 04

```
atctgcatgc ttacggctgg tcaatatgct cgtc                                    34
```

SEQ. ID. No. 05

```
gctagtcgac caaactaaag cgcccttgtg                                         30
```

SEQ. ID. No. 06

```
agaggcatgc aaggagaatt acatggtgag caagggcgag g                            41
```

SEQ. ID. No. 07

```
gcgcatcgat ttattacttg tacagctcgt ccatg                                   35
```

SEQ. ID. No. 08

```
ttcatgtcta accgtttgga tggtaaggta gcaatcatta caggtggtac gttgggtatc        60
ggtttagcta tcgccacgaa gttcgttgaa aaggggcta aggtcatgat taccggccgg       120
cacagcgatg ttggtgaaaa agcagctaag agtgtcggca ctcctgatca gattcaattt       180
ttccaacatg attcttccga tgaagacggc tggacgaaat tattcgatgc aacgaaaaaa       240
gcctttggcc cagtttctac attagttaat aacgctggga tcgcggttaa caagagtgtc       300
gaagaaacca cgactgctga atggcgtaaa ttattagccg tcaaccttga tggtgtcttc       360
ttcggtaccc gattagggat tcaacggatg aagaacaaag gcttaggggc ttccatcatc       420
aacatgtctt cgatcgaagg ctttgtgggt gatcctagct tagggcctta caacgcatct       480
aaaggggccg tacggattat gtccaagtca gctgccttag attgtgccct aaaggactac       540
gatgttcggg taaacactgt tcaccctggc tacatcaaga caccattggt tgatgaccta       600
ccaggggccg aagaagcgat gtcacaacgg accaagacgc caatgggcca tatcggtgaa       660
cctaacgata ttgcctacat ctgtgtttac ttggcttcta acgaatctaa atttgcaacg       720
ggttctgaat ttgtagttga cggtggctac actgctcaat agtaagcttc tgttttggcg       780
gatgagagaa gattttcagc ctgatacaga ttaaatcaga acgcagaagc ggtctgataa       840
aacagaattt gcctggcggc agtagcgcgg tggtcccacc tgaccccatg ccgaactcag       900
aagtgaaacg ccgtagcgcc gatggtagtg tggggtctcc ccatgcgaga gtagggaact       960
gccaggcatc aaataaaacg aaaggctcag tcgaaagact gggcctttcg ttttatctgt      1020
tgtttgtcgg tgaacgctct cctgagtagg acaaatccgc cgggagcgga tttgaacgtt      1080
gcgaagcaac ggcccggagg gtggcgggca ggacgcccgc cataaactgc caggcatcaa      1140
attaagcaga aggccatcct gacggatggc ctttttgcgt ttctacaaac tcttttgttt      1200 attttttctaa atacattcaa atatgtatcc gctcatgaga caataaccct gataaatgct      1260
tcaataatat tgaaaaagga agagtatgag tattcaacat ttccgtgtcg cccttattcc      1320
cttttttgcg gcattttgcc ttcctgtttt tgctcaccca gaaacgctgg tgaaagtaaa      1380
agatgctgaa gatcagttgg gtgcacgagt gggttacatc gaactggatc tcaacagcgg      1440
taagatcctt gagagttttc gccccgaaga acgttttcca atgatgagca cttttaaagt      1500
tctgctatgt ggcgcggtat tatcccgtgt tgacgccggg caagagcaac tcggtcgccg      1560
catacactat tctcagaatg acttggttga gtactcacca gtcacagaaa agcatcttac      1620
ggatggcatg acagtaagag aattatgcag tgctgccata accatgagtg ataacactgc      1680
```

-continued

```
ggccaactta cttctgacaa cgatcggagg accgaaggag ctaaccgctt ttttgcacaa    1740
catgggggat catgtaactc gccttgatcg ttgggaaccg gagctgaatg aagccatacc    1800
aaacgacgag cgtgacacca cgatgcctgt agcaatggca acaacgttgc gcaaactatt    1860
aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg ggtctcgcgg tatcattgca gcactggggc cagatggtaa    2040
gccctcccgt atcgtagtta tctacacgac ggggagtcag gcaactatgg atgaacgaaa    2100
tagacagatc gctgagatag gtgcctcact gattaagcat tcgtaactgt cagaccaagt    2160
ttactcatat atactttaga ttgatttaaa acttcatttt taatttaaaa ggatctaggt    2220
gaagatcctt tttgataatc tcatgaccaa aatcccttaa cgtgagtttt cgttccactg    2280
agcgtcagac cccgtagaaa agatcaaagg atcttcttga gatcctttt ttctgcgcgt    2340 aatctgctgc ttgcaaacaa aaaaaccacc gctaccagcg gtggtttgtt tgccggatca    2400
agagctacca actctttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata gtcgtgtct    2580 taccggggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccagggggaa acgcctggta    2820
tctttatagt cctgtcgggt ttcgccacct ctgacttgag cgtcgatttt tgtgatgctc    2880 gtcaggggggg cggagcctat ggaaaaacgc cagcaacgcg gccttttac ggttcctggc    2940 cttttgctgg ccttttgctc acatgttctt tcctgcgtta tccctgatt ctgtggataa    3000 ccgtattacc gcctttgagt gagctgatac cgctcgccgc agccgaacga ccgagcgcag    3060
cgagtcagtg agcgaggaag cggaagagcg cctgatgcgg tattttctcc ttacgcatct    3120
gtgcggtatt tcacaccgca tatggtgcac tctcagtaca atctgctctg atgccgcata    3180
gttaagccag tatacactcc gctatcgcta cgtgactggg tcatggctgc gccccgacac    3240
ccgccaacac ccgctgacgc gccctgacgg gcttgtctgc tcccggcatc cgcttacaga    3300
caagctgtga ccgtctccgg gagctgcatg tgtcagaggt tttcaccgtc atcaccgaaa    3360
cgcgcgaggc agctgcggta agctcatca gcgtggtcgt gaagcgattc acagatgtct    3420
gcctgttcat ccgcgtccag ctcgttgagt ttctccagaa gcgttaatgt ctggcttctg    3480
ataaagcggg ccatgttaag gcggttttt tcctgtttgg tcacttgatg cctccgtgta    3540 aggggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
```

```
gcgcattcac agttctccgc aagaattgat tggctccaat tcttggagtg gtgaatccgt      4140
tagcgaggtg ccgccggctt ccattcaggt cgaggtggcc cggctccatg caccgcgacg      4200
caacgcgggg aggcagacaa ggtatagggc ggcgcctaca atccatgcca acccgttcca      4260
tgtgctcgcc gaggcggcat aaatcgccgt gacgatcagc ggtccagtga tcgaagttag      4320
gctggtaaga gccgcgagcg atccttgaag ctgtccctga tggtcgtcat ctacctgcct      4380
ggacagcatg gcctgcaacg cgggcatccc gatgccgccg gaagcgagaa gaatcataat      4440
ggggaaggcc atccagcctc gcgtcgcgaa cgccagcaag acgtagccca gcgcgtcggc      4500
cgccatgccg gcgataatgg cctgcttctc gccgaaacgt ttggtggcgg gaccagtgac      4560
gaaggcttga gcgagggcgt graagattcc gaataccgca agcgacaggc cgatcatcgt      4620
cgcgctccag cgaaagcggt cctcgccgaa aatgacccag agcgctgccg gcacctgtcc      4680
tacgagttgc atgataaaga agacagtcat aagtgcggcg acgatagtca tgccccgcgc      4740
ccaccggaag gagctgactg ggttgaaggc tctcaagggc atcggtcgac caaactaaag      4800
cgcccttgtg gcgctttagt tttgttcatc ttccagcaag cgtgcgccgg taccttcttc      4860
tcctaagcgg tcgcccgggt tacgcaacgg gcaatcactg cgcgaaaggc agccacaacc      4920
aatacatccg tccagttcgt cacgcagcgc cactaaggta tgaatgcgcc gatccaactc      4980
ttctcgccat tcggacgaaa gctgtttcca ctctttcgca cttaacgtat gcccttcggg      5040
caacacgcca aacgcttcac caatggtcgc cagcggaatg ccaatacgct gagcaatttt      5100
gataattgca acatatcgca acacatcacg tttatatcgc cgctgattgc cgctgttacg      5160
gatactggta atcaacccct tactttcata gaaatgcagc gccgataccg ccacaccgct      5220
gcgtttcgcc acttcgccgg gggttagcag cgctttaatg cggggtaatt tcttttccat      5280
aaatcgcttt acctcaagtt aacttgagga attatactcc ccaacagaty aattaacgaa      5340
ctgaacactg aaaagaggca gatttatgtc ccatcagaaa attattcagg atcttatcgc      5400
atggattgac gagcatattg accagccgta agcatgcaag gagaattaca tggtgagcaa      5460
gggcgaggag ctgttcaccg gggtggtgcc catcctggtc gagctggacg gcgacgtaaa      5520
cggccacaag ttcagcgtgt ccggcgaggg cgagggcgat gccacctacg gcaagctgac      5580
cctgaagttc atctgcacca ccggcaagct gcccgtgccc tggcccaccc tcgtgaccac      5640
cttcggctac ggcctgcagt gcttcgcccg ctaccccgac cacatgaagc agcacgactt      5700
cttcaagtcc gccatgcccg aaggctacgt ccaggagcgc accatcttct tcaaggacga      5760
cggcaactac aagacccgcg ccgaggtgaa gttcgagggc gacaccctgg tgaaccgcat      5820
cgagctgaag ggcatcaact tcaaggagga cggcaacatc ctggggcaca agctggagta      5880
caactacaac agccacaacg tctatatcat ggccgacaag cagaagaacg gcatcaaggt      5940
gaacttcaag atccgccaca acatcgaggg cggcagcgtg cagctcgccg accactacca      6000
gcagaacacc cccatcggcg acggccccgt gctgctgccc gacaaccact acctgagcta      6060
ccagtccgcc ctgagcaaag accccaacga gaagcgcgat cacatggtcc tgctggagtt      6120
cgtgaccgcc gccgggatca ctctcggcat ggacgagctg tacaagtaat aaatcgatcc      6180
ggagcttatc gactgcacgg tgcaccaatg cttctggcgt caggcagcca tcggaagctg      6240
tggtatggct gtgcaggtcg taaatcactg cataattcgt gtcgctcaag gcgcactccc      6300
gttctggata atgttttttg cgccgacatc ataacggttc tggcaaatat tctgaaatga      6360
gctgttgaca attaatcatc ggctcgtata atgtgtggaa ttgtgagcgg ataacaattt      6420
cacacaggaa acagaa                                                      6436
```

```
                                                       SEQ. ID. No. 09
acaagaattc gctaagagtg tcggcactcc                             30

SEQ. ID. No. 10
ggccaagctt ccgaagaaga caccatcaag                             30

SEQ. ID. NO. 11
agcttctgtt ttggcggatg agagaagatt ttcagcctga tacagattaa atcagaacgc    60
agaagcggtc tgataaaaca gaatttgcct ggcggcagta gcgcggtggt cccacctgac   120
cccatgccga actcagaagt gaaacgccgt agcgccgatg gtagtgtggg gtctccccat   180
gcgagagtag ggaactgcca ggcatcaaat aaaacgaaag gctcagtcga agactgggc   240
cttttcgtttt atctgttgtt tgtcggtgaa cgctctcctg agtaggacaa atccgccggg   300
agcggatttg aacgttgcga agcaacggcc cggagggtgg cgggcaggac gcccgccata   360
aactgccagg catcaaatta agcagaaggc catcctgacg gatggccttt ttgcgtttct   420
acaaactctt ttgtttattt ttctaaatac attcaaatat gtatccgctc atgagacaat   480
aaccctgata aatgcttcaa taatattgaa aaggaagag tatgagtatt caacatttcc   540
gtgtcgccct tattcccttt tttgcggcat tttgccttcc tgttttgtgct cacccagaaa   600
cgctggtgaa agtaaaagat gctgaagatc agttgggtgc acgagtgggt tacatcgaac   660
tggatctcaa cagcggtaag atccttgaga gttttcgccc cgaagaacgt tttccaatga   720
tgagcacttt taaagttctg ctatgtggcg cggtattatc ccgtgttgac gccgggcaag   780
agcaactcgg tcgccgcata cactattctc agaatgactt gcttgagtac tcaccagtca   840
cagaaaagca tcttacggat ggcatgacag taagagaatt atgcagtgct gccataacca   900
tgagtgataa cactgcggcc aacttacttc tgacaacgat cggaggaccg aaggagctaa   960
ccgcttttt gcacaacatg ggggatcatg taactcgcct tgatcgttgg gaaccggagc   1020
tgaatgaagc cataccaaac gacgagcgtg acaccacgat gcctgtagca atggcaacaa   1080
cgttgcgcaa actattaact ggcgaactac ttactctagc ttcccggcaa caattaatag   1140
actggatgga ggcggataaa gttgcaggac cacttctgcg ctcggccctt ccggctggct   1200
ggtttattgc tgataaatct ggagccggtg agcgtgggtc tcgcggtatc attgcagcac   1260
tggggccaga tggtaagccc tcccgtatcg tagttatcta cacgacgggg agtcaggcaa   1320
ctatggatga acgaaataga cagatcgctg agataggtgc ctcactgatt aagcattggt   1380
aactgtcaga ccaagtttac tcatatatac tttagattga tttaaaactt cattttaat   1440
ttaaaaggat ctaggtgaag atcctttttg ataatctcat gaccaaaatc ccttaacgtg   1500
agttttcgtt ccactgagcg tcagaccccg tagaaaagat caaaggatct tcttgagatc   1560
cttttttct gcgcgtaatc tgctgcttgc aaacaaaaaa accaccgcta ccagcggtgg   1620
tttgtttgcc ggatcaagag ctaccaactc tttttccgaa ggtaactggc ttcagcagag   1680
cgcagatacc aaatactgtc cttctagtgt agccgtagtt aggccaccac ttcaagaact   1740
ctgtagcacc gcctacatac ctcgctctgc taatcctgtt accagtggct gctgccagtg   1800
gcgataagtc gtgtcttacc gggttggact caagacgata gttaccggat aaggcgcagc   1860
ggtcgggctg aacggggggt tcgtgcacac agcccagctt ggagcgaacg acctacaccg   1920
aactgagata cctacagcgt gagctatgag aaagcgccac gcttcccgaa gggagaaagg   1980
cggacaggta tccggtaagc ggcagggtcg gaacaggaga gcgcacgagg gagcttccag   2040
ggggaaacgc ctggtatctt tatagtcctg tcgggtttcg ccacctctga cttgagcgtc   2100
gattttgtg atgctcgtca ggggggcgga gcctatggaa aaacgccagc aacgcggcct   2160
ttttacggtt cctggccttt tgctggcctt ttgctcacat gttctttcct gcgttatccc   2220
```

-continued

```
ctgattctgt ggataaccgt attaccgcct ttgagtgagc tgataccgct cgccgcagcc      2280
gaacgaccga gcgcagcgag tcagtgagcg aggaagcgga agagcgcctg atgcggtatt      2340
ttctccttac gcatctgtgc ggtatttcac accgcatatg gtgcactctc agtacaatct      2400
gctctgatgc cgcatagtta agccagtata cactccgcta tcgctacgtg actgggtcat      2460
ggctgcgccc cgacacccgc caacacccgc tgacgcgccc tgacgggctt gtctgctccc      2520
ggcatccgct tacagacaag ctgtgaccgt ctccgggagc tgcatgtgtc agaggttttc      2580
accgtcatca ccgaaacgcg cgaggcagct gcggtaaagc tcatcagcgt ggtcgtgaag      2640
cgattcacag atgtctgcct gttcatccgc gtccagctcg ttgagtttct ccagaagcgt      2700
taatgtctgg cttctgataa agcgggccat gttaagggcg gttttttcct gtttggtcac      2760
ttgatgcctc cgtgtaaggg ggaatttctg ttcatggggg taatgatacc gatgaaacga      2820
gagaggatgc tcacgatacg ggttactgat gatgaacatg cccggttact ggaacgttgt      2880
gagggtaaac aactggcggt atggatgcgg cgggaccaga gaaaaatcac tcagggtcaa      2940
tgccagcgct tcgttaatac agatgtaggt gttccacagg gtagccagca gcatcctgcg      3000
atgcagatcc ggaacataat ggtgcagggc gctgacttcc gcgtttccag actttacgaa      3060
acacggaaac cgaagaccat tcatgttgtt gctcaggtcg cagacgtttt gcagcagcag      3120
tcgcttcacg ttcgctcgcg tatcggtgat tcattctgct aaccagtaag gcaaccccgc      3180
cagcctagcc gggtcctcaa cgacaggagc acgatcatgc gcacccgtgg ccaggaccca      3240
acgctgcccg agatgcgccg cgtgcggctg ctggagatgg cggacgcgat ggatatgttc      3300
tgccaagggt tggtttgcgc attcacagtt ctccgcaaga attgattggc tccaattctt      3360
ggagtggtga atccgttagc gaggtgccgc cggcttccat tcaggtcgag gtggcccggc      3420
tccatgcacc gcgacgcaac gcggggaggc agacaaggta tagggcggcg cctacaatcc      3480
atgccaaccc gttccatgtg ctcgccgagg cggcataaat cgccgtgacg atcagcggtc      3540
cagtgatcga agttaggctg gtaagagccg cgagcgatcc ttgaagctgt ccctgatggt      3600
cgtcatctac ctgcctggac agcatggcct gcaacgcggg catcccgatg ccgccggaag      3660
cgagaagaat cataatgggg aaggccatcc agcctcgcgt cgcgaacgcc agcaagacgt      3720
agcccagcgc gtcggccgcc atgccggcga taatggcctg cttctcgccg aaacgtttgg      3780
tggcgggacc agtgacgaag gcttgagcga gggcgtgcaa gattccgaat accgcaagcg      3840
acaggccgat catcgtcgcg ctccagcgaa agcggtcctc gccgaaaatg acccagagcg      3900
ctgccggcac ctgtcctacg agttgcatga taaagaagac agtcataagt gcggcgacga      3960
tagtcatgcc ccgcgcccac cggaaggagc tgactgggtt gaaggctctc aagggcatcg      4020
gtcgaccaaa ctaaagcgcc cttgtggcgc tttagttttg ttcatcttcc agcaagcgtg      4080
cgccggtacc ttcttctcct aagcggtcgc ccgggttacg caacgggcaa tcactgcgcg      4140
aaaggcagca caaccaata catccgtcca gttcgtcacg cagcgccact aaggtatgaa      4200
tgcgccgatc caactcttct cgccattggg acgaaagctg tttccactct ttcgcactta      4260
acgtatgccc ttcgggcaac acgccaaacg cttcaccaat ggtcgccagc ggaatgccaa      4320
tacgctgagc aattttgata attgcaacat atcgcaacac atcacgttta tatcgccgct      4380
gattgccgct gttacggata ctggtaatca ccctttact ttcatagaaa tgcagcgccg      4440
ataccgccac accgctgcgt ttcgccactt cgccgggggt tagcagcgct ttaatgcggg      4500
gtaatttctt ttccataaat cgctttacct caagttaact tgaggaatta tactccccaa      4560
cagatgaatt aacgaactga acactgaaaa gaggcagatt tatgtcccat cagaaaatta      4620
```

```
                                      -continued
ttcaggatct tatcgcatgg attgacgagc atattgacca gccgtaagca tgcaaggaga         4680
attacatggt gagcaagggc gaggagctgt tcaccggggt ggtgcccatc ctggtcgagc         4740
tggacggcga cgtaaacggc cacaagttca gcgtgtccgg cgagggcgag ggcgatgcca         4800
cctacggcaa gctgaccctg aagttcatct gcaccaccgg caagctgccc gtgccctggc         4860
ccaccctcgt gaccaccttc ggctacggcc tgcagtgctt cgcccgctac cccgaccaca         4920
tgaagcagca cgacttcttc aagtccgcca tgcccgaagg ctacgtccag gagcgcacca         4980
tcttcttcaa ggacgacggc aactacaaga cccgcgccga ggtgaagttc gagggcgaca         5040
ccctggtgaa ccgcatcgag ctgaagggca tcaacttcaa ggaggacggc aacatcctgg         5100
ggcacaagct ggagtacaac tacaacagcc acaacgtcta tatcatggcc gacaagcaga         5160
agaacggcat caaggtgaac ttcaagatcc gccacaacat cgaggcggc agcgtgcagc          5220 tcgccgacca ctaccagcag aacacccca tcggcgacgg ccccgtgctg ctgcccgaca          5280
accactacct gagctaccag tccgccctga gcaaagaccc caacgagaag cgcgatcaca        5340
tggtcctgct ggagttcgtg accgccgccg ggatcactct cggcatggac gagctgtaca        5400
agtaataaat cgatccggag cttatcgact gcacggtgca ccaatgcttc tggcgtcagg        5460
cagccatcgg aagctgtggt atggctgtgc aggtcgtaaa tcactgcata attcgtgtcg       5520
ctcaaggcgc actcccgttc tggataatgt tttttgcgcc gacatcataa cggttctggc      5580
aaatattctg aaatgagctg ttgacaatta atcatcggct cgtataatgt gtggaattgt       5640
gagcggataa caatttcaca caggaaacag aattcgctaa gagtgtcggc actcctgatc       5700
agattcaatt tttccaacat gattcttccg atgaagacgg ctggacgaaa ttattcgatg       5760
caacggaaaa agcctttggc ccagtttcta cattagttaa taacgctggg atcgcggtta      5820
acaagagtgt cgaagaaacc acgactgctg aatggcgtaa attattagcc gtcaaccttg      5880
atggtgtctt cttcgga                                                     5897

SEQ. ID. No. 12
ctggctacat caagacacca tctgttgatg                                          30

SEQ. ID. NO. 13
cggcccctgg taggtcatca acagatggtg                                          30

SEQ. ID. NO. 14
ttcatgtcta accgtttgga tggtaaggta gcaatcatta caggtggtac gttgggtatc        60
ggtttagcta tcgccacgaa gttcgttgaa gaagggcta aggtcatgat taccggccgg        120
cacagcgatg ttggtgaaaa agcagctaag agtgtcggca ctcctgatca gattcaattt       180
ttccaacatg attcttccga tgaagacggc tggacgaaat tattcgatgc aacggaaaaa       240
gcctttggcc cagtttctac attagttaat aacgctggga tcgcggttaa caagagtgtc      300
gaagaaacca cgactgctga atggcgtaaa ttattagccg tcaaccttga tggtgtcttc      360
ttcggtaccc gattagggat tcaacggatg aagaacaaag gcttaggggc ttccatcatc      420
aacatgtctt cgatcgaagg ctttgtgggt gatcctagct tagggcctta caacgcatct      480
aaaggggccg tacggattat gtccaagtca gctgccttag attgtgccct aaaggactac      540
gatgttcggg taaacactgt tcaccctggc tacatcaaga caccatctgt tgatgaccta      600
ccaggggccg aagaagcgat gtcacaacgg accaagacgc caatgggcca tatcggtgaa      660
cctaacgata ttgcctacat ctgtgtttac ttggcttcta cgaatctaa atttgcaacg      720 ggttctgaat ttgtagttga cggtggctac actgctcaat agtaagcttc tgttttggcg     780
gatgagagaa gattttcagc ctgatacaga ttaaatcaga acgcagaagc ggtctgataa     840
aacagaattt gcctggcggc agtagcgcgg tggtcccacc tgaccccatg ccgaactcag     900
```

-continued

```
aagtgaaacg ccgtagcgcc gatggtagtg tggggtctcc ccatgcgaga gtagggaact       960
gccaggcatc aaataaaacg aaaggctcag tcgaaagact gggcctttcg ttttatctgt      1020
tgtttgtcgg tgaacgctct cctgagtagg acaaatccgc cgggagcgga tttgaacgtt      1080
gcgaagcaac ggcccggagg gtggcgggca ggacgcccgc cataaactgc caggcatcaa      1140
attaagcaga aggccatcct gacggatggc cttttttgcgt ttctacaaac tcttttgttt    1200 attttttctaa atacattcaa atatgtatcc gctcatgaga caataaccct gataaatgct     1260
tcaataatat tgaaaaagga agagtatgag tattcaacat ttccgtgtcg cccttattcc      1320 ctttttttgcg gcattttgcc ttcctgtttt tgctcaccca gaaacgctgg tgaaagtaaa    1380
agatgctgaa gatcagttgg gtgcacgagt gggttacatc gaactggatc tcaacagcgg      1440
taagatcctt gagagttttc gccccgaaga acgttttcca atgatgagca ctttttaaagt    1500 tctgctatgt ggcgcggtat tatcccgtgt tgacgccggg caagagcaac tcggtcgccg      1560
catacactat tctcagaatg acttggttga gtactcacca gtcacagaaa agcatcttac      1620
ggatggcatg acagtaagag aattatgcag tgctgccata accatgagtg ataacactgc      1680
ggccaactta cttctgacaa cgatcggagg accgaaggag ctaaccgctt ttttgcacaa     1740
catgggggat catgtaactc gccttgatcg ttgggaaccg gagctgaatg aagccatacc      1800
aaacgacgag cgtgacacca cgatgcctgt agcaatggca acaacgttgc gcaaactatt      1860
aactggcgaa ctacttactc tagcttcccg gcaacaatta atagactgga tggaggcgga      1920
taaagttgca ggaccacttc tgcgctcggc ccttccggct ggctggttta ttgctgataa      1980
atctggagcc ggtgagcgtg gtctcgcggt atcattgca gcactgggc cagatggtaa       2040 gccctcccgt atcgtagtta tctacacgac ggggagtcag gcaactatgg atgaacgaaa     2100
tagacagatc gctgagatag gtgcctcact gattaagcat tcgtaactgt cagaccaagt     2160
ttactcatat atactttaga ttgatttaaa acttcatttt taatttaaaa ggatctaggt      2220
gaagatcctt tttgataatc tcatgaccaa aatcccttaa cgtgagtttt cgttccactg      2280
agcgtcagac cccgtagaaa agatcaaagg atcttcttga tccttttttt ttctgcgcgt      2340
aatctgctgc ttgcaaacaa aaaaaccacc gctaccagcg gtggtttgtt tgccggatca      2400
agagctacca actctttttc cgaaggtaac tggcttcagc agagcgcaga taccaaatac      2460
tgtccttcta gtgtagccgt agttaggcca ccacttcaag aactctgtag caccgcctac      2520
atacctcgct ctgctaatcc tgttaccagt ggctgctgcc agtggcgata agtcgtgtct      2580
taccgggttg gactcaagac gatagttacc ggataaggcg cagcggtcgg gctgaacggg      2640
gggttcgtgc acacagccca gcttggagcg aacgacctac accgaactga gatacctaca     2700
gcgtgagcta tgagaaagcg ccacgcttcc cgaagggaga aaggcggaca ggtatccggt      2760
aagcggcagg gtcggaacag gagagcgcac gagggagctt ccaggggaa acgcctggta       2820 tctttatagt cctgtcgggt ttcgccacct ctgacttgag cgtcgatttt tgtgatgctc      2880
gtcagggggg cggagcctat ggaaaaacgc cagcaacgcg gcctttttac ggttcctggc      2940
cttttgctgg ccttttgctc acatgttctt tcctgcgtta tcccctgatt ctgtggataa      3000
ccgtattacc gcctttgagt gagctgatac cgctcgccgc agccgaacga ccgagcgcag      3060
cgagtcagtg agcgaggaag cggaagagcg cctgatgcgg tattttctcc ttacgcatct     3120
gtgcggtatt tcacaccgca tatggtgcac tctcagtaca atctgctctg atgccgcata     3180
gttaagccag tatacactcc gctatcgcta cgtgactggg tcatggctgc gccccgacac     3240
ccgccaacac ccgctgacgc gccctgacgg gcttgtctgc tcccggcatc cgcttacaga     3300
caagctgtga ccgtctccgg gagctgcatg tgtcagaggt tttcaccgtc atcaccgaaa     3360
```

-continued

```
cgcgcgaggc agctgcggta aagctcatca gcgtggtcgt gaagcgattc acagatgtct      3420
gcctgttcat ccgcgtccag ctcgttgagt ttctccagaa gcgttaatgt ctggcttctg      3480
ataaagcggg ccatgttaag ggcggttttt tcctgtttgg tcacttgatg cctccgtgta      3540
agggggaatt tctgttcatg ggggtaatga taccgatgaa acgagagagg atgctcacga      3600
tacgggttac tgatgatgaa catgcccggt tactggaacg ttgtgagggt aaacaactgg      3660
cggtatggat gcggcgggac cagagaaaaa tcactcaggg tcaatgccag cgcttcgtta      3720
atacagatgt aggtgttcca cagggtagcc agcagcatcc tgcgatgcag atccggaaca      3780
taatggtgca gggcgctgac ttccgcgttt ccagacttta cgaaacacgg aaaccgaaga      3840
ccattcatgt tgttgctcag gtcgcagacg ttttgcagca gcagtcgctt cacgttcgct      3900
cgcgtatcgg tgattcattc tgctaaccag taaggcaacc ccgccagcct agccgggtcc      3960
tcaacgacag gagcacgatc atgcgcaccc gtggccagga cccaacgctg cccgagatgc      4020
gccgcgtgcg gctgctggag atggcggacg cgatggatat gttctgccaa gggttggttt      4080
gcgcattcac agttctccgc aagaattgat tcgctccaat tcttggagtg gtgaatccgt      4140
tagcgaggtg ccgccggctt ccattcaggt cgaggtggcc cggctccatg caccgcgacg      4200
caacgcgggg aggcagacaa ggtatagggc ggcgcctaca atccatgcca acccgttcca      4260
tgtgctcgcc gaggcggcat aaatcgccgt gacgatcagc ggtccagtga tcgaagttag      4320
gctggtaaga gccgcgagcg atccttgaag ctgtccctga tggtcgtcat ctacctgcct      4380
ggacagcatg gcctgcaacg cgggcatccc gatgccgccg gaagcgagaa gaatcataat      4440
ggggaaggcc atccagcctc gcgtcgcgaa cgccagcaag acgtagccca gcgcgtcggc      4500
cgccatgccg gcgataatgg cctgcttctc gccgaaacgt ttggtggcgg accagtgac      4560 gaaggcttga gcgagggcgt gcaagattcc gaataccgca agcgacaggc cgatcatcgt      4620
cgcgctccag cgaaagcggt cctcgccgaa aatgacccag agcgctgccg gcacctgtcc      4680
tacgagttgc atgataaaga agacagtcat aagtgcggcg acgatagtca tgccccgcgc      4740
ccaccggaag gagctgactg ggttgaaggc tctcaagggc atcggtcgac caaactaaag      4800
cgcccttgtg gcgctttagt tttgttcatc ttccagcaag cgtgcgccgg taccttcttc      4860
tcctaagcgg tcgcccgggt tacgcaacgg gcaatcactg cgcgaaaggc agccacaacc      4920
aatacatccg tccagttcgt cacgcagcgc cactaaggta tgaatgcgcc gatccaactc      4980
ttctcgccat tgggacgaaa gctgtttcca ctctttcgca cttaacgtat gcccttcggg      5040
caacacgcca aacgcttcac caatggtcgc cagcggaatg ccaatacgct gagcaatttt      5100
gataattgca acatatcgca acacatcacg tttatatcgc cgctgattgc cgctgttacg      5160
gatactggta atcaaccctt tactttcata gaaatgcagc gccgataccg ccacaccgct      5220
gcgtttcgcc acttcgccgg gggttagcag cgctttaatg cggggtaatt tcttttccat      5280
aaatcgcttt acctcaagtt aacttgagga attatactcc ccaacagaty aattaacgaa      5340
ctgaacactg aaaagaggca gatttatgtc ccatcagaaa attattcagg atcttatcgc      5400
atggattgac gagcatattg accagccgta agcatgcaag gagaattaca tggtgagcaa      5460
gggcgaggag ctgttcaccg gggtggtgcc catcctggtc gagctggacg gcgacgtaaa      5520
cggccacaag ttcagcgtgt ccggcgaggg cgagggcgat gccacctacg gcaagctgac      5580
cctgaagttc atctgcacca ccggcaagct gcccgtgccc tggcccaccc tcgtgaccac      5640
cttcggctac ggcctgcagt gcttcgcccg ctacccgac cacatgaagc agcacgactt      5700
cttcaagtcc gccatgcccg aaggctacgt ccaggagcgc accatcttct tcaaggacga      5760
```

-continued

```
cggcaactac aagacccgcg ccgaggtgaa gttcgagggc gacaccctgg tgaaccgcat      5820
cgagctgaag ggcatcaact tcaaggagga cggcaacatc ctggggcaca agctggagta      5880
caactacaac agccacaacg tctatatcat ggccgacaag cagaagaacg gcatcaaggt      5940
gaacttcaag atccgccaca acatcgaggg cggcagcgtg cagctcgccg accactacca      6000
gcagaacacc cccatcggcg acggccccgt gctgctgccc gacaaccact acctgagcta      6060
ccagtccgcc ctgagcaaag accccaacga gaagcgcgat cacatggtcc tgctggagtt      6120
cgtgaccgcc gccgggatca ctctcggcat ggacgagctg tacaagtaat aaatcgatcc      6180
ggagcttatc gactgcacgg tgcaccaatg cttctggcgt caggcagcca tcggaagctg      6240
tggtatggct gtgcaggtcg taaatcactg cataattcgt gtcgctcaag gcgcactccc      6300
gttctggata atgttttttg cgccgacatc ataacggttc tggcaaatat tctgaaatga      6360
gctgttgaca attaatcatc ggctcgtata atgtgtggaa ttgtgagcgg ataacaattt      6420
cacacaggaa acagaa                                                     6436
```

```
                                                            SEQ. ID. No. 15
ctggctacat caagacacca gcggttgatg                                        30

SEQ. ID. No. 16
cggcccctgg taggtcatca accgctggtg                                        30

SEQ. ID. No. 17
ttcatgtcta accgtttgga tcgtaaggta gcaatcatta caggtggtac gttgggtatc       60
ggtttagcta tcgccacgaa gttcgttgaa gaaggggcta aggtcatgat taccggccgg      120
cacagcgatg ttggtgaaaa agcagctaag agtgtcggca ctcctgatca gattcaattt      180
ttccaacatg attcttccga tgaagacggc tggacgaaat tattcgatgc aacggaaaaa      240
gcctttggcc cagtttctac attagttaat aacgctggga tcgcggttaa caagagtgtc      300
gaagaaacca cgactgctga atggcgtaaa ttattagccg tcaaccttga tggtgtcttc      360
ttcggtaccc gattagggat tcaacgatg aagaacaaag cttaggggc ttccatcatc       420 aacatgtctt cgatcgaagg cttgtgggt gatcctagct taggggctta caacgcatct      480
aaaggggccg tacggattat gtccaagtca gctgccttag attgtgccct aaaggactac      540
gatgttcggg taaacactgt tcaccctggc tacatcaaga caccagcggt tgatgaccta      600
ccaggggccg aagaagcgat gtcacaacgg accaagacgc caatgggcca tatcggtgaa      660
cctaacgata ttgcctacat ctgtgtttac ttggcttcta acgaatctaa atttgcaacg      720
ggttctgaat ttgtagttga cggtggctac actgctcaat agtaagcttc tgttttggcg      780
gatgagagaa gattttcagc ctgatacaga ttaaatcaga acgcagaagc ggtctgataa      840
aacagaattt gcctggcggc agtagcgcgg tggtcccacc tgaccccatg ccgaactcag      900
aagtgaaacg ccgtagcgcc gatggtagtg tggggtctcc ccatgcgaga gtagggaact      960
gccaggcatc aaataaaacg aaaggctcag tcgaaagact gggcctttcg ttttatctgt     1020
tgtttgtcgg tgaacgctct cctgagtagg acaaatccgc cgggagcgga tttgaacgtt     1080
gcgaagcaac ggcccggagg gtggcgggca ggacgcccgc cataaactgc caggcatcaa     1140
attaagcaga aggccatcct gacgatggcc ttttttgcgt ttctacaaac tctttttgttt    1200 atttttctaa atacattcaa atatgtatcc gctcatgaga caataaccct gataaatgct     1260
tcaataatat tgaaaaagga agagtatgag tattcaacat ttccgtgtcg cccttattcc     1320
cttttttgcg gcattttgcc ttcctgtttt tgctcaccca gaaacgctgg tgaaagtaaa     1380
agatgctgaa gatcagttgg gtgcacgagt gggttacatc gaactggatc tcaacagcgg     1440
taagatcctt gagagttttc gccccgaaga acgttttcca atgatgagca ctttttaaagt   1500
```

```
tctgctatgt ggcgcggtat tatcccgtgt tgacgccggg caagagcaac tcggtcgccg      1560
catacactat tctcagaatg acttggttga gtactcacca gtcacagaaa agcatcttac      1620
ggatggcatg acagtaagag aattatgcag tgctgccata accatgagtg ataacactgc      1680
ggccaactta cttctgacaa cgatcggagg accgaaggag ctaaccgctt ttttgcacaa      1740
catgggggat catgtaactc gccttgatcg ttgggaaccg gagctgaatg aagccatacc      1800
aaacgacgag cgtgacacca cgatgcctgt agcaatggca acaacgttgc gcaaactatt      1860
aactggcgaa ctacttactc tagcttcccg gcaacaatta atagactgga tggaggcgga      1920
taaagttgca ggaccacttc tgcgctcggc ccttccggct ggctggttta ttgctgataa      1980
atctggagcc ggtgagcgtg ggtctcgcgg tatcattgca gcactggggc cagatggtaa      2040
gccctcccgt atcgtagtta tctacacgac ggggagtcag gcaactatgg atgaacgaaa      2100
tagacagatc gctgagatag gtgcctcact gattaagcat tcgtaactgt cagaccaagt      2160
ttactcatat atactttaga ttgatttaaa acttcatttt taatttaaaa ggatctaggt      2220
gaagatcctt tttgataatc tcatgaccaa aatcccttaa cgtgagtttt cgttccactg      2280
agcgtcagac cccgtagaaa agatcaaagg atcttcttga gatccttttt ttctgcgcgt      2340
aatctgctgc ttgcaaacaa aaaaaccacc gctaccagcg gtggtttgtt tgccggatca      2400
agagctacca actctttttc cgaaggtaac tcgcttcagc agagcgcaga taccaaatac      2460
tgtccttcta gtgtagccgt agttaggcca ccacttcaag aactctgtag caccgcctac      2520
atacctcgct ctgctaatcc tgttaccagt ggctgctgcc agtggcgata agtcgtgtct      2580
taccgggttg gactcaagac gatagttacc ggataaggcg cagcggtcgg gctgaacggg      2640
gggttcgtgc acacagccca gcttggagcg aacgacctac accgaactga gatacctaca      2700
gcgtgagcta tgagaaagcg ccacgcttcc cgaagggaga aaggcggaca ggtatccggt      2760
aagcggcagg gtcggaacag gagagcgcac gagggagctt ccagggggaa acgcctggta      2820
tctttatagt cctgtcgggt ttcgccacct ctgacttgag cgtcgatttt tgtgatgctc      2880 gtcaggggggg cggagcctat ggaaaaacgc cagcaacgcg gccttttttac ggttcctggc      2940 cttttgctgg ccttttgctc acatgttctt tcctgcgtta tcccctgatt ctgtggataa      3000
ccgtattacc gcctttgagt gagctgatac cgctcgccgc agccgaacga ccgagcgcag      3060
cgagtcagtg agcgaggaag cggaagagcg cctgatgcgg tatttctcc ttacgcatct      3120 gtgcggtatt tcacaccgca tatggtgcac tctcagtaca atctgctctg atgccgcata      3180
gttaagccag tatacactcc gctatcgcta cgtgactggg tcatggctgc gccccgacac      3240
ccgccaacac ccgctgacgc gccctgacgg gcttgtctgc tcccggcatc cgcttacaga      3300
caagctgtga ccgtctccgg gagctgcatg tgtcagaggt tttcaccgtc atcaccgaaa      3360
cgcgcgaggc agctgcggta agctcatca gcgtggtcgt gaagcgattc acagatgtct      3420
gcctgttcat ccgcgtccag ctcgttgagt ttctccagaa gcgttaatgt ctggcttctg      3480
ataaagcggg ccatgttaag gcggttttt tcctgtttgg tcacttgatg cctccgtgta      3540
agggggaatt tctgttcatg ggggtaatga taccgatgaa acgagagagg atgctcacga      3600
tacgggttac tgatgatgaa catgcccggt tactggaacg ttgtgagggt aaacaactgg      3660
cggtatggat gcggcgggac cagagaaaaa tcactcaggg tcaatgccag cgcttcgtta      3720
atacagatgt aggtgttcca cagggtagcc agcagcatcc tgcgatgcag atccggaaca      3780
taatggtgca gggcgctgac ttccgcgttt ccagacttta cgaaacacgg aaaccgaaga      3840
ccattcatgt tgttgctcag gtcgcagacg ttttgcagca gcagtcgctt cacgttcgct      3900
cgcgtatcgg tgattcattc tgctaaccag taaggcaacc ccgccagcct agccgggtcc      3960
```

```
tcaacgacag gagcacgatc atgcgcaccc gtggccagga cccaacgctg cccgagatgc      4020
gccgcgtgcg gctgctggag atggcggacg cgatggatat gttctgccaa gggttggttt      4080
gcgcattcac agttctccgc aagaattgat tggctccaat tcttggagtg gtgaatccgt      4140
tagcgaggtg ccgccggctt ccattcaggt cgaggtggcc cggctccatg caccgcgacg      4200
caacgcgggg aggcagacaa ggtatagggc ggcgcctaca atccatgcca acccgttcca      4260
tgtgctcgcc gaggcggcat aaatcgccgt gacgatcagc ggtccagtga tcgaagttag      4320
gctggtaaga gccgcgagcg atccttgaag ctgtccctga tggtcgtcat ctacctgcct      4380
ggacagcatg gcctgcaacg cgggcatccc gatgccgccg aagcgagaa gaatcataat      4440 ggggaaggcc atccagcctc gcgtcgcgaa cgccagcaag acgtagccca gcgcgtcggc      4500
cgccatgccg gcgataatgg cctgcttctc gccgaaacgt ttggtggcgg gaccagtgac      4560
gaaggcttga gcgagggcgt gcaagattcc gaataccgca agcgacaggc cgatcatcgt      4620
cgcgctccag cgaaagcggt cctcgccgaa aatgacccag agcgctgccg gcacctgtcc      4680
tacgagttgc atgataaaga agacagtcat aagtgcggcg acgatagtca tgccccgcgc      4740
ccaccggaag gagctgactg ggttgaaggc tctcaagggc atcggtcgac caaactaaag      4800
cgcccttgtg gcgctttagt tttgttcatc ttccagcaag cgtgcgccgg taccttcttc      4860
tcctaagcgg tcgcccgggt tacgcaacgg gcaatcactg cgcgaaaggc agccacaacc      4920
aatacatccg tccagttcgt cacgcagcgc cactaaggta tgaatgcgcc gatccaactc      4980
ttctcgccat tgggacgaaa gctgtttcca ctctttcgca cttaacgtat gcccttcggg      5040
caacacgcca aacgcttcac caatggtcgc cagcggaatg ccaatacgct gagcaatttt      5100
gataattgca acatatcgca acacatcacg tttatatcgc cgctgattgc cgctgttacg      5160
gatactggta atcaacccctt tactttcata gaaatgcagc gccgataccg ccacaccgct      5220
gcgtttcgcc acttcgccgg gggttagcag cgctttaatg cggggtaatt tcttttccat      5280
aaatcgcttt acctcaagtt aacttgagga attatactcc ccaacagaty aattaacgaa      5340
ctgaacactg aaaagaggca gatttatgtc ccatcagaaa attattcagg atcttatcgc      5400
atggattgac gagcatattg accagccgta agcatgcaag gagaattaca tggtgagcaa      5460
gggcgaggag ctgttcaccg gggtggtgcc catcctggtc gagctggacg gcgacgtaaa      5520
cggccacaag ttcagcgtgt ccggcgaggg cgagggcgat gccacctacg gcaagctgac      5580
cctgaagttc atctgcacca ccggcaagct gcccgtgccc tggcccaccc tcgtgaccac      5640
cttcggctac ggcctgcagt gcttcgcccg ctaccccgac cacatgaagc agcacgactt      5700
cttcaagtcc gccatgcccg aaggctacgt ccaggagcgc accatcttct tcaaggacga      5760
cggcaactac aagacccgcg ccgaggtgaa gttcgagggc gacaccctgg tgaaccgcat      5820
cgagctgaag ggcatcaact tcaaggagga cggcaacatc ctggggcaca agctggagta      5880
caactacaac agccacaacg tctatatcat ggccgacaag cagaagaacg gcatcaaggt      5940
gaacttcaag atccgccaca acatcgaggg cggcagcgtg cagctcgccg accactacca      6000
gcagaacacc cccatcggcg acggccccgt gctgctgccc gacaaccact acctgagcta      6060
ccagtccgcc ctgagcaaag accccaacga gaagcgcgat cacatggtcc tgctggagtt      6120
cgtgaccgcc gccgggatca ctctcggcat ggacgagctg tacaagtaat aaatcgatcc      6180
ggagcttatc gactgcacgg tgcaccaatg cttctggcgt caggcagcca tcggaagctg      6240
tggtatggct gtgcaggtcg taaatcactg cataattcgt gtcgctcaag gcgcactccc      6300
gttctggata atgttttttg cgccgacatc ataacggttc tggcaaatat tctgaaatga      6360
```

-continued

| | |
|---|---|
| gctgttgaca attaatcatc ggctcgtata atgtgtggaa ttgtgagcgg ataacaattt | 6420 |
| cacacaggaa acagaa | 6436 |

SEQ. ID. No. 18

| | |
|---|---|
| acaagaattc gctaagagtg tcggcactcc | 30 |

SEQ. ID. No. 19

| | |
|---|---|
| ggccaagctt ccgaagaaga caccatcaag | 30 |

SEQ. ID. No. 20

| | |
|---|---|
| ttcatgtcta accgtttgga tggtaaggta gcaatcatta caggtggtac gttgggtatc | 60 |
| ggtttagcta tcgccacgaa gttcgttgaa gaaggggcta aggtcatgat taccggccgg | 120 |
| cacagcgatg ttggtgaaaa agcagctaag agtgtcggca ctcctgatca gattcaattt | 180 |
| ttccaacatg attcttccga tgaagacggc tggacgaaat tattcgatgc aacggaaaaa | 240 |
| gcctttggcc cagtttctac attagttaat aacgctggga tcatggttaa caagagtgtc | 300 |
| gaagaaacca cgactgctga atggcgtaaa ttattagccg tcaaccttga tggtgtcttc | 360 |
| ttcggtaccc gattagggat tcaacggatg aagaacaaag cttagggggc ttccatcatc | 420 |
| aacatgtctt cgatcgaagg ctttgtgggt gatcctagct taggggctta caacgcatct | 480 |
| aaaggggccg tacggattat gtccaagtca gctgccttag attgtgccct aaaggactac | 540 |
| gatgttcggg taaacactgt tcaccctggc tacatcaaga caccattggt tgatgaccta | 600 |
| ccaggggccg aagaagcgat gtcacaacgg accaagacgc caatgggcca tatcggtgaa | 660 |
| cctaacgata ttgcctacat ctgtgtttac ttggcttcta cgaatctaa atttgcaacg | 720 |
| ggttctgaat tgtagttga cggtggctac actgctcaat agtaagcttc tgttttggcg | 780 |
| gatgagagaa gattttcagc ctgatacaga ttaaatcaga acgcagaagc ggtctgataa | 840 |
| aacagaattt gcctggcggc agtagcgcgg tggtcccacc tgaccccatg ccgaactcag | 900 |
| aagtgaaacg ccgtagcgcc gatggtagtg tggggtctcc ccatgcgaga gtagggaact | 960 |
| gccaggcatc aaataaaacg aaaggctcag tcgaaagact gggcctttcg ttttatctgt | 1020 |
| tgtttgtcgg tgaacgctct cctgagtagg acaaatccgc cgggagcgga tttgaacgtt | 1080 |
| gcgaagcaac ggcccggagg gtggcgggca ggacgcccgc cataaactgc caggcatcaa | 1140 |
| attaagcaga aggccatcct gacggatggc ctttttgcgt ttctacaaac tcttttgttt | 1200 |
| attttctaa atacattcaa atatgtatcc gctcatgaga caataaccct gataaatgct | 1260 |
| tcaataatat tgaaaaagga agagtatgag tattcaacat ttccgtgtcg cccttattcc | 1320 |
| cttttttgcg gcattttgcc ttcctgtttt tgctcaccca gaaacgctgg tgaaagtaaa | 1380 |
| agatgctgaa gatcagttgg gtgcacgagt gggttacatc gaactggatc tcaacagcgg | 1440 |
| taagatcctt gagagttttc gccccgaaga acgttttcca atgatgagca cttttaaagt | 1500 |
| tctgctatgt ggcgcggtat tatcccgtgt tgacgccggg caagagcaac tcggtcgccg | 1560 |
| catacactat tctcagaatg acttggttga gtactcacca gtcacagaaa agcatcttac | 1620 |
| ggatggcatg acagtaagag aattatgcag tgctgccata accatgagtg ataacactgc | 1680 |
| ggccaactta cttctgacaa cgatcggagg accgaaggag ctaaccgctt ttttgcacaa | 1740 |
| catgggggat catgtaactc gccttgatcg ttgggaaccg gagctgaatg aagccatacc | 1800 |
| aaacgacgag cgtgacacca cgatgcctgt agcaatggca acaacgttgc gcaaactatt | 1860 |
| aactggcgaa ctacttactc tagcttcccg gcaacaatta atagactgga tggaggcgga | 1920 |
| taaagttgca ggaccacttc tgcgctcggc ccttccggct ggctggttta ttgctgataa | 1980 |
| atctggagcc ggtgagcgtg ggtctcgcgg tatcattgca gcactggggc cagatggtaa | 2040 |
| gccctcccgt atcgtagtta tctacacgac ggggagtcag gcaactatgg atgaacgaaa | 2100 |

```
                                    -continued
tagacagatc gctgagatag gtgcctcact gattaagcat tcgtaactgt cagaccaagt    2160
ttactcatat atactttaga ttgatttaaa acttcatttt taatttaaaa ggatctaggt    2220
gaagatcctt tttgataatc tcatgaccaa aatcccttaa cgtgagtttt cgttccactg    2280
agcgtcagac cccgtagaaa agatcaaagg atcttcttga gatcctttt ttctgcgcgt     2340 aatctgctgc ttgcaaacaa aaaaaccacc gctaccagcg gtggtttgtt tgccggatca    2400
agagctacca actctttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata agtcgtgtct    2580
taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccagggggaa acgcctggta    2820
tctttatagt cctgtcgggt ttcgccacct ctgacttgag cgtcgatttt tgtgatgctc    2880 gtcaggggg cggagcctat ggaaaaacgc cagcaacgcg gcctttttac ggttcctggc     2940
cttttgctgg ccttttgctc acatgttctt tcctgcgtta tcccctgatt ctgtggataa    3000
ccgtattacc gcctttgagt gagctgatac cgctcgccgc agccgaacga ccgagcgcag    3060
cgagtcagtg agcgaggaag cggaagagcg cctgatgcgg tattttctcc ttacgcatct    3120
gtgcggtatt tcacaccgca tatggtgcac tctcagtaca atctgctctg atgccgcata    3180
gttaagccag tatacactcc gctatcgcta cgtgactggg tcatggctgc gccccgacac    3240
ccgccaacac ccgctgacgc gccctgacgg gcttgtctgc tcccggcatc cgcttacaga    3300
caagctgtga ccgtctccgg gagctgcatg tgtcagaggt tttcaccgtc atcaccgaaa    3360
cgcgcgaggc agctgcggta aagctcatca gcgtggtcgt gaagcgattc acagatgtct    3420
gcctgttcat ccgcgtccag ctcgttgagt ttctccagaa gcgttaatgt ctggcttctg    3480
ataaagcggg ccatgttaag gcggtttttt cctgtttgg tcacttgatg cctccgtgta     3540
agggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tygctccaat tcttggagtg gtgaatccgt    4140
tagcgaggtg ccgccggctt ccattcaggt cgaggtggcc cggctccatg caccgcgacg    4200
caacgcgggg aggcagacaa ggtatagggc ggcgcctaca atccatgcca acccgttcca    4260
tgtgctcgcc gaggcggcat aaatcgccgt gacgatcagc ggtccagtga tcgaagttag    4320
gctggtaaga gccgcgagcg atccttgaag ctgtccctga tggtcgtcat ctacctgcct    4380
ggacagcatg gcctgcaacg cgggcatccc gatgccgccg gaagcgagaa gaatcataat    4440
ggggaaggcc atccagcctc gcgtcgcgaa cgccagcaag acgtagccca gcgcgtcggc    4500
cgccatgccg gcgataatgg cctgcttctc gccgaaacgt ttggtggcgg gaccagtgac    4560
```

-continued

```
gaaggcttga gcgagggcgt gcaagattcc gaataccgca agcgacaggc cgatcatcgt      4620
cgcgctccag cgaaagcggt cctcgccgaa aatgacccag agcgctgccg gcacctgtcc      4680
tacgagttgc atgataaaga agacagtcat aagtgcggcg acgatagtca tgccccgcgc      4740
ccaccggaag gagctgactg ggttgaaggc tctcaagggc atcggtcgac caaactaaag      4800
cgcccttgtg gcgctttagt tttgttcatc ttccagcaag cgtgcgccgg taccttcttc      4860
tcctaagcgg tcgcccgggt tacgcaacgg gcaatcactg cgcgaaaggc agccacaacc      4920
aatacatccg tccagttcgt cacgcagcgc cactaaggta tgaatgcgcc gatccaactc      4980
ttctcgccat tgggacgaaa gctgtttcca ctctttcgca cttaacgtat gcccttcggg      5040
caacacgcca aacgcttcac caatggtcgc cagcggaatg ccaatacgct gagcaatttt      5100
gataattgca acatatcgca acacatcacg tttatatcgc cgctgattgc cgctgttacg      5160
gatactggta atcaacccct tactttcata gaaatgcagc gccgataccg ccacaccgct      5220
gcgtttcgcc acttcgccgg gggttagcag cgctttaatg cggggtaatt tcttttccat      5280
aaatcgcttt acctcaagtt aacttgagga attatactcc ccaacagaty aattaacgaa      5340
ctgaacactg aaaagaggca gatttatgtc ccatcagaaa attattcagg atcttatcgc      5400
atggattgac gagcatattg accagccgta agcatgcaag gagaattaca tggtgagcaa      5460
gggcgaggag ctgttcaccg gggtggtgcc catcctggtc gagctggacg gcgacgtaaa      5520
cggccacaag ttcagcgtgt ccggcgaggg cgagggcgat gccacctacg gcaagctgac      5580
cctgaagttc atctgcacca ccggcaagct gcccgtgccc tggcccaccc tcgtgaccac      5640
cttcggctac ggcctgcagt gcttcgcccg ctaccccgac cacatgaagc agcacgactt      5700
cttcaagtcc gccatgcccg aaggctacgt ccaggagcgc accatcttct tcaaggacga      5760
cggcaactac aagacccgcg ccgaggtgaa gttcgagggc gacaccctgg tgaaccgcat      5820
cgagctgaag ggcatcaact tcaaggagga cggcaacatc ctggggcaca gctggagta      5880 caactacaac agccacaacg tctatatcat ggccgacaag cagaagaacg gcatcaaggt      5940
gaacttcaag atccgccaca acatcgaggg cggcagcgtg cagctcgccg accactacca      6000
gcagaacacc cccatcggcg acggccccgt gctgctgccc gacaaccact acctgagcta      6060
ccagtccgcc ctgagcaaag accccaacga gaagcgcgat cacatggtcc tgctggagtt      6120
cgtgaccgcc gccgggatca ctctcggcat ggacgagctg tacaagtaat aaatcgatcc      6180
ggagcttatc gactgcacgg tgcaccaatg cttctggcgt caggcagcca tcggaagctg      6240
tggtatggct gtgcaggtcg taaatcactg cataattcgt gtcgctcaag gcgcactccc      6300
gttctggata atgttttttg cgccgacatc ataacggttc tggcaaatat tctgaaatga      6360
gctgttgaca attaatcatc ggctcgtata atgtgtggaa ttgtgagcgg ataacaattt      6420
cacacaggaa acagaa                                                     6436
```

```
                                                          SEQ. ID. NO. 21
atctgcatgc cggctggtca atatgctcgt c                                  31

SEQ. ID. No. 22
gctagtcgac caaactaaag cgcccttgtg                                    30

SEQ. ID. No. 23
agaggcatgc gtgagcaagg gcgagg                                        26

SEQ. ID. No. 24
gcgcatcgat ttattacttg tacagctcgt ccatg                              35

SEQ. ID. NO. 25
ttcatgtcta accgtttgga tggtaaggta gcaatcatta caggtggtac gttgggtatc    60
ggtttagcta tcgccacgaa gttcgttgaa gaagggcta aggtcatgat taccggccgg    120
```

-continued

```
cacagcgatg ttggtgaaaa agcagctaag agtgtcggca ctcctgatca gattcaattt      180
ttccaacatg attcttccga tgaagacggc tggacgaaat tattcgatgc aacggaaaaa      240
gcctttggcc cagtttctac attagttaat aacgctggga tcgcggttaa caagagtgtc      300
gaagaaacca cgactgctga atggcgtaaa ttattagccg tcaaccttga tggtgtcttc      360
ttcggtaccc gattagggat tcaacggatg aagaacaaag cttaggggc ttccatcatc       420 aacatgtctt cgatcgaagg ctttgtgggt gatcctagct tagggcgtta caacgcatct      480 aaagggccg tacggattat gtccaagtca gctgccttag attgtgccct aaaggactac       540
gatgttcggg taaacactgt tcaccctggc tacatcaaga caccattggt tgatgaccta      600 ccagggccg aagaagcgat gtcacaacgg accaagacgc caatgggcca tatcggtgaa       660
cctaacgata ttgcctacat ctgtgtttac ttggcttcta acgaatctaa atttgcaacg      720
ggttctgaat ttgtagttga cggtggctac actgctcaat agtaagcttc tgttttggcg      780
gatgagagaa gattttcagc ctgatacaga ttaaatcaga acgcagaagc ggtctgataa      840
aacagaattt gcctggcggc agtagcgcgg tggtcccacc tgaccccatg ccgaactcag      900
aagtgaaacg ccgtagcgcc gatggtagtg tggggtctcc ccatgcgaga gtagggaact      960
gccaggcatc aaataaaacg aaaggctcag tcgaaagact gggcctttcg ttttatctgt     1020
tgtttgtcgg tgaacgctct cctgagtagg acaaatccgc cgggagcgga tttgaacgtt     1080
gcgaagcaac ggcccggagg gtggcgggca ggacgcccgc cataaactgc caggcatcaa     1140
attaagcaga aggccatcct gacggatggc cttttgcgt ttctacaaac tcttttgttt      1200
atttttctaa atacattcaa atatgtatcc gctcatgaga caataaccct gataaatgct     1260
tcaataatat tgaaaagga agagtatgag tattcaacat ttccgtgtcg cccttattcc      1320
cttttttgcg gcattttgcc ttcctgtttt tgctcaccca gaaacgctgg tgaaagtaaa     1380
agatgctgaa gatcagttgg gtgcacgagt gggttacatc gaactggatc tcaacagcgg     1440
taagatcctt gagagttttc gccccgaaga acgttttcca atgatgagca cttttaaagt     1500
tctgctatgt ggcgcggtat tatcccgtgt tgacgccggg caagagcaac tcggtcgccg     1560
catacactat tctcagaatg acttggttga gtactcacca gtcacagaaa agcatcttac     1620
ggatggcatg acagtaagag aattatgcag tgctgccata accatgagtg ataacactgc     1680
ggccaactta cttctgacaa cgatcggagg accgaaggag ctaaccgctt ttttgcacaa     1740
catgggggat catgtaactc gccttgatcg ttgggaaccg gagctgaatg aagccatacc     1800
aaacgacgag cgtgacacca cgatgcctgt agcaatggca acaacgttgc gcaaactatt     1860
aactggcgaa ctacttactc tagcttcccg gcaacaatta atagactgga tggaggcgga     1920
taaagttgca ggaccacttc tgcgctcggc ccttccggct ggctggttta ttgctgataa     1980
atctggagcc ggtgagcgtg ggtctcgcgg tatcattgca gcactggggc cagatggtaa     2040
gccctcccgt atcgtagtta tctacacgac ggggagtcag gcaactatgg atgaacgaaa     2100
tagacagatc gctgagatag gtgcctcact gattaagcat tcgtaactgt cagaccaagt     2160
ttactcatat atactttaga ttgatttaaa acttcatttt taatttaaaa ggatctaggt     2220
gaagatcctt tttgataatc tcatgaccaa atcccttaa cgtgagtttt cgttccactg      2280
agcgtcagac cccgtagaaa agatcaaagg atcttcttga tccttttt ttctgcgcgt       2340 aatctgctgc ttgcaaacaa aaaaaccacc gctaccagcg gtggtttgtt tgccggatca     2400
agagctacca actctttttc cgaaggtaac tggcttcagc agagcgcaga taccaaatac     2460
tgtccttcta gtgtagccgt agttaggcca ccacttcaag aactctgtag caccgcctac     2520
```

```
                                        -continued
atacctcgct ctgctaatcc tgttaccagt ggctgctgcc agtggcgata agtcgtgtct      2580 taccggggttg gactcaagac gatagttacc ggataaggcg cagcggtcgg gctgaacggg     2640
gggttcgtgc acacagccca gcttggagcg aacgacctac accgaactga gatacctaca     2700
gcgtgagcta tgagaaagcg ccacgcttcc cgaagggaga aaggcggaca ggtatccggt     2760
aagcggcagg gtcggaacag gagagcgcac gagggagctt ccagggggaa acgcctggta     2820
tctttatagt cctgtcgggt ttcgccacct ctgacttgag cgtcgatttt tgtgatgctc     2880
gtcagggggg cggagcctat ggaaaaacgc cagcaacgcg gcctttttac ggttcctggc     2940
cttttgctgg ccttttgctc acatgttctt tcctgcgtta tcccctgatt ctgtggataa     3000
ccgtattacc gcctttgagt gagctgatac cgctcgccgc agccgaacga ccgagcgcag     3060
cgagtcagtg agcgaggaag cggaagagcg cctgatgcgg tattttctcc ttacgcatct     3120
gtgcggtatt tcacaccgca tatggtgcac tctcagtaca atctgctctg atgccgcata     3180
gttaagccag tatacactcc gctatcgcta cgtgactggg tcatggctgc gccccgacac     3240
ccgccaacac ccgctgacgc gccctgacgg gcttgtctgc tcccggcatc cgcttacaga     3300
caagctgtga ccgtctccgg gagctgcatg tgtcagaggt tttcaccgtc atcaccgaaa     3360
cgcgcgaggc agctgcggta agctcatca gcgtggtcgt gaagcgattc acagatgtct     3420
gcctgttcat ccgcgtccag ctcgttgagt ttctccagaa gcgttaatgt ctggcttctg     3480
ataaagcggg ccatgttaag gcggtttttt cctgtttggg tcacttgatg cctccgtgta     3540
agggggaatt tctgttcatg ggggtaatga taccgatgaa acgagagagg atgctcacga     3600
tacgggttac tgatgatgaa catgcccggt tactggaacg ttgtgagggt aaacaactgg     3660
cggtatggat gcggcgggac cagagaaaaa tcactcaggg tcaatgccag cgcttcgtta     3720
atacagatgt aggtgttcca cagggtagcc agcagcatcc tgcgatgcag atccggaaca     3780
taatggtgca gggcgctgac ttccgcgttt ccagacttta cgaaacacgg aaaccgaaga     3840
ccattcatgt tgttgctcag gtcgcagacg ttttgcagca gcagtcgctt cacgttcgct     3900
cgcgtatcgg tgattcattc tgctaaccag taaggcaacc ccgccagcct agccgggtcc     3960
tcaacgacag gagcacgatc atgcgcaccc gtggccagga cccaacgctg cccgagatgc     4020
gccgcgtgcg gctgctggag atggcggacg cgatggatat gttctgccaa gggttggttt     4080
gcgcattcac agttctccgc aagaattgat tggctccaat tcttggagtg gtgaatccgt     4140
tagcgaggtg ccgccggctt ccattcaggt cgaggtggcc cggctccatg caccgcgacg     4200
caacgcgggg aggcagacaa ggtatagggc ggcgcctaca atccatgcca acccgttcca     4260
tgtgctcgcc gaggcggcat aaatcgccgt gacgatcagc ggtccagtga tcgaagttag     4320
gctggtaaga gccgcgagcg atccttgaag ctgtccctga tggtcgtcat ctacctgcct     4380
ggacagcatg gcctgcaacg cgggcatccc gatgccgccg gaagcgagaa gaatcataat     4440
ggggaaggcc atccagcctc gcgtcgcgaa cgccagcaag acgtagccca gcgcgtcggc     4500
cgccatgccg gcgataatgg cctgcttctc gccgaaacgt ttggtggcgg gaccagtgac     4560
gaaggcttga gcgagggcgt gcaagattcc gaataccgca agcgacaggc cgatcatcgt     4620
cgcgctccag cgaaagcggt cctcgccgaa aatgacccag agcgctgccg gcacctgtcc     4680
tacgagttgc atgataaaga agacagtcat aagtgcggcg acgatagtca tgccccgcgc     4740
ccaccggaag gagctgactg ggttgaaggc tctcaagggc atcggtcgac caaactaaag     4800
cgcccttgtg gcgctttagt tttgttcatc ttccagcaag cgtgcgccgg taccttcttc     4860
tcctaagcgc tcgcccgggt tacgcaacgg gcaatcactg cgcgaaaggc agccacaacc     4920
aatacatccg tccagttcgt cacgcagcgc cactaaggta tgaatgcgcc gatccaactc     4980
```

-continued

```
ttctcgccat tgggacgaaa gctgtttcca ctctttcgca cttaacgtat gcccttcggg    5040
caacacgcca aacgcttcac caatggtcgc cagcggaatg ccaatacgct gagcaatttt    5100
gataattgca acatatcgca acacatcacg tttatatcgc cgctgattgc cgctgttacg    5160
gatactggta atcaaccctt tactttcata gaaatgcagc gccgataccg ccacaccgct    5220
gcgtttcgcc acttcgccgg gggttagcag cgctttaatg cggggtaatt tcttttccat    5280
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccggc atgcgtgagc aagggcgagg agctgttcac    5460
cggggtggtg cccatcctgg tcgagctgga cggcgacgta aacggccaca gttcagcgt     5520 gtccggcgag ggcgagggcg atgccaccta cggcaagctg accctgaagt tcatctgcac    5580
caccggcaag ctgcccgtgc cctggcccac cctcgtgacc accttcggct acggcctgca    5640
gtgcttcgcc cgctaccccg accacatgaa gcagcacgac ttcttcaagt ccgccatgcc    5700
cgaaggctac gtccaggagc gcaccatctt cttcaaggac gacggcaact acaagacccg    5760
cgccgaggtg aagttcgagg gcgacaccct ggtgaaccgc atcgagctga agggcatcaa    5820
cttcaaggag gacggcaaca tcctggggca caagctggag tacaactaca acagccacaa    5880
cgtctatatc atggccgaca gcagaagaa cggcatcaag gtgaacttca agatccgcca     5940
caacatcgag ggcggcagcg tgcagctcgc cgaccactac cagcagaaca ccccccatcgg   6000 cgacggcccc gtgctgctgc ccgacaacca ctacctgagc taccagtccg ccctgagcaa    6060
agaccccaac gagaagcgcg atcacatggt cctgctggag ttcgtgaccg ccgccgggat    6120
cactctcggc atggacgagc tgtacaagta ataaatcgat ccggagctta tcgactgcac    6180
ggtgcaccaa tgcttctggc gtcaggcagc catcggaagc tgtggtatgg ctgtgcaggt    6240
cgtaaatcac tgcataattc gtgtcgctca aggcgcactc ccgttctgga taatgttttt    6300
tgcgccgaca tcataacggt tctggcaaat attctgaaat gagctgttga caattaatca    6360
tcggctcgta taatgtgtgg aattgtgagc ggataacaat ttcacacagg aaacagaa      6418
```

---

The invention claimed is:

1. A method for isolating genes which code for NADP (H)-dependent enzymes, comprising the method steps:
   (I) providing an NADP(H) nanosensor comprising
      i) a first nucleic acid, the first nucleic acid having a nucleic acid sequence to which a regulator is capable of binding, wherein an oxidation state of the regulator depends on NADP(H) availability;
      ii) a second nucleic acid following the first nucleic acid i), the second nucleic acid having a promoter sequence to which an RNA polymerase is capable of binding, wherein an affinity of the RNA polymerase for the promoter sequence is influenced by the oxidation state of the regulator;
      iii) a third nucleic acid, the third nucleic acid having a nucleic acid sequence which is under the control of the second nucleic acid ii), the third nucleic acid having a nucleic acid sequence which codes for an autofluorescent protein;
   (II) introducing the NADP(H) nanosensor into a cell to form a cell suspension;
   (III) introducing a gene which may code for an NADP (H)-dependent enzyme into individual cells of the cell suspension obtained in method step (II);
   (IV) incubating the cells obtained in method step (III) with a substrate for the NADP(H)-dependent enzyme;
   (V) identifying individual cells in the cell suspension obtained in method step (IV) with an increased activity of NADP(H)-dependent enzymes by detection of intracellular fluorescence activity of the individual cells, wherein the presence of the NADP(H)-dependent enzyme in the individual cells increases expression and production of the autofluorescent protein, leading to the increased fluorescent activity;
   (VI) separating off the identified cells from the cell suspension;
   (VII) isolating the genes coding for an NADP(H)-dependent enzyme in the identified cells;
      wherein components i) and ii) are comprised in a nucleic acid having a nucleic acid sequence selected from the group consisting of:
      a) a nucleic acid sequence according to SEQ. ID. No. 01, and
      b) a nucleic acid sequence which has an identity of at least 99% to the nucleic acid sequence of a),
      wherein the regulator is SoxR regulator and the promoter sequence is a sequence of soxS promoter, the nucleic acid sequence of a) or b) being able to bind SoxR regulator such that the affinity of the RNA polymerase for the soxS promoter depends on the oxidation state of SoxR regulator.

2. The method according to claim 1, wherein the NADP (H) nanosensor further comprises
   an *E. coli* gene for SoxR (soxR); and
   optionally a nucleic acid having a part sequence of a soxS gene from *E. coli* following the soxR gene;
   wherein the components i) and ii), following the soxR gene, are an intergenic region from *E. coli*, which is located between soxR and soxS, and comprises a SoxR binding sequence, a soxS promoter sequence following the SoxR binding sequence and a nucleic acid following the soxS promoter sequence, which at a level of mRNA corresponds to a ribosome binding site; and
   wherein the component iii), following the soxR gene or the part of soxS gene, is under the control of the soxS promoter sequence.

3. The method according to claim 1, wherein the NADP (H) nanosensor further comprises
   an *E. coli* gene for SoxR (soxR); and
   a nucleic acid having a sequence or a part sequence of a soxS gene from *E. coli*, following the soxR gene and under the control of the soxS promoter;
   wherein the components i) and ii), following the soxR gene, are an intergenic region from *E. coli*, which is located between soxR and soxS, and comprises a SoxR binding sequence, a soxS promoter sequence following the SoxR binding sequence and a nucleic acid sequence following the soxS promoter sequence, which at a level of mRNA corresponds to a ribosome binding site; and
   wherein the component iii), following the nucleic acid sequence corresponding to the ribosome binding site in the components i) and ii), is under the control of the soxS promoter sequence, as component iii).

4. The method according to claim 3, wherein the soxR gene is selected from the group consisting of:
   a) a nucleic acid having the sequence according to SEQ. ID. No. 02, and
   b) a nucleic acid having a sequence coding for the polypeptide with the amino acid sequence according to SEQ. ID. No. 03.

5. The method according to claim 1, wherein the nucleic acid (iii) which codes for the autofluorescent protein is selected from the group consisting of the genes coding for green fluorescent protein (GFP), yellow fluorescent protein (YFP), blue fluorescent protein (BFP), cyan fluorescent protein (CFP), enhanced green fluorescent protein (EGFP), enhanced yellow fluorescent protein (EYFP), enhanced blue fluorescent protein (EBFP), enhanced cyan fluorescent protein (ECFP), red fluorescent protein (DsRed), far red fluorescent proteome (HcRed), *Anemonia sulcata* red fluorescent protein (AsRed), *Anemonia majano* cyan fluorescent protein (AmCyan), *Zoanthus* sp. green fluorescent protein (ZsGreen), *Aequorea coerulescens* green fluorescent protein (AcGFP) and *Zoanthus* sp. yellow fluorescent protein (ZsYellow).

6. The method according to claim 5, wherein the nucleic acid (iii) which codes for the autofluorescent protein is the gene coding for enhanced yellow fluorescent protein (EYFP).

7. The method according to claim 1, wherein the identified cells are separated off from the cell suspension in method step (VI) by flow cytometry.

8. The method according to claim 2, wherein the soxR gene is selected from the group consisting of:
   a) a nucleic acid having the sequence according to SEQ. ID. No. 02, and
   b) a nucleic acid having a sequence coding for the polypeptide with the amino acid sequence according to SEQ. ID. No. 03.

* * * * *

SEQUENCE LISTING

```
<160> NUMBER OF SEQ ID NOS: 25

<210> SEQ ID NO 1
<211> LENGTH: 85
<212> TYPE: DNA
<213> ORGANISM: E. coli

<400> SEQUENCE: 1
aaatctgcct cttttcagtg ttcagttcgt taattcatct gttggggagt ataattcctc    60
aagttaactt gaggtaaagc gattt                                          85

<210> SEQ ID NO 2
<211> LENGTH: 465
<212> TYPE: DNA
<213> ORGANISM: E. coli

<400> SEQUENCE: 2
atggaaaaga aattacccccg cattaaagcg ctgctaaccc ccggcgaagt ggcgaaacgc    60
agcggtgtgg cggtatcggc gctgcatttc tatgaaagta aagggttgat taccagtatc    120
cgtaacagcg gcaatcagcg gcgatataaa cgtgatgtgt tgcgatatgt tgcaattatc    180
```

```
aaaattgctc agcgtattgg cattccgctg gcgaccattg gtgaagcgtt tggcgtgttg    240
cccgaagggc atacgttaag tgcgaaagag tggaaacagc tttcgtccca atggcgagaa    300
gagttggatc ggcgcattca taccttagtg gcgctgcgtg acgaactgga cggatgtatt    360
ggttgtggct gcctttcgcg cagtgattgc ccgttgcgta acccgggcga ccgcttagga    420
gaagaaggta ccggcgcacg cttgctggaa gatgaacaaa actaa                     465
```

```
<210> SEQ ID NO 3
<211> LENGTH: 154
<212> TYPE: PRT
<213> ORGANISM: E. coli

<400> SEQUENCE: 3
```

```
Met Glu Lys Lys Leu Pro Arg Ile Lys Ala Leu Leu Thr Pro Gly Glu
1               5                   10                  15

Val Ala Lys Arg Ser Gly Val Ala Val Ser Ala Leu His Phe Tyr Glu
            20                  25                  30

Ser Lys Gly Leu Ile Thr Ser Ile Arg Asn Ser Gly Asn Gln Arg Arg
        35                  40                  45

Tyr Lys Arg Asp Val Leu Arg Tyr Val Ala Ile Ile Lys Ile Ala Gln
    50                  55                  60

Arg Ile Gly Ile Pro Leu Ala Thr Ile Gly Glu Ala Phe Gly Val Leu
65                  70                  75                  80

Pro Glu Gly His Thr Leu Ser Ala Lys Glu Trp Lys Gln Leu Ser Ser
                85                  90                  95

Gln Trp Arg Glu Glu Leu Asp Arg Arg Ile His Thr Leu Val Ala Leu
            100                 105                 110

Arg Asp Glu Leu Asp Gly Cys Ile Gly Cys Gly Cys Leu Ser Arg Ser
        115                 120                 125

Asp Cys Pro Leu Arg Asn Pro Gly Asp Arg Leu Gly Glu Glu Gly Thr
    130                 135                 140

Gly Ala Arg Leu Leu Glu Asp Glu Gln Asn
145                 150
```

```
<210> SEQ ID NO 4
<211> LENGTH: 34
<212> TYPE: DNA
<213> ORGANISM: Artificial Sequence
<220> FEATURE:
<223> OTHER INFORMATION: SoxS_for_SphI

<400> SEQUENCE: 4
atctgcatgc ttacggctgg tcaatatgct cgtc                                34
```

```
<210> SEQ ID NO 5
<211> LENGTH: 30
<212> TYPE: DNA
<213> ORGANISM: Artificial Sequence
<220> FEATURE:
<223> OTHER INFORMATION: SoxR_rev_SalI

<400> SEQUENCE: 5
gctagtcgac caaactaaag cgcccttgtg                                     30
```

```
<210> SEQ ID NO 6
<211> LENGTH: 41
<212> TYPE: DNA
<213> ORGANISM: Artificial Sequence
<220> FEATURE:
```

<223> OTHER INFORMATION: EYFP_for_SphI

<400> SEQUENCE: 6
agaggcatgc aaggagaatt acatggtgag caagggcgag g         41

<210> SEQ ID NO 7
<211> LENGTH: 35
<212> TYPE: DNA
<213> ORGANISM: Artificial Sequence
<220> FEATURE:
<223> OTHER INFORMATION: EYFP_rev_ClaI

<400> SEQUENCE: 7
gcgcatcgat ttattacttg tacagctcgt ccatg         35

<210> SEQ ID NO 8
<211> LENGTH: 6436
<212> TYPE: DNA
<213> ORGANISM: Artificial Sequenz
<220> FEATURE:
<223> OTHER INFORMATION: pSenSox

<400> SEQUENCE: 8

| | | | | | |
|---|---|---|---|---|---|
| ttcatgtcta | accgtttgga | tggtaaggta | gcaatcatta | caggtggtac | gttgggtatc | 60 |
| ggtttagcta | tcgccacgaa | gttcgttgaa | gaaggggcta | aggtcatgat | taccggccgg | 120 |
| cacagcgatg | ttggtgaaaa | agcagctaag | agtgtcggca | ctcctgatca | gattcaattt | 180 |
| ttccaacatg | attcttccga | tgaagacggc | tggacgaaat | tattcgatgc | aacggaaaaa | 240 |
| gcctttggcc | cagtttctac | attagttaat | aacgctggga | tcgcggttaa | caagagtgtc | 300 |
| gaagaaacca | cgactgctga | atggcgtaaa | ttattagccg | tcaaccttga | tggtgtcttc | 360 |
| ttcggtaccc | gattagggat | tcaacggatg | aagaacaaag | gcttagggc | ttccatcatc | 420 |
| aacatgtctt | cgatcgaagg | ctttgtgggt | gatcctagct | tagggctta | caacgcatct | 480 |
| aaaggggccg | tacggattat | gtccaagtca | gctgccttag | attgtgccct | aaaggactac | 540 |
| gatgttcggg | taaacactgt | tcaccctggc | tacatcaaga | caccattggt | tgatgaccta | 600 |
| ccaggggccg | aagaagcgat | gtcacaacgg | accaagacgc | caatgggcca | tatcggtgaa | 660 |
| cctaacgata | ttgcctacat | ctgtgtttac | ttggcttcta | cgaatctaa | atttgcaacg | 720 |
| ggttctgaat | tgtagttga | cggtggctac | actgctcaat | agtaagcttc | tgttttggcg | 780 |
| gatgagagaa | gattttcagc | ctgatacaga | ttaaatcaga | acgcagaagc | ggtctgataa | 840 |
| aacagaattt | gcctggcggc | agtagcgcgg | tggtcccacc | tgaccccatg | ccgaactcag | 900 |
| aagtgaaacg | ccgtagcgcc | gatggtagtg | tggggtctcc | ccatgcgaga | gtagggaact | 960 |
| gccaggcatc | aaataaaacg | aaaggctcag | tcgaaagact | gggcctttcg | ttttatctgt | 1020 |
| tgtttgtcgg | tgaacgctct | cctgagtagg | acaaatccgc | cgggagcgga | tttgaacgtt | 1080 |
| gcgaagcaac | ggcccggagg | gtggcgggca | ggacgcccgc | cataaactgc | caggcatcaa | 1140 |
| attaagcaga | aggccatcct | gacgatggc | ctttttgcgt | ttctacaaac | tcttttgttt | 1200 |
| atttttctaa | atacattcaa | atatgtatcc | gctcatgaga | caataaccct | gataaatgct | 1260 |
| tcaataatat | tgaaaaagga | agagtatgag | tattcaacat | ttccgtgtcg | cccttattcc | 1320 |
| cttttttgcg | gcattttgcc | ttcctgtttt | tgctcaccca | gaaacgctgg | tgaaagtaaa | 1380 |
| agatgctgaa | gatcagttgg | gtgcacgagt | gggttacatc | gaactggatc | tcaacagcgg | 1440 |
| taagatcctt | gagagttttc | gccccgaaga | acgttttcca | atgatgagca | cttttaaagt | 1500 |
| tctgctatgt | ggcgcggtat | tatcccgtgt | tgacgccggg | caagagcaac | tcggtcgccg | 1560 |

```
catacactat tctcagaatg acttggttga gtactcacca gtcacagaaa agcatcttac      1620
ggatggcatg acagtaagag aattatgcag tgctgccata accatgagtg ataacactgc      1680
ggccaactta cttctgacaa cgatcggagg accgaaggag ctaaccgctt ttttgcacaa      1740
catgggggat catgtaactc gccttgatcg ttgggaaccg gagctgaatg aagccatacc      1800
aaacgacgag cgtgacacca cgatgcctgt agcaatggca acaacgttgc gcaaactatt      1860
aactggcgaa ctacttactc tagcttcccg gcaacaatta atagactgga tggaggcgga      1920
taaagttgca ggaccacttc tgcgctcggc ccttccggct ggctggttta ttgctgataa      1980
atctggagcc ggtgagcgtg gtctcgcgg tatcattgca gcactggggc cagatggtaa       2040
gccctcccgt atcgtagtta tctacacgac ggggagtcag gcaactatgg atgaacgaaa      2100
tagacagatc gctgagatag gtgcctcact gattaagcat tggtaactgt cagaccaagt      2160
ttactcatat atactttaga ttgatttaaa acttcatttt taatttaaaa ggatctaggt       2220
gaagatcctt tttgataatc tcatgaccaa aatcccttaa cgtgagtttt cgttccactg      2280
agcgtcagac cccgtagaaa agatcaaagg atcttcttga tccttttttt ttctgcgcgt      2340
aatctgctgc ttgcaaacaa aaaaaccacc gctaccagcg gtggtttgtt tgccggatca      2400
agagctacca actcttttc cgaaggtaac tggcttcagc agagcgcaga taccaaatac       2460
tgtccttcta gtgtagccgt agttaggcca ccacttcaag aactctgtag caccgcctac      2520
atacctcgct ctgctaatcc tgttaccagt ggctgctgcc agtggcgata agtcgtgtct      2580
taccgggttg gactcaagac gatagttacc ggataaggcg cagcggtcgg gctgaacggg      2640
gggttcgtgc acacagccca gcttggagcg aacgacctac accgaactga gatacctaca      2700
gcgtgagcta tgagaaagcg ccacgcttcc cgaagggaga aaggcggaca ggtatccggt      2760
aagcggcagg gtcggaacag gagagcgcac gagggagctt ccaggggaa acgcctggta       2820 tctttatagt cctgtcgggt ttcgccacct ctgacttgag cgtcgatttt tgtgatgctc      2880
gtcagggggg cggagcctat ggaaaaacgc cagcaacgcg gcctttttac ggttcctggc      2940
cttttgctgg ccttttgctc acatgttctt cctgcgtta tcccctgatt ctgtggataa        3000
ccgtattacc gcctttgagt gagctgatac cgctcgccgc agccgaacga ccgagcgcag      3060
cgagtcagtg agcgaggaag cggaagagcg cctgatgcgg tattttctcc ttacgcatct      3120
gtgcggtatt tcacaccgca tatggtgcac tctcagtaca atctgctctg atgccgcata      3180
gttaagccag tatacactcc gctatcgcta cgtgactggg tcatggctgc gccccgacac      3240
ccgccaacac ccgctgacgc gccctgacgg gcttgtctgc tcccggcatc cgcttacaga      3300
caagctgtga ccgtctccgg gagctgcatg tgtcagaggt tttcaccgtc atcaccgaaa      3360
cgcgcgaggc agctgcggta aagctcatca gcgtggtcgt gaagcgattc acagatgtct      3420
gcctgttcat ccgcgtccag ctcgttgagt ttctccagaa gcgttaatgt ctggcttctg      3480
ataaagcggg ccatgttaag gcggtttttt cctgtttgg tcacttgatg cctccgtgta       3540 aggggaatt tctgttcatg ggggtaatga taccgatgaa acgagagagg atgctcacga       3600
tacgggttac tgatgatgaa catgcccggt tactggaacg ttgtgagggt aaacaactgg      3660
cggtatggat gcggcgggac cagagaaaaa tcactcaggg tcaatgccag cgcttcgtta      3720
atacagatgt aggtgttcca cagggtagcc agcagcatcc tgcgatgcag atccggaaca      3780
taatggtgca gggcgctgac ttccgcgttt ccagacttta cgaaacacgg aaaccgaaga      3840
ccattcatgt tgttgctcag gtcgcagacg ttttgcagca gcagtcgctt cacgttcgct      3900
```

```
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tggctccaat tcttggagtg gtgaatccgt    4140
tagcgaggtg ccgccggctt ccattcaggt cgaggtggcc cggctccatg caccgcgacg    4200
caacgcgggg aggcagacaa ggtatagggc ggcgcctaca atccatgcca acccgttcca    4260
tgtgctcgcc gaggcggcat aaatcgccgt gacgatcagc ggtccagtga tcgaagttag    4320
gctggtaaga gccgcgagcg atccttgaag ctgtccctga tggtcgtcat ctacctgcct    4380
ggacagcatg gcctgcaacg cgggcatccc gatgccgccg aagcgagaa gaatcataat    4440 ggggaaggcc atccagcctc gcgtcgcgaa cgccagcaag acgtagccca gcgcgtcggc    4500
cgccatgccg gcgataatgg cctgcttctc gccgaaacgt ttggtggcgg gaccagtgac    4560
gaaggcttga gcgagggcgt gcaagattcc gaataccgca agcgacaggc cgatcatcgt    4620
cgcgctccag cgaaagcggt cctcgccgaa aatgacccag agcgctgccg gcacctgtcc    4680
tacgagttgc atgataaaga agacagtcat aagtgcggcg acgatagtca tgccccgcgc    4740
ccaccggaag gagctgactg ggttgaaggc tctcaagggc atcggtcgac caaactaaag    4800 cgccttgtg gcgctttagt tttgttcatc ttccagcaag cgtgcgccgg taccttcttc    4860
tcctaagcgg tcgcccgggt tacgcaacgg gcaatcactg cgcgaaaggc agccacaacc    4920
aatacatccg tccagttcgt cacgcagcgc cactaaggta tgaatgcgcc gatccaactc    4980
ttctcgccat tgggacgaaa gctgtttcca ctctttcgca cttaacgtat gcccttcggg    5040
caacacgcca aacgcttcac caatggtcgc cagcggaatg ccaatacgct gagcaatttt    5100
gataattgca acatatcgca acacatcacg tttatatcgc cgctgattgc cgctgttacg    5160
gatactggta atcaacccctt tactttcata gaaatgcagc gccgataccg ccacaccgct    5220
gcgtttcgcc acttcgccgg gggttagcag cgctttaatg cggggtaatt tcttttccat    5280
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccgta agcatgcaag gagaattaca tggtgagcaa    5460
gggcgaggag ctgttcaccg gggtggtgcc catcctggtc gagctggacg gcgacgtaaa    5520
cggccacaag ttcagcgtgt ccggcgaggg cgagggcgat gccacctacg gcaagctgac    5580
cctgaagttc atctgcacca ccggcaagct gcccgtgccc tggcccaccc tcgtgaccac    5640
cttcggctac ggcctgcagt gcttcgcccg ctaccccgac cacatgaagc agcacgactt    5700
cttcaagtcc gccatgcccg aaggctacgt ccaggagcgc accatcttct tcaaggacga    5760
cggcaactac aagacccgcg ccgaggtgaa gttcgagggc gacaccctgg tgaaccgcat    5820
cgagctgaag ggcatcaact tcaaggagga cggcaacatc ctggggcaca agctggagta    5880
caactacaac agccacaacg tctatatcat ggccgacaag cagaagaacg gcatcaaggt    5940
gaacttcaag atccgccaca acatcgaggg cggcagcgtg cagctcgccg accactacca    6000
gcagaacacc cccatcggcg acggccccgt gctgctgccc gacaaccact acctgagcta    6060
ccagtccgcc ctgagcaaag accccaacga gaagcgcgat cacatggtcc tgctggagtt    6120
cgtgaccgcc gccgggatca ctctcggcat ggacgagctg tacaagtaat aaatcgatcc    6180
ggagcttatc gactgcacgg tgcaccaatg cttctggcgt caggcagcca tcggaagctg    6240
tggtatggct gtgcaggtcg taaatcactg cataattcgt gtcgctcaag gcgcactccc    6300
```

```
gttctggata atgttttttg cgccgacatc ataacggttc tggcaaatat tctgaaatga    6360
gctgttgaca attaatcatc ggctcgtata atgtgtggaa ttgtgagcgg ataacaattt    6420
cacacaggaa acagaa                                                    6436

<210> SEQ ID NO 9
<211> LENGTH: 30
<212> TYPE: DNA
<213> ORGANISM: Artificial Sequence
<220> FEATURE:
<223> OTHER INFORMATION: ADH_negK_for

<400> SEQUENCE: 9
acaagaattc gctaagagtg tcggcactcc                                       30

<210> SEQ ID NO 10
<211> LENGTH: 30
<212> TYPE: DNA
<213> ORGANISM: Artificial Sequence
<220> FEATURE:
<223> OTHER INFORMATION: ADH_negK_rev

<400> SEQUENCE: 10
ggccaagctt ccgaagaaga caccatcaag                                       30

<210> SEQ ID NO 11
<211> LENGTH: 5897
<212> TYPE: DNA
<213> ORGANISM: Artificial Sequence
<220> FEATURE:
<223> OTHER INFORMATION: vector

<400> SEQUENCE: 11
agcttctgtt ttggcggatg agagaagatt ttcagcctga tacagattaa atcagaacgc      60
agaagcggtc tgataaaaca gaatttgcct ggcggcagta gcgcggtggt cccacctgac     120
cccatgccga actcagaagt gaaacgccgt agcgccgatg gtagtgtggg gtctccccat     180
gcgagagtag ggaactgcca ggcatcaaat aaaacgaaag gctcagtcga agactgggc     240 ctttcgtttt atctgttgtt tgtcggtgaa cgctctcctg agtaggacaa atccgccggg    300
agcggatttg aacgttgcga agcaacggcc cggagggtgg cgggcaggac gcccgccata    360
aactgccagg catcaaatta gcagaaggc catcctgacg gatggccttt ttgcgttct      420 acaaactctt tgtttatttt tctaaatac attcaaatat gtatccgctc atgagacaat     480
aaccctgata aatgcttcaa taatattgaa aaggaagag tatgagtatt caacatttcc     540
gtgtcgccct tattcccttt tttgcggcat tttgccttcc tgttttgct cacccagaaa     600 cgctggtgaa agtaaaagat gctgaagatc agttgggtgc acgagtgggt tacatcgaac    660
tggatctcaa cagcggtaag atccttgaga gttttcgccc cgaagaacgt tttccaatga    720
tgagcacttt taaagttctg ctatgtggcg cggtattatc ccgtgttgac gccgggcaag    780
agcaactcgg tcgccgcata cactattctc agaatgactt ggttgagtac tcaccagtca    840
cagaaaagca tcttacggat ggcatgacag taagagaatt atgcagtgct gccataacca    900
tgagtgataa cactgcggcc aacttacttc tgacaacgat cggaggaccg aaggagctaa    960 ccgcttttt tgcacaacatg ggggatcatg taactcgcct tgatcgttgg gaaccggagc    1020
tgaatgaagc cataccaaac gacgagcgtg acaccacgat gcctgtagca atggcaacaa    1080
cgttgcgcaa actattaact ggcgaactac ttactctagc ttcccggcaa caattaatag    1140
```

```
actggatgga ggcggataaa gttgcaggac cacttctgcg ctcggccctt ccggctggct    1200
ggtttattgc tgataaatct ggagccggtg agcgtgggtc tcgcggtatc attgcagcac    1260
tggggccaga tggtaagccc tcccgtatcg tagttatcta cacgacgggg agtcaggcaa    1320
ctatggatga acgaaataga cagatcgctg agataggtgc ctcactgatt aagcattggt    1380
aactgtcaga ccaagtttac tcatatatac tttagattga tttaaaactt cattttaat     1440 ttaaaaggat ctaggtgaag atccttttg ataatctcat gaccaaaatc ccttaacgtg      1500
agttttcgtt ccactgagcg tcagaccccg tagaaaagat caaaggatct tcttgagatc    1560
ctttttttct gcgcgtaatc tgctgcttgc aaacaaaaaa accaccgcta ccagcggtgg    1620
tttgtttgcc ggatcaagag ctaccaactc tttttccgaa ggtaactggc ttcagcagag    1680
cgcagatacc aaatactgtc cttctagtgt agccgtagtt aggccaccac ttcaagaact    1740
ctgtagcacc gcctacatac ctcgctctgc taatcctgtt accagtggct gctgccagtg    1800
gcgataagtc gtgtcttacc gggttggact caagacgata gttaccggat aaggcgcagc    1860
ggtcgggctg aacggggggt tcgtgcacac agcccagctt ggagcgaacg acctacaccg    1920
aactgagata cctacagcgt gagctatgag aaagcgccac gcttcccgaa gggagaaagg    1980
cggacaggta tccggtaagc ggcagggtcg aacaggaga gcgcacgagg gagcttccag     2040
ggggaaacgc ctggtatctt tatagtcctg tcgggtttcg ccacctctga cttgagcgtc    2100
gatttttgtg atgctcgtca ggggggcgga gcctatggaa aaacgccagc aacgcggcct    2160
ttttacggtt cctggccttt tgctggcctt tgctcacat gttctttcct gcgttatccc      2220
ctgattctgt ggataaccgt attaccgcct ttgagtgagc tgataccgct cgccgcagcc    2280
gaacgaccga gcgcagcgag tcagtgagcg aggaagcgga agagcgcctg atgcggtatt    2340
ttctccttac gcatctgtgc ggtatttcac accgcatatg gtgcactctc agtacaatct    2400
gctctgatgc cgcatagtta agccagtata cactccgcta tcgctacgtg actgggtcat    2460
ggctgcgccc cgacacccgc caacacccgc tgacgcgccc tgacgggctt gtctgctccc    2520
ggcatccgct tacagacaag ctgtgaccgt ctccgggagc tgcatgtgtc agaggttttc    2580
accgtcatca ccgaaacgcg cgaggcagct gcggtaaagc tcatcagcgt ggtcgtgaag    2640
cgattcacag atgtctgcct gttcatccgc gtccagctcg ttgagtttct ccagaagcgt    2700
taatgtctgg cttctgataa agcgggccat gttaagggcg ttttttcct gtttggtcac     2760 ttgatgcctc cgtgtaaggg ggaatttctg ttcatggggg taatgatacc gatgaaacga    2820
gagaggatgc tcacgatacg ggttactgat gatgaacatg cccggttact ggaacgttgt    2880
gagggtaaac aactggcggt atggatgcgg cgggaccaga gaaaaatcac tcagggtcaa    2940
tgccagcgct tcgttaatac agatgtaggt gttccacagg gtagccagca gcatcctgcg    3000
atgcagatcc ggaacataat ggtgcagggc gctgacttcc gcgtttccag actttacgaa    3060
acacggaaac cgaagaccat tcatgttgtt gctcaggtcg cagacgtttt gcagcagcag    3120
tcgcttcacg ttcgctcgcg tatcggtgat tcattctgct aaccagtaag gcaacccgc     3180 cagcctagcc gggtcctcaa cgacaggagc acgatcatgc gcacccgtgg ccaggaccca    3240
acgctgcccg agatgcgccg cgtgcggctg ctggagatgg cggacgcgat ggatatgttc    3300
tgccaagggt tggtttgcgc attcacagtt ctccgcaaga attgattggc tccaattctt    3360
ggagtggtga atccgttagc gaggtgccgc cggcttccat tcaggtcgag gtggcccggc    3420
tccatgcacc gcgacgcaac gcggggaggc agacaaggta tagggcggcg cctacaatcc    3480
atgccaaccc gttccatgtg ctcgccgagg cggcataaat cgccgtgacg atcagcggtc    3540
```

```
cagtgatcga agttaggctg gtaagagccg cgagcgatcc ttgaagctgt ccctgatggt    3600
cgtcatctac ctgcctggac agcatggcct gcaacgcggg catcccgatg ccgccggaag    3660
cgagaagaat cataatgggg aaggccatcc agcctcgcgt cgcgaacgcc agcaagacgt    3720
agcccagcgc gtcggccgcc atgccggcga taatggcctg cttctcgccg aaacgtttgg    3780
tggcgggacc agtgacgaag gcttgagcga gggcgtgcaa gattccgaat accgcaagcg    3840
acaggccgat catcgtcgcg ctccagcgaa agcggtcctc gccgaaaatg acccagagcg    3900
ctgccggcac ctgtcctacg agttgcatga taaagaagac agtcataagt gcggcgacga    3960
tagtcatgcc ccgcgcccac cggaaggagc tgactgggtt gaaggctctc aagggcatcg    4020
gtcgaccaaa ctaaagcgcc cttgtggcgc tttagttttg ttcatcttcc agcaagcgtg    4080
cgccggtacc ttcttctcct aagcggtcgc ccgggttacg caacgggcaa tcactgcgcg    4140
aaaggcagcc acaaccaata catccgtcca gttcgtcacg cagcgccact aaggtatgaa    4200
tgcgccgatc caactcttct cgccattggg acgaaagctg tttccactct ttcgcactta    4260
acgtatgccc ttcgggcaac acgccaaacg cttcaccaat ggtcgccagc ggaatgccaa    4320
tacgctgagc aattttgata attgcaacat atcgcaacac atcacgttta tatcgccgct    4380
gattgccgct gttacggata ctggtaatca acccttttact ttcatagaaa tgcagcgccg    4440
ataccgccac accgctgcgt ttcgccactt cgccgggggt tagcagcgct ttaatgcggg    4500
gtaatttctt ttccataaat cgctttacct caagttaact tgaggaatta tactccccaa    4560
cagatgaatt aacgaactga acactgaaaa gaggcagatt tatgtcccat cagaaaatta    4620
ttcaggatct tatcgcatgg attgacgagc atattgacca gccgtaagca tgcaaggaga    4680
attacatggt gagcaagggc gaggagctgt tcaccggggt ggtgcccatc ctggtcgagc    4740
tggacggcga cgtaaacggc cacaagttca gcgtgtccgg cgagggcgag ggcgatgcca    4800
cctacggcaa gctgaccctg aagttcatct gcaccaccgg caagctgccc gtgccctggc    4860
ccaccctcgt gaccaccttc ggctacggcc tgcagtgctt cgcccgctac cccgaccaca    4920
tgaagcagca cgacttcttc aagtccgcca tgcccgaagg ctacgtccag gagcgcacca    4980
tcttcttcaa ggacgacggc aactacaaga cccgcgccga ggtgaagttc gagggcgaca    5040
ccctggtgaa ccgcatcgag ctgaagggca tcaacttcaa ggaggacggc aacatcctgg    5100
ggcacaagct ggagtacaac tacaacagcc acaacgtcta tatcatggcc gacaagcaga    5160
agaacggcat caaggtgaac ttcaagatcc gccacaacat cgagggcggc agcgtgcagc    5220
tcgccgacca ctaccagcag aacaccccca tcggcgacgg ccccgtgctg ctgcccgaca    5280
accactacct gagctaccag tccgccctga gcaaagaccc caacgagaag cgcgatcaca    5340
tggtcctgct ggagttcgtg accgccgccg ggatcactct cggcatggac gagctgtaca    5400
agtaataaat cgatccggag cttatcgact gcacggtgca ccaatgcttc tggcgtcagg    5460
cagccatcgg aagctgtggt atggctgtgc aggtcgtaaa tcactgcata attcgtgtcg    5520
ctcaaggcgc actcccgttc tggataatgt tttttgcgcc gacatcataa cggttctggc    5580
aaatattctg aaatgagctg ttgacaatta atcatcggct cgtataatgt gtggaattgt    5640
gagcggataa caatttcaca caggaaacag aattcgctaa gagtgtcggc actcctgatc    5700
agattcaatt tttccaacat gattcttccg atgaagacgg ctggacgaaa ttattcgatg    5760
caacggaaaa agcctttggc ccagtttcta cattagttaa taacgctggg atcgcggtta    5820
acaagagtgt cgaagaaacc acgactgctg aatggcgtaa attattagcc gtcaaccttg    5880
```

```
atggtgtctt cttcgga                                                      5897
```

<210> SEQ ID NO 12
<211> LENGTH: 30
<212> TYPE: DNA
<213> ORGANISM: Artificial Sequence
<220> FEATURE:
<223> OTHER INFORMATION: L194S_for

<400> SEQUENCE: 12

```
ctggctacat caagacacca tctgttgatg                                          30
```

<210> SEQ ID NO 13
<211> LENGTH: 30
<212> TYPE: DNA
<213> ORGANISM: Artificial Sequence
<220> FEATURE:
<223> OTHER INFORMATION: L194S_rev

<400> SEQUENCE: 13

```
cggcccctgg taggtcatca acagatggtg                                          30
```

<210> SEQ ID NO 14
<211> LENGTH: 6436
<212> TYPE: DNA
<213> ORGANISM: Artificial Sequence
<220> FEATURE:
<223> OTHER INFORMATION: vector

<400> SEQUENCE: 14

```
ttcatgtcta accgtttgga tggtaaggta gcaatcatta caggtggtac gttgggtatc         60
ggtttagcta tcgccacgaa gttcgttgaa gaaggggcta aggtcatgat taccggccgg        120
cacagcgatt tggtgaaaaa agcagctaag agtgtcggca ctcctgatca gattcaattt        180
ttccaacatg attcttccga tgaagacggc tggacgaaat tattcgatgc aacggaaaaa        240
gcctttggcc cagtttctac attagttaat aacgctggga tcgcggttaa caagagtgtc        300
gaagaaacca cgactgctga atggcgtaaa ttattagccg tcaaccttga tggtgtcttc        360
ttcggtaccc gattagggat tcaacggatg aagaacaaag gcttaggggc ttccatcatc        420
aacatgtctt cgatcgaagg ctttgtgggt gatcctagct tagggcttaa caacgcatct        480
aaaggggccg tacggattat gtccaagtca gctgccttag attgtgccct aaaggactac        540
gatgttcggg taaacactgt tcaccctggc tacatcaaga ccatctgtgt tgatgaccta        600
ccaggggccg aagaagcgat gtcacaacgg accaagacgc aatgggcca tatcggtgaa         660
cctaacgata ttgcctacat ctgtgtttac ttggcttcta cgaatctaa atttgcaacg         720
ggttctgaat tgtagttga cggtggctac actgctcaat agtaagcttc tgttttggcg         780
gatgagagaa gattttcagc ctgatacaga ttaaatcaga acgcagaagc ggtctgataa        840
aacagaattt gcctggcggc agtagcgcgg tggtcccacc tgaccccatg ccgaactcag        900
aagtgaaacg ccgtagcgcc gatggtagtg tggggtctcc ccatgcgaga gtagggaact        960
gccaggcatc aaataaaacg aaaggctcag tcgaaagact gggcctttcg ttttatctgt       1020
tgtttgtcgg tgaacgctct cctgagtagg acaaatccgc cgggagcgga tttgaacgtt      1080
gcgaagcaac ggcccggagg gtggcgggca ggacgcccgc cataaactgc caggcatcaa       1140
attaagcaga aggccatcct gacggatggc cttttttgcgt ttctacaaac tcttttgttt       1200
atttttctaa atacattcaa atatgtatcc gctcatgaga caataaccct gataaatgct       1260
tcaataatat tgaaaaagga agagtatgag tattcaacat ttccgtgtcg cccttattcc       1320
```

-continued

```
cttttttgcg gcattttgcc ttcctgtttt tgctcaccca gaaacgctgg tgaaagtaaa      1380
agatgctgaa gatcagttgg gtgcacgagt gggttacatc gaactggatc tcaacagcgg      1440
taagatcctt gagagttttc gccccgaaga acgttttcca atgatgagca cttttaaagt      1500
tctgctatgt ggcgcggtat tatcccgtgt tgacgccggg caagagcaac tcggtcgccg      1560
catacactat tctcagaatg acttggttga gtactcacca gtcacagaaa agcatcttac      1620
ggatggcatg acagtaagag aattatgcag tgctgccata accatgagtg ataacactgc      1680
ggccaactta cttctgacaa cgatcggagg accgaaggag ctaaccgctt ttttgcacaa      1740
catgggggat catgtaactc gccttgatcg ttgggaaccg gagctgaatg aagccatacc      1800
aaacgacgag cgtgacacca cgatgcctgt agcaatggca acaacgttgc gcaaactatt      1860
aactggcgaa ctacttactc tagcttcccg gcaacaatta atagactgga tggaggcgga      1920
taaagttgca ggaccacttc tgcgctcggc ccttccggct ggctggttta ttgctgataa      1980
atctggagcc ggtgagcgtg ggtctcgcgg tatcattgca gcactgggc cagatggtaa      2040 gccctcccgt atcgtagtta tctacacgac ggggagtcag gcaactatgg atgaacgaaa      2100
tagacagatc gctgagatag gtgcctcact gattaagcat tggtaactgt cagaccaagt      2160
ttactcatat atactttaga ttgatttaaa acttcatttt taatttaaaa ggatctaggt      2220
gaagatcctt tttgataatc tcatgaccaa aatcccttaa cgtgagtttt cgttccactg      2280
agcgtcagac cccgtagaaa agatcaaagg atcttcttga gatcctttt ttctgcgcgt      2340 aatctgctgc ttgcaaacaa aaaaaccacc gctaccagcg gtggtttgtt tgccggatca      2400
agagctacca actctttttc cgaaggtaac tggcttcagc agagcgcaga taccaaatac      2460
tgtccttcta gtgtagccgt agttaggcca ccacttcaag aactctgtag caccgcctac      2520
atacctcgct ctgctaatcc tgttaccagt ggctgctgcc agtggcgata agtcgtgtct      2580
taccgggttg gactcaagac gatagttacc ggataaggcg cagcggtcgg gctgaacggg      2640
gggttcgtgc acacagccca gcttggagcg aacgacctac accgaactga gatacctaca      2700
gcgtgagcta tgagaaagcg ccacgcttcc cgaaggagagaaggcggaca ggtatccggt      2760 aagcggcagg gtcggaacag gagagcgcac gagggagctt ccaggggaa acgcctggta      2820 tctttatagt cctgtcgggt ttcgccacct ctgacttgag cgtcgatttt tgtgatgctc      2880
gtcagggggg cggagcctat ggaaaaacgc cagcaacgcg ccttttttac ggttcctggc      2940
cttttgctgg ccttttgctc acatgttctt tcctgcgtta tcccctgatt ctgtggataa      3000
ccgtattacc gcctttgagt gagctgatac cgctcgccgc agccgaacga ccgagcgcag      3060
cgagtcagtg agcgaggaag cggaagagcg cctgatgcgg tattttctcc ttacgcatct      3120
gtgcggtatt tcacaccgca tatggtgcac tctcagtaca atctgctctg atgccgcata      3180
gttaagccag tatacactcc gctatcgcta cgtgactggg tcatggctgc gccccgacac      3240
ccgccaacac ccgctgacgc gccctgacgg gcttgtctgc tcccggcatc cgcttacaga      3300
caagctgtga ccgtctccgg gagctgcatg tgtcagaggt tttcaccgtc atcaccgaaa      3360
cgcgcgaggc agctgcggta aagctcatca gcgtggtcgt gaagcgattc acagatgtct      3420
gcctgttcat ccgcgtccag ctcgttgagt ttctccagaa gcgttaatgt ctggcttctg      3480
ataaagcggg ccatgttaag ggcggttttt tcctgtttgg tcacttgatg cctccgtgta      3540
agggggaatt tctgttcatg ggggtaatga taccgatgaa acgagagagg atgctcacga      3600
tacgggttac tgatgatgaa catgcccggt tactggaacg ttgtgagggt aaacaactgg      3660
```

```
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tggctccaat tcttggagtg gtgaatccgt    4140
tagcgaggtg ccgccggctt ccattcaggt cgaggtggcc cggctccatg caccgcgacg    4200
caacgcgggg aggcagacaa ggtatagggc ggcgcctaca atccatgcca acccgttcca    4260
tgtgctcgcc gaggcggcat aaatcgccgt gacgatcagc ggtccagtga tcgaagttag    4320
gctggtaaga gccgcgagcg atccttgaag ctgtccctga tggtcgtcat ctacctgcct    4380
ggacagcatg gcctgcaacg cgggcatccc gatgccgccg gaagcgagaa gaatcataat    4440
ggggaaggcc atccagcctc gcgtcgcgaa cgccagcaag acgtagccca gcgcgtcggc    4500
cgccatgccg gcgataatgg cctgcttctc gccgaaacgt ttggtggcgg gaccagtgac    4560
gaaggcttga gcgagggcgt gcaagattcc gaataccgca agcgacaggc cgatcatcgt    4620
cgcgctccag cgaaagcggt cctcgccgaa aatgacccag agcgctgccg gcacctgtcc    4680
tacgagttgc atgataaaga agacagtcat aagtgcggcg acgatagtca tgccccgcgc    4740
ccaccggaag gagctgactg ggttgaaggc tctcaagggc atcggtcgac caaactaaag    4800
cgcccttgtg gcgctttagt tttgttcatc ttccagcaag cgtgcgccgg taccttcttc    4860
tcctaagcgg tcgcccgggt tacgcaacgg gcaatcactg cgcgaaaggc agccacaacc    4920
aatacatccg tccagttcgt cacgcagcgc cactaaggta tgaatgcgcc gatccaactc    4980
ttctcgccat tgggacgaaa gctgtttcca ctctttcgca cttaacgtat gcccttcggg    5040
caacacgcca aacgcttcac caatggtcgc cagcggaatg ccaatacgct gagcaatttt    5100
gataattgca acatatcgca acacatcacg tttatatcgc cgctgattgc cgctgttacg    5160
gatactggta atcaacccctt tactttcata gaaatgcagc gccgataccg ccacaccgct    5220
gcgtttcgcc acttcgccgg gggttagcag cgctttaatg cggggtaatt tcttttccat    5280
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccgta agcatgcaag gagaattaca tggtgagcaa    5460
gggcgaggag ctgttcaccg gggtggtgcc catcctggtc gagctggacg gcgacgtaaa    5520
cggccacaag ttcagcgtgt ccggcgaggg cgagggcgat gccacctacg gcaagctgac    5580
cctgaagttc atctgcacca ccggcaagct gcccgtgccc tggcccaccc tcgtgaccac    5640
cttcggctac ggcctgcagt gcttcgcccg ctaccccgac cacatgaagc agcacgactt    5700
cttcaagtcc gccatgcccg aaggctacgt ccaggagcgc accatcttct tcaaggacga    5760
cggcaactac aagacccgcg ccgaggtgaa gttcgagggc gacaccctgg tgaaccgcat    5820
cgagctgaag ggcatcaact tcaaggagga cggcaacatc ctggggcaca agctggagta    5880
caactacaac agccacaacg tctatatcat ggccgacaag cagaagaacg gcatcaaggt    5940
gaacttcaag atccgccaca acatcgaggg cggcagcgtg cagctcgccg accactacca    6000
gcagaacacc cccatcggcg acggccccgt gctgctgccc gacaaccact acctgagcta    6060
```

-continued

```
ccagtccgcc ctgagcaaag accccaacga gaagcgcgat cacatggtcc tgctggagtt    6120
cgtgaccgcc gccgggatca ctctcggcat ggacgagctg tacaagtaat aaatcgatcc    6180
ggagcttatc gactgcacgg tgcaccaatg cttctggcgt caggcagcca tcggaagctg    6240
tggtatggct gtgcaggtcg taaatcactg cataattcgt gtcgctcaag gcgcactccc    6300
gttctggata atgttttttg cgccgacatc ataacggttc tggcaaatat tctgaaatga    6360
gctgttgaca attaatcatc ggctcgtata atgtgtggaa ttgtgagcgg ataacaattt    6420
cacacaggaa acagaa                                                     6436
```

<210> SEQ ID NO 15
<211> LENGTH: 30
<212> TYPE: DNA
<213> ORGANISM: Artificial Sequence
<220> FEATURE:
<223> OTHER INFORMATION: L194A_for

<400> SEQUENCE: 15

```
ctggctacat caagacacca gcggttgatg                                        30
```

<210> SEQ ID NO 16
<211> LENGTH: 30
<212> TYPE: DNA
<213> ORGANISM: Artificial Sequence
<220> FEATURE:
<223> OTHER INFORMATION: L194A_rev

<400> SEQUENCE: 16

```
cggcccctgg taggtcatca accgctggtg                                        30
```

<210> SEQ ID NO 17
<211> LENGTH: 6436
<212> TYPE: DNA
<213> ORGANISM: Artificial Sequence
<220> FEATURE:
<223> OTHER INFORMATION: vector

<400> SEQUENCE: 17

```
ttcatgtcta accgtttgga tggtaaggta gcaatcatta caggtggtac gttgggtatc      60
ggtttagcta tcgccacgaa gttcgttgaa gaaggggcta aggtcatgat taccggccgg     120
cacagcgatt ttggtgaaaa agcagctaag agtgtcggca ctcctgatca gattcaattt     180
ttccaacatg attcttccga tgaagacggc tggacgaaat tattcgatgc aacggaaaaa     240
gcctttggcc cagtttctac attagttaat aacgctggga tcgcggttaa caagagtgtc     300
gaagaaacca cgactgctga atggcgtaaa ttattagccg tcaaccttga tggtgtcttc     360
ttcggtaccc gattagggat tcaacggatg aagaacaaag gcttaggggc ttccatcatc     420
aacatgtctt cgatcgaagg ctttgtgggt gatcctagct tagggcttca aacgcatct     480 aaaggggccg tacggattat gtccaagtca gctgccttag attgtgccct aaaggactac    540
gatgttcggg taaacactgt tcaccctggc tacatcaaga caccagcggt tgatgaccta    600
ccaggggccg aagaagcgat gtcacaacg accaagacgc caatgggcca tatcggtgaa    660
cctaacgata ttgcctacat ctgtgtttac ttggcttcta cgaatctaaa attgcaacg    720 ggttctgaat ttgtagttga cggtggctac actgctcaat agtaagcttc tgttttggcg    780
gatgagagaa gattttcagc ctgatacaga ttaaatcaga acgcagaagc ggtctgataa    840
aacagaattt gcctggcggc agtagcgcgg tggtcccacc tgaccccatg ccgaactcag    900
```

```
aagtgaaacg ccgtagcgcc gatggtagtg tggggtctcc ccatgcgaga gtagggaact    960
gccaggcatc aaataaaacg aaaggctcag tcgaaagact gggcctttcg ttttatctgt   1020
tgtttgtcgg tgaacgctct cctgagtagg acaaatccgc cgggagcgga tttgaacgtt   1080
gcgaagcaac ggcccggagg gtggcgggca ggacgcccgc cataaactgc caggcatcaa   1140
attaagcaga aggccatcct gacggatggc cttttgcgt ttctacaaac tcttttgttt    1200
atttttctaa atacattcaa atatgtatcc gctcatgaga caataaccct gataaatgct   1260
tcaataatat tgaaaaagga gagtatgag tattcaacat ttccgtgtcg cccttattcc    1320
cttttttgcg gcattttgcc ttcctgtttt tgctcaccca gaaacgctgg tgaaagtaaa   1380
agatgctgaa gatcagttgg gtgcacgagt gggttacatc gaactggatc tcaacagcgg   1440
taagatcctt gagagttttc gccccgaaga acgttttcca atgatgagca cttttaaagt   1500
tctgctatgt ggcgcggtat tatcccgtgt tgacgccggg caagagcaac tcggtcgccg   1560
catacactat tctcagaatg acttggttga gtactcacca gtcacagaaa agcatcttac   1620
ggatggcatg acagtaagag aattatgcag tgctgccata accatgagtg ataacactgc   1680
ggccaactta cttctgacaa cgatcggagg accgaaggag ctaaccgctt ttttgcacaa   1740
catggggat catgtaactc gccttgatcg ttgggaaccg gagctgaatg aagccatacc    1800
aaacgacgag cgtgacacca cgatgcctgt agcaatggca acaacgttgc gcaaactatt   1860
aactggcgaa ctacttactc tagcttcccg gcaacaatta atagactgga tggaggcgga   1920
taaagttgca ggaccacttc tgcgctcggc ccttccggct ggctggttta ttgctgataa   1980
atctggagcc ggtgagcgtg ggtctcgcgg tatcattgca gcactggggc cagatggtaa   2040
gccctcccgt atcgtagtta tctacacgac ggggagtcag gcaactatgg atgaacgaaa   2100
tagacagatc gctgagatag gtgcctcact gattaagcat tggtaactgt cagaccaagt   2160
ttactcatat atactttaga ttgatttaaa acttcatttt taatttaaaa ggatctaggt   2220
gaagatcctt tttgataatc tcatgaccaa aatcccttaa cgtgagtttt cgttccactg   2280
agcgtcagac cccgtagaaa agatcaaagg atcttcttga gatcctttt ttctgcgcgt    2340
aatctgctgc ttgcaaacaa aaaaaccacc gctaccagcg gtggtttgtt tgccggatca   2400
agagctacca actctttttc cgaaggtaac tggcttcagc agagcgcaga taccaaatac   2460
tgtccttcta gtgtagccgt agttaggcca ccacttcaag aactctgtag caccgcctac   2520
atacctcgct ctgctaatcc tgttaccagt ggctgctgcc agtggcgata agtcgtgtct   2580
taccgggttg gactcaagac gatagttacc ggataaggcg cagcggtcgg gctgaacggg   2640
gggttcgtgc acacagccca gcttggagcg aacgacctac accgaactga gatacctaca   2700
gcgtgagcta tgagaaagcg ccacgcttcc cgaagggaga aaggcggaca ggtatccggt   2760
aagcggcagg gtcggaacag gagagcgcac gagggagctt ccaggggaa acgcctggta    2820
tctttatagt cctgtcgggt ttcgccacct ctgacttgag cgtcgatttt tgtgatgctc   2880
gtcagggggg cggagcctat ggaaaaacgc cagcaacgcg gccttttac ggttcctggc    2940
cttttgctgg ccttttgctc acatgttctt tcctgcgtta tcccctgatt ctgtggataa   3000
ccgtattacc gcctttgagt gagctgatac cgctcgccgc agccgaacga ccgagcgcag   3060
cgagtcagtg agcgaggaag cggaagagcg cctgatgcgg tattttctcc ttacgcatct   3120
gtgcggtatt tcacaccgca tatggtgcac tctcagtaca atctgctctg atgccgcata   3180
gttaagccag tatacactcc gctatcgcta cgtgactggg tcatggctgc gccccgacac   3240
ccgccaacac ccgctgacgc gccctgacgg gcttgtctgc tcccggcatc cgcttacaga   3300
```

```
caagctgtga ccgtctccgg gagctgcatg tgtcagaggt tttcaccgtc atcaccgaaa    3360
cgcgcgaggc agctgcggta aagctcatca gcgtggtcgt gaagcgattc acagatgtct    3420
gcctgttcat ccgcgtccag ctcgttgagt ttctccagaa gcgttaatgt ctggcttctg    3480
ataaagcggg ccatgttaag ggcggttttt tcctgtttgg tcacttgatg cctccgtgta    3540 aggggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tggctccaat tcttggagtg gtgaatccgt    4140
tagcgaggtg ccgccggctt ccattcaggt cgaggtggcc cggctccatg caccgcgacg    4200
caacgcgggg aggcagacaa ggtatagggc ggcgcctaca atccatgcca acccgttcca    4260
tgtgctcgcc gaggcggcat aaatcgccgt gacgatcagc ggtccagtga tcgaagttag    4320
gctggtaaga gccgcgagcg atccttgaag ctgtccctga tggtcgtcat ctacctgcct    4380
ggacagcatg gcctgcaacg cgggcatccc gatgccgccg gaagcgagaa gaatcataat    4440
ggggaaggcc atccagcctc gcgtcgcgaa cgccagcaag acgtagccca gcgcgtcggc    4500
cgccatgccg gcgataatgg cctgcttctc gccgaaacgt ttggtggcgg gaccagtgac    4560
gaaggcttga gcgagggcgt gcaagattcc gaataccgca agcgacaggc cgatcatcgt    4620
cgcgctccag cgaaagcggt cctcgccgaa aatgacccag agcgctgccg gcacctgtcc    4680
tacgagttgc atgataaaga agacagtcat aagtgcggcg acgatagtca tgccccgcgc    4740
ccaccggaag gagctgactg ggttgaaggc tctcaagggc atcggtcgac caaactaaag    4800
cgcccttgtg gcgctttagt tttgttcatc ttccagcaag cgtgcgccgg taccttcttc    4860
tcctaagcgg tcgcccgggt tacgcaacgg gcaatcactg cgcgaaaggc agccacaacc    4920
aatacatccg tccagttcgt cacgcagcgc cactaaggta tgaatgcgcc gatccaactc    4980
ttctcgccat tgggacgaaa gctgtttcca ctctttcgca cttaacgtat gcccttcggg    5040
caacacgcca aacgcttcac caatggtcgc cagcggaatg ccaatacgct gagcaatttt    5100
gataattgca acatatcgca acacatcacg tttatatcgc cgctgattgc cgctgttacg    5160
gatactggta atcaacccctt tactttcata gaaatgcagc gccgataccg ccacaccgct    5220
gcgtttcgcc acttcgccgg gggttagcag cgctttaatg cggggtaatt tcttttccat    5280
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccgta agcatgcaag gagaattaca tggtgagcaa    5460
gggcgaggag ctgttcaccg gggtggtgcc catcctggtc gagctggacg gcgacgtaaa    5520
cggccacaag ttcagcgtgt ccggcgaggg cgagggcgat gccacctacg gcaagctgac    5580
cctgaagttc atctgcacca ccggcaagct gcccgtgccc tggcccaccc tcgtgaccac    5640
```

```
cttcggctac ggcctgcagt gcttcgcccg ctaccccgac cacatgaagc agcacgactt   5700
cttcaagtcc gccatgcccg aaggctacgt ccaggagcgc accatcttct tcaaggacga   5760
cggcaactac aagacccgcg ccgaggtgaa gttcgagggc gacaccctgg tgaaccgcat   5820
cgagctgaag ggcatcaact tcaaggagga cggcaacatc ctggggcaca agctggagta   5880
caactacaac agccacaacg tctatatcat ggccgacaag cagaagaacg gcatcaaggt   5940
gaacttcaag atccgccaca acatcgaggg cggcagcgtg cagctcgccg accactacca   6000
gcagaacacc cccatcggcg acggccccgt gctgctgccc gacaaccact acctgagcta   6060
ccagtccgcc ctgagcaaag accccaacga gaagcgcgat cacatggtcc tgctggagtt   6120
cgtgaccgcc gccgggatca ctctcggcat ggacgagctg tacaagtaat aaatcgatcc   6180
ggagcttatc gactgcacgg tgcaccaatg cttctggcgt caggcagcca tcggaagctg   6240
tggtatggct gtgcaggtcg taaatcactg cataattcgt gtcgctcaag gcgcactccc   6300
gttctggata atgttttttg cgccgacatc ataacggttc tggcaaatat tctgaaatga   6360
gctgttgaca attaatcatc ggctcgtata atgtgtggaa ttgtgagcgg ataacaattt   6420
cacacaggaa acagaa                                                   6436

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
acaagaattc gctaagagtg tcggcactcc                                      30

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
ggccaagctt ccgaagaaga caccatcaag                                      30

<210> SEQ ID NO 20
<211> LENGTH: 6436
<212> TYPE: DNA
<213> ORGANISM: Artificial Sequence
<220> FEATURE:
<223> OTHER INFORMATION: vector

<400> SEQUENCE: 20
ttcatgtcta accgtttgga tggtaaggta gcaatcatta caggtggtac gttgggtatc     60
ggtttagcta tcgccacgaa gttcgttgaa gaagggggcta aggtcatgat taccggccgg    120
cacagcgatg ttggtgaaaa agcagctaag agtgtcggca ctcctgatca gattcaattt    180
ttccaacatg attcttccga tgaagacggc tggacgaaat tattcgatgc aacggaaaaa    240
gcctttggcc cagtttctac attagttaat aacgctggga tcatggttaa caagagtgtc    300
gaagaaacca cgactgctga atggcgtaaa ttattagccg tcaaccttga tggtgtcttc    360
ttcggtaccc gattagggat tcaacgatg aagaacaaag cttaggggc ttccatcatc      420 aacatgtctt cgatcgaagg ctttgtgggt gatcctagct tagggctta caacgcatct    480 aaggggccg tacggattat gtccaagtca gctgccttag attgtgccct aaaggactac    540
```

-continued

```
gatgttcggg taaacactgt tcaccctggc tacatcaaga caccattggt tgatgaccta      600 ccagggccg aagaagcgat gtcacaacgg accaagacgc caatgggcca tatcggtgaa       660
cctaacgata ttgcctacat ctgtgtttac ttggcttcta acgaatctaa atttgcaacg      720
ggttctgaat ttgtagttga cggtggctac actgctcaat agtaagcttc tgttttggcg      780
gatgagagaa gattttcagc ctgatacaga ttaaatcaga acgcagaagc ggtctgataa      840
aacagaattt gcctggcggc agtagcgcgg tggtcccacc tgaccccatg ccgaactcag      900
aagtgaaacg ccgtagcgcc gatggtagtg tggggtctcc ccatgcgaga gtagggaact      960
gccaggcatc aaataaaacg aaaggctcag tcgaaagact gggccttcg ttttatctgt      1020 tgtttgtcgg tgaacgctct cctgagtagg acaaatccgc cgggagcgga tttgaacgtt     1080
gcgaagcaac ggcccggagg gtggcgggca ggacgcccgc cataaactgc caggcatcaa     1140
attaagcaga aggccatcct gacggatggc cttttttgcgt ttctacaaac tcttttgttt   1200 attttttctaa atacattcaa atatgtatcc gctcatgaga caataaccct gataaatgct    1260
tcaataatat tgaaaaagga gagtatgag tattcaacat ttccgtgtcg cccttattcc      1320 ctttttttgcg gcattttgcc ttcctgtttt tgctcaccca gaaacgctgg tgaaagtaaa    1380
agatgctgaa gatcagttgg gtgcacgagt gggttacatc gaactggatc tcaacagcgg    1440
taagatcctt gagagttttc gccccgaaga acgttttcca atgatgagca cttttaaagt    1500
tctgctatgt ggcgcggtat tatcccgtgt tgacgccggg caagagcaac tcggtcgccg    1560
catacactat tctcagaatg acttggttga gtactcacca gtcacagaaa agcatcttac     1620
ggatggcatg acagtaagag aattatgcag tgctgccata accatgagtg ataacactgc     1680
ggccaactta cttctgacaa cgatcggagg accgaaggag ctaaccgctt ttttgcacaa     1740 catggggat catgtaactc gccttgatcg ttgggaaccg gagctgaatg aagccatacc     1800
aaacgacgag cgtgacacca cgatgcctgt agcaatggca acaacgttgc gcaaactatt     1860
aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg ggtctcgcgg tatcattgca gcactgggc cagatggtaa    2040 gccctcccgt atcgtagtta tctacacgac ggggagtcag gcaactatgg atgaacgaaa    2100
tagacagatc gctgagatag gtgcctcact gattaagcat tggtaactgt cagaccaagt    2160
ttactcatat atactttaga ttgatttaaa acttcatttt taatttaaaa ggatctaggt    2220
gaagatcctt tttgataatc tcatgaccaa aatcccttaa cgtgagtttt cgttccactg    2280
agcgtcagac cccgtagaaa agatcaaagg atcttcttga gatccttttt ttctgcgcgt    2340
aatctgctgc ttgcaaacaa aaaaaccacc gctaccagcg gtggtttgtt tgccggatca    2400
agagctacca actctttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata agtcgtgtct    2580
taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc cgaagggaga aaggcggaca ggtatccggt    2760
aagcggcagg gtcggaacag gagagcgcac gagggagctt ccagggggaa acgcctggta    2820
tctttatagt cctgtcgggt ttcgccacct ctgacttgag cgtcgatttt tgtgatgctc    2880
```

```
gtcagggggg cggagcctat ggaaaaacgc cagcaacgcg gccttttac ggttcctggc      2940 cttttgctgg ccttttgctc acatgttctt tcctgcgtta tccctgatt ctgtggataa       3000 ccgtattacc gcctttgagt gagctgatac cgctcgccgc agccgaacga ccgagcgcag      3060
cgagtcagtg agcgaggaag cggaagagcg cctgatgcgg tattttctcc ttacgcatct      3120
gtgcggtatt tcacaccgca tatggtgcac tctcagtaca atctgctctg atgccgcata      3180
gttaagccag tatacactcc gctatcgcta cgtgactggg tcatggctgc gccccgacac      3240
ccgccaacac ccgctgacgc gccctgacgg gcttgtctgc tcccggcatc cgcttacaga      3300
caagctgtga ccgtctccgg gagctgcatg tgtcagaggt tttcaccgtc atcaccgaaa      3360
cgcgcgaggc agctgcggta aagctcatca gcgtggtcgt gaagcgattc acagatgtct      3420
gcctgttcat ccgcgtccag ctcgttgagt ttctccagaa gcgttaatgt ctggcttctg      3480
ataaagcggg ccatgttaag gcggttttt cctgtttgg tcacttgatg cctccgtgta       3540
agggggaatt tctgttcatg ggggtaatga taccgatgaa acgagagagg atgctcacga     3600
tacgggttac tgatgatgaa catgcccggt tactggaacg ttgtgagggt aaacaactgg      3660
cggtatggat gcggcgggac cagagaaaaa tcactcaggg tcaatgccag cgcttcgtta     3720
atacagatgt aggtgttcca cagggtagcc agcagcatcc tgcgatgcag atccggaaca     3780
taatggtgca gggcgctgac ttccgcgttt ccagacttta cgaaacacgg aaaccgaaga     3840
ccattcatgt tgttgctcag gtcgcagacg ttttgcagca gcagtcgctt cacgttcgct      3900
cgcgtatcgg tgattcattc tgctaaccag taaggcaacc ccgccagcct agccgggtcc     3960
tcaacgacag gagcacgatc atgcgcaccc gtggccagga cccaacgctg cccgagatgc     4020
gccgcgtgcg gctgctggag atggcggacg cgatggatat gttctgccaa gggttggttt      4080
gcgcattcac agttctccgc aagaattgat tggctccaat tcttggagtg gtgaatccgt      4140
tagcgaggtg ccgccggctt ccattcaggt cgaggtggcc cggctccatg caccgcgacg     4200
caacgcgggg aggcagacaa ggtatagggc ggcgcctaca atccatgcca cccgttcca      4260 tgtgctcgcc gaggcggcat aaatcgccgt gacgatcagc ggtccagtga tcgaagttag     4320
gctggtaaga gccgcgagcg atccttgaag ctgtccctga tggtcgtcat ctacctgcct     4380
ggacagcatg gcctgcaacg cgggcatccc gatgccgccg gaagcgagaa gaatcataat      4440
ggggaaggcc atccagcctc gcgtcgcgaa cgccagcaag acgtagccca gcgcgtcggc     4500
cgccatgccg gcgataatgg cctgcttctc gccgaaacgt ttggtggcgg gaccagtgac     4560
gaaggcttga gcgagggcgt gcaagattcc gaataccgca agcgacaggc cgatcatcgt      4620
cgcgctccag cgaaagcggt cctcgccgaa aatgacccag agcgctgccg gcacctgtcc     4680
tacgagttgc atgataaaga agacagtcat aagtgcggcg acgatagtca tgccccgcgc     4740
ccaccggaag gagctgactg ggttgaaggc tctcaagggc atcggtcgac caaactaaag    4800
cgcccttgtg gcgctttagt tttgttcatc ttccagcaag cgtgcgccgg taccttcttc      4860
tcctaagcgg tcgcccgggt tacgcaacgg gcaatcactg cgcgaaaggc agccacaacc      4920
aatacatccg tccagttcgt cacgcagcgc cactaaggta tgaatgcgcc gatccaactc      4980
ttctcgccat tgggacgaaa gctgtttcca ctctttcgca cttaacgtat gcccttcggg      5040
caacacgcca aacgcttcac caatggtcgc cagcggaatg ccaatacgct gagcaatttt      5100
gataattgca acatatcgca acacatcacg tttatatcgc cgctgattgc cgctgttacg     5160
gatactggta atcaacccct tactttcata gaaatgcagc gccgataccg ccacaccgct      5220
gcgtttcgcc acttcgccgg gggttagcag cgcttaatg cggggtaatt tcttttccat       5280
```

-continued

```
aaatcgcttt acctcaagtt aacttgagga attatactcc ccaacagatg aattaacgaa    5340
ctgaacactg aaaagaggca gatttatgtc ccatcagaaa attattcagg atcttatcgc    5400
atggattgac gagcatattg accagccgta agcatgcaag gagaattaca tggtgagcaa    5460
gggcgaggag ctgttcaccg gggtggtgcc catcctggtc gagctggacg gcgacgtaaa    5520
cggccacaag ttcagcgtgt ccggcgaggg cgagggcgat gccacctacg gcaagctgac    5580
cctgaagttc atctgcacca ccggcaagct gcccgtgccc tggcccaccc tcgtgaccac    5640
cttcggctac ggcctgcagt gcttcgcccg ctaccccgac cacatgaagc agcacgactt    5700
cttcaagtcc gccatgcccg aaggctacgt ccaggagcgc accatcttct tcaaggacga    5760
cggcaactac aagacccgcg ccgaggtgaa gttcgagggc gacaccctgg tgaaccgcat    5820
cgagctgaag ggcatcaact tcaaggagga cggcaacatc ctggggcaca gctggagta    5880 caactacaac agccacaacg tctatatcat ggccgacaag cagaagaacg gcatcaaggt    5940
gaacttcaag atccgccaca acatcgaggg cggcagcgtg cagctcgccg accactacca    6000
gcagaacacc cccatcggcg acggccccgt gctgctgccc gacaaccact acctgagcta    6060
ccagtccgcc ctgagcaaag accccaacga gaagcgcgat cacatggtcc tgctggagtt    6120
cgtgaccgcc gccgggatca ctctcggcat ggacgagctg tacaagtaat aaatcgatcc    6180
ggagcttatc gactgcacgg tgcaccaatg cttctggcgt caggcagcca tcggaagctg    6240
tggtatggct gtgcaggtcg taaatcactg cataattcgt gtcgctcaag gcgcactccc    6300
gttctggata tgttttttg cgccgacatc ataacggttc tggcaaatat tctgaaatga    6360
gctgttgaca attaatcatc ggctcgtata atgtgtggaa ttgtgagcgg ataacaattt    6420
cacacaggaa acagaa                                                    6436
```

<210> SEQ ID NO 21
<211> LENGTH: 31
<212> TYPE: DNA
<213> ORGANISM: Artificial Sequence
<220> FEATURE:
<223> OTHER INFORMATION: SoxS_for_SphI_tl

<400> SEQUENCE: 21
atctgcatgc cggctggtca atatgctcgt c         31

<210> SEQ ID NO 22
<211> LENGTH: 30
<212> TYPE: DNA
<213> ORGANISM: Artificial Sequence
<220> FEATURE:
<223> OTHER INFORMATION: SoxR_rev_SalI_tl

<400> SEQUENCE: 22
gctagtcgac caaactaaag cgcccttgtg         30

<210> SEQ ID NO 23
<211> LENGTH: 26
<212> TYPE: DNA
<213> ORGANISM: Artificial Sequence
<220> FEATURE:
<223> OTHER INFORMATION: EYFP_for_SphI_tl

<400> SEQUENCE: 23
agaggcatgc gtgagcaagg gcgagg         26

<210> SEQ ID NO 24

```
<211> LENGTH: 35
<212> TYPE: DNA
<213> ORGANISM: Artificial Sequence
<220> FEATURE:
<223> OTHER INFORMATION: EYFP_rev_ClaI_tl

<400> SEQUENCE: 24
gcgcatcgat ttattacttg tacagctcgt ccatg                                  35

<210> SEQ ID NO 25
<211> LENGTH: 6418
<212> TYPE: DNA
<213> ORGANISM: Artificial Sequence
<220> FEATURE:
<223> OTHER INFORMATION: pSenSox_tl

<400> SEQUENCE: 25
ttcatgtcta accgtttgga tggtaaggta gcaatcatta caggtggtac gttgggtatc        60
ggtttagcta tcgccacgaa gttcgttgaa gaagggcta aggtcatgat taccggccgg       120
cacagcgatg ttggtgaaaa agcagctaag agtgtcggca ctcctgatca gattcaattt      180
ttccaacatg attcttccga tgaagacggc tggacgaaat tattcgatgc aacggaaaaa     240
gcctttggcc cagtttctac attagttaat aacgctggga tcgcggttaa caagagtgtc      300
gaagaaacca cgactgctga atggcgtaaa ttattagccg tcaaccttga tggtgtcttc     360
ttcggtaccc gattagggat tcaacggatg aagaacaaag gcttagggg cttccatcatc     420 aacatgtctt cgatcgaagg ctttgtgggt gatcctagct tagggcttaa caacgcatct     480
aaaggggccg tacggattat gtccaagtca gctgccttag attgtgccct aaaggactac    540
gatgttcggg taaacactgt tcaccctggc tacatcaaga caccattggt tgatgaccta    600
ccaggggccg aagaagcgat gtcacaacgg accaagacgc caatgggcca tatcggtgaa    660
cctaacgata ttgcctacat ctgtgtttac ttggcttcta cgaatctaaa atttgcaacg    720
ggttctgaat tgtagttga cggtggctac actgctcaat agtaagcttc tgttttggcg     780
gatgagagaa gattttcagc ctgatacaga ttaaatcaga acgcagaagc ggtctgataa    840
aacagaattt gcctggcggc agtagcgcgg tggtcccacc tgaccccatg ccgaactcag    900
aagtgaaacg ccgtagcgcc gatggtagtg tggggtctcc ccatgcgaga gtagggaact    960
gccaggcatc aaataaaacg aaaggctcag tcgaaagact gggcctttcg ttttatctgt   1020
tgtttgtcgg tgaacgctct cctgagtagg acaaatccgc cgggagcgga tttgaacgtt   1080
gcgaagcaac ggcccggagg gtggcgggca ggacgcccgc cataaactgc caggcatcaa   1140
attaagcaga aggccatcct gacggatggc cttttttgcgt ttctacaaac tcttttgttt   1200 attttctaa atacattcaa atatgtatcc gctcatgaga caataaccct gataaatgct     1260
tcaataatat tgaaaagga agagtatgag tattcaacat ttccgtgtcg ccccttattcc   1320 cttttttgcg cattttgcc ttcctgtttt tgctcaccca gaaacgctgg tgaaagtaaa    1380
agatgctgaa gatcagttgg gtgcacgagt gggttacatc gaactggatc tcaacagcgg   1440
taagatcctt gagagttttc gccccgaaga acgttttcca atgatgagca cttttaaagt   1500
tctgctatgt ggcgcggtat tatcccgtgt tgacgccggg caagagcaac tcggtcgccg   1560
catacactat tctcagaatg acttggttga gtactcacca gtcacagaaa agcatcttac   1620
ggatggcatg acagtaagag aattatgcag tgctgccata accatgagtg ataacactgc   1680
ggccaactta cttctgacaa cgatcggagg accgaaggag ctaaccgctt ttttgcacaa   1740
catgggggat catgtaactc gccttgatcg ttgggaaccg gagctgaatg aagccatacc   1800
```

```
aaacgacgag cgtgacacca cgatgcctgt agcaatggca acaacgttgc gcaaactatt    1860
aactggcgaa ctacttactc tagcttcccg gcaacaatta atagactgga tggaggcgga    1920
taaagttgca ggaccacttc tgcgctcggc ccttccggct ggctggttta ttgctgataa    1980
atctggagcc ggtgagcgtg ggtctcgcgg tatcattgca gcactggggc cagatggtaa    2040
gccctcccgt atcgtagtta tctacacgac ggggagtcag gcaactatgg atgaacgaaa    2100
tagacagatc gctgagatag gtgcctcact gattaagcat tggtaactgt cagaccaagt    2160
ttactcatat atactttaga ttgatttaaa acttcatttt taatttaaaa ggatctaggt    2220
gaagatcctt tttgataatc tcatgaccaa atcccttaa cgtgagtttt cgttccactg    2280
agcgtcagac cccgtagaaa agatcaaagg atcttcttga gatccttttt ttctgcgcgt    2340
aatctgctgc ttgcaaacaa aaaaaccacc gctaccagcg gtggtttgtt tgccggatca    2400
agagctacca actcttttc cgaaggtaac tggcttcagc agagcgcaga taccaaatac    2460
tgtccttcta gtgtagccgt agttaggcca ccacttcaag aactctgtag caccgcctac    2520
atacctcgct ctgctaatcc tgttaccagt ggctgctgcc agtggcgata agtcgtgtct    2580
taccgggttg gactcaagac gatagttacc ggataaggcg cagcggtcgg gctgaacggg    2640
gggttcgtgc acacagccca gcttggagcg aacgacctac accgaactga gatacctaca    2700
gcgtgagcta tgagaaagcg ccacgcttcc gaagggaga aaggcggaca ggtatccggt    2760
aagcggcagg gtcggaacag gagagcgcac gagggagctt ccaggggga acgcctggta    2820 tctttatagt cctgtcgggt ttcgccacct ctgacttgag cgtcgatttt tgtgatgctc    2880
gtcagggggg cggagcctat ggaaaaacgc cagcaacgcg gcctttttac ggttcctggc    2940
cttttgctgg ccttttgctc acatgttctt tcctgcgtta tcccctgatt ctgtggataa    3000
ccgtattacc gcctttgagt gagctgatac cgctcgccgc agccgaacga ccgagcgcag    3060
cgagtcagtg agcgaggaag cggaagagcg cctgatgcgg tatttctcc ttacgcatct    3120 gtgcggtatt tcacaccgca tatggtgcac tctcagtaca atctgctctg atgccgcata    3180
gttaagccag tatacactcc gctatcgcta cgtgactggg tcatggctgc gccccgacac    3240
ccgccaacac ccgctgacgc gccctgacgg gcttgtctgc tcccggcatc cgcttacaga    3300
caagctgtga ccgtctccgg gagctgcatg tgtcagaggt tttcaccgtc atcaccgaaa    3360
cgcgcgaggc agctgcggta agctcatca gcgtggtcgt gaagcgattc acagatgtct    3420
gcctgttcat ccgcgtccag ctcgttgagt ttctccagaa gcgttaatgt ctggcttctg    3480
ataaagcggg ccatgttaag gcggttttt tcctgtttgg tcacttgatg cctccgtgta    3540 aggggaatt tctgttcatg ggggtaatga taccgatgaa acgagagagg atgctcacga    3600
tacgggttac tgatgatgaa catgcccggt tactggaacg ttgtgagggt aaacaactgg    3660
cggtatggat gcggcgggac cagagaaaaa tcactcaggg tcaatgccag cgcttcgtta    3720
atacagatgt aggtgttcca cagggtagcc agcagcatcc tgcgatgcag atccggaaca    3780
taatggtgca gggcgctgac ttccgcgttt ccagacttta cgaaacacgg aaaccgaaga    3840
ccattcatgt tgttgctcag gtcgcagacg ttttgcagca gcagtcgctt cacgttcgct    3900
cgcgtatcgg tgattcattc tgctaaccag taaggcaacc ccgccagcct agccgggtcc    3960
tcaacgacag gagcacgatc atgcgcaccc gtggccagga cccaacgctg cccgagatgc    4020
gccgcgtgcg gctgctggag atggcggacg cgatggatat gttctgccaa gggttggttt    4080
gcgcattcac agttctccgc aagaattgat tggctccaat tcttggagtg gtgaatccgt    4140
```

-continued

```
tagcgaggtg ccgccggctt ccattcaggt cgaggtggcc cggctccatg caccgcgacg      4200
caacgcgggg aggcagacaa ggtatagggc ggcgcctaca atccatgcca acccgttcca      4260
tgtgctcgcc gaggcggcat aaatcgccgt gacgatcagc ggtccagtga tcgaagttag      4320
gctggtaaga gccgcgagcg atccttgaag ctgtccctga tggtcgtcat ctacctgcct      4380
ggacagcatg gcctgcaacg cgggcatccc gatgccgccg gaagcgagaa gaatcataat      4440
ggggaaggcc atccagcctc gcgtcgcgaa cgccagcaag acgtagccca gcgcgtcggc      4500
cgccatgccg gcgataatgg cctgcttctc gccgaaacgt ttggtggcgg gaccagtgac      4560
gaaggcttga gcgagggcgt gcaagattcc gaataccgca agcgacaggc cgatcatcgt      4620
cgcgctccag cgaaagcggt cctcgccgaa aatgacccag agcgctgccg gcacctgtcc      4680
tacgagttgc atgataaaga agacagtcat aagtgcggcg acgatagtca tgccccgcgc      4740
ccaccggaag gagctgactg ggttgaaggc tctcaagggc atcggtcgac caaactaaag      4800 cgccttgtg gcgctttagt tttgttcatc ttccagcaag cgtgcgccgg taccttcttc       4860
tcctaagcgg tcgcccgggt tacgcaacgg gcaatcactg cgcgaaaggc agccacaacc      4920
aatacatccg tccagttcgt cacgcagcgc cactaaggta tgaatgcgcc gatccaactc      4980
ttctcgccat tgggacgaaa gctgtttcca ctctttcgca cttaacgtat gcccttcggg      5040
caacacgcca aacgcttcac caatggtcgc cagcggaatg ccaatacgct gagcaatttt      5100
gataattgca acatatcgca acacatcacg tttatatcgc cgctgattgc cgctgttacg      5160
gatactggta atcaacccct tactttcata gaaatgcagc gccgataccg ccacaccgct      5220
gcgtttcgcc acttcgccgg gggttagcag cgctttaatg cggggtaatt tcttttccat      5280
aaatcgcttt acctcaagtt aacttgagga attatactcc ccaacagatg aattaacgaa      5340
ctgaacactg aaaagaggca gatttatgtc ccatcagaaa attattcagg atcttatcgc      5400
atggattgac gagcatattg accagccggc atgcgtgagc aagggcgagg agctgttcac      5460
cggggtggtg cccatcctgg tcgagctgga cggcgacgta aacggccaca gttcagcgt       5520 gtccggcgag ggcgagggcg atgccaccta cggcaagctg accctgaagt tcatctgcac      5580
caccggcaag ctgcccgtgc cctggcccac cctcgtgacc accttcggct acggcctgca      5640
gtgcttcgcc cgctacccg accacatgaa gcagcacgac ttcttcaagt ccgccatgcc       5700
cgaaggctac gtccaggagc gcaccatctt cttcaaggac gacggcaact acaagacccg      5760
cgccgaggtg aagttcgagg gcgacaccct ggtgaaccgc atcgagctga agggcatcaa      5820
cttcaaggag gacggcaaca tcctggggca caagctggag tacaactaca acagccacaa      5880
cgtctatatc atggccgaca agcagaagaa cggcatcaag gtgaacttca agatccgcca      5940
caacatcgag ggcggcagcg tgcagctcgc cgaccactac cagcagaaca cccccatcgg      6000
cgacggcccc gtgctgctgc ccgacaacca ctacctgagc taccagtccg ccctgagcaa      6060 agacccccaac gagaagcgcg atcacatggt cctgctggag ttcgtgaccg ccgccgggat     6120
cactctcggc atggacgagc tgtacaagta ataaatcgat ccggagctta tcgactgcac      6180
ggtgcaccaa tgcttctggc gtcaggcagc catcggaagc tgtggtatgg ctgtgcaggt      6240
cgtaaatcac tgcataattc gtgtcgctca aggcgcactc ccgttctgga taatgttttt     6300
tgcgccgaca tcataacggt tctggcaaat attctgaaat gagctgttga caattaatca     6360
tcggctcgta taatgtgtgg aattgtgagc ggataacaat ttcacacagg aaacagaa       6418
```